(12) United States Patent
Johnson et al.

(10) Patent No.: US 9,445,880 B2
(45) Date of Patent: Sep. 20, 2016

(54) PORTABLE SYSTEM FOR ASSISTING BODY MOVEMENT

(71) Applicant: Lite Run, Inc., Minneapolis, MN (US)

(72) Inventors: Douglas E. Johnson, Minneapolis, MN (US); John A. Hauck, Shoreview, MN (US); Odd Osland, Apple Valley, MN (US); Mark T. Johnson, Mounds View, MN (US)

(73) Assignee: Lite Run, Inc., Minneapolis, MN (US)

( * ) Notice: Subject to any disclaimer, the term of this patent is extended or adjusted under 35 U.S.C. 154(b) by 704 days.

(21) Appl. No.: 13/748,322

(22) Filed: Jan. 23, 2013

(65) Prior Publication Data

US 2013/0211295 A1    Aug. 15, 2013

Related U.S. Application Data

(63) Continuation of application No. 12/319,463, filed on Jan. 7, 2009, now abandoned.

(60) Provisional application No. 61/131,919, filed on Jun. 13, 2008, provisional application No. 61/010,034, filed on Jan. 7, 2008.

(51) Int. Cl.
   *A61H 3/00* (2006.01)
   *A61H 3/04* (2006.01)
   (Continued)

(52) U.S. Cl.
   CPC . *A61D 3/00* (2013.01); *A61F 5/24* (2013.01); *A61H 3/008* (2013.01); *A61H 3/04* (2013.01); *A61H 9/0057* (2013.01); *A61H 9/0078* (2013.01); *A63B 21/00181* (2013.01); *A61H 3/00* (2013.01); *A61H 2201/163* (2013.01); *A61H 2201/165* (2013.01); *A61H 2201/1616* (2013.01); *A61H 2201/1621* (2013.01); *A61H 2201/1642* (2013.01);
   (Continued)

(58) Field of Classification Search
   CPC ...... A61H 1/00; A61H 1/005; A61H 1/0262; A61H 3/008; A61H 3/00; A61H 3/04; A61H 2003/043; A61H 2003/046; A61H 2003/007; A61H 2201/165; A61H 2201/1652; A61H 2203/0487; A63B 2208/05; A63B 2208/053; A63B 2208/056; A61D 3/00
   See application file for complete search history.

(56) References Cited

U.S. PATENT DOCUMENTS

| 1,629,108 A | 5/1927 | Lake |
| 2,762,047 A | 9/1956 | Flagg et al. |

(Continued)

*Primary Examiner* — Valerie L Woodward
(74) *Attorney, Agent, or Firm* — Dewitt Ross & Stevens SC

(57) ABSTRACT

A differential pressure body suit with external support against body suit migration. In its preferred embodiment, such body suit may comprise a close-fitting, multi-layered suit sealed against a mammal's skin to contain the differential pressure, or a looser-fitting suit that bends at the mammal's joints with minimal force. External support structure includes either fixed or movable mechanical supports attached to the body suit, extraordinary air pressure levels for making the body suit rigid, or exoskeletons attached to the body suit. A cyclic control system can turn the differential pressure condition within the body suit on and off on a selective basis to accommodate the movement of the legs of the mammal. This differential pressure body suit provides a portable and convenient system for, e.g., rehabilitating a skeletal joint injury or training the mammal for injury prevention or athletic performance. The pressurization reduces the weight of the body to greater or lesser extents, and offloads the weight to the ground through the external support means.

63 Claims, 40 Drawing Sheets

(51) Int. Cl.
*A61H 9/00* (2006.01)
*A61D 3/00* (2006.01)
*A61F 5/24* (2006.01)
*A63B 21/00* (2006.01)
*A63B 22/02* (2006.01)
*A63B 22/20* (2006.01)
*A63B 69/00* (2006.01)
*A63B 71/00* (2006.01)
*A63B 22/00* (2006.01)

(52) U.S. Cl.
CPC .. *A61H 2201/5071* (2013.01); *A61H 2203/03* (2013.01); *A61H 2205/08* (2013.01); *A61H 2205/10* (2013.01); *A61H 2209/00* (2013.01); *A63B 22/02* (2013.01); *A63B 22/20* (2013.01); *A63B 69/0064* (2013.01); *A63B 71/0009* (2013.01); *A63B 2022/0094* (2013.01); *A63B 2208/05* (2013.01); *A63B 2208/14* (2013.01)

(56) References Cited

U.S. PATENT DOCUMENTS

| | | | |
|---|---|---|---|
| 2,825,327 | A | 3/1958 | Tunnicliffe |
| 3,355,230 | A | 11/1967 | Trexler |
| 3,589,366 | A | 6/1971 | Feather |
| 3,744,491 | A | 7/1973 | Fischer |
| 3,823,711 | A | 7/1974 | Hatton |
| 4,003,371 | A | 1/1977 | Fischer |
| 4,039,039 | A | 8/1977 | Gottfried |
| 4,151,612 | A | 5/1979 | Vykukal |
| 4,211,223 | A | 7/1980 | LoPiano |
| 4,230,114 | A | 10/1980 | Feather |
| 4,257,407 | A | 3/1981 | Macchi |
| 4,343,302 | A | 8/1982 | Dillon |
| 4,421,109 | A | 12/1983 | Thornton |
| 4,509,513 | A * | 4/1985 | Lasley ............... A61G 10/026 128/202.12 |
| 4,577,622 | A | 3/1986 | Jennings |
| 4,691,695 | A | 9/1987 | Birk et al. |
| 4,959,047 | A | 9/1990 | Tripp, Jr. |
| 5,007,893 | A * | 4/1991 | Row .................. A62B 17/008 128/201.29 |
| 5,029,579 | A | 7/1991 | Trammell |
| 5,133,339 | A * | 7/1992 | Whalen ............... A61H 9/005 128/202.12 |
| 5,176,597 | A * | 1/1993 | Bryne .................. A61H 3/008 482/54 |
| 5,273,502 | A | 12/1993 | Kelsey et al. |
| 5,478,310 | A | 12/1995 | Dyson-Cantwell et al. |
| 5,503,143 | A | 4/1996 | Marion et al. |
| 5,537,686 | A | 7/1996 | Krutz, Jr. et al. |
| 5,704,881 | A | 1/1998 | Dudley |
| 5,865,722 | A | 2/1999 | Heng |
| 5,997,465 | A | 12/1999 | Savage et al. |
| 6,045,519 | A | 4/2000 | Smith, Sr. |
| 6,302,828 | B1 | 10/2001 | Martin et al. |
| 6,460,195 | B2 | 10/2002 | Wang |
| 6,589,194 | B1 | 7/2003 | Calderon et al. |
| 6,757,916 | B2 | 7/2004 | Mah et al. |
| 7,341,543 | B2 | 3/2008 | Dandy |
| 7,381,163 | B2 * | 6/2008 | Gordon ............... A63B 22/02 482/69 |
| 7,591,795 | B2 * | 9/2009 | Whalen ............... A61G 10/023 128/202.12 |
| 2002/0116741 | A1 | 8/2002 | Young |
| 2003/0216672 | A1 | 11/2003 | Rastegar et al. |
| 2004/0063550 | A1 * | 4/2004 | Harris ................. A61H 3/008 482/69 |
| 2005/0070405 | A1 | 3/2005 | Egger |
| 2006/0049611 | A1 | 3/2006 | Stevens |
| 2006/0135889 | A1 | 6/2006 | Egli |
| 2006/0189899 | A1 | 8/2006 | Flaherty et al. |
| 2007/0157651 | A1 | 7/2007 | Naaman |
| 2007/0179421 | A1 | 8/2007 | Farrow |

* cited by examiner

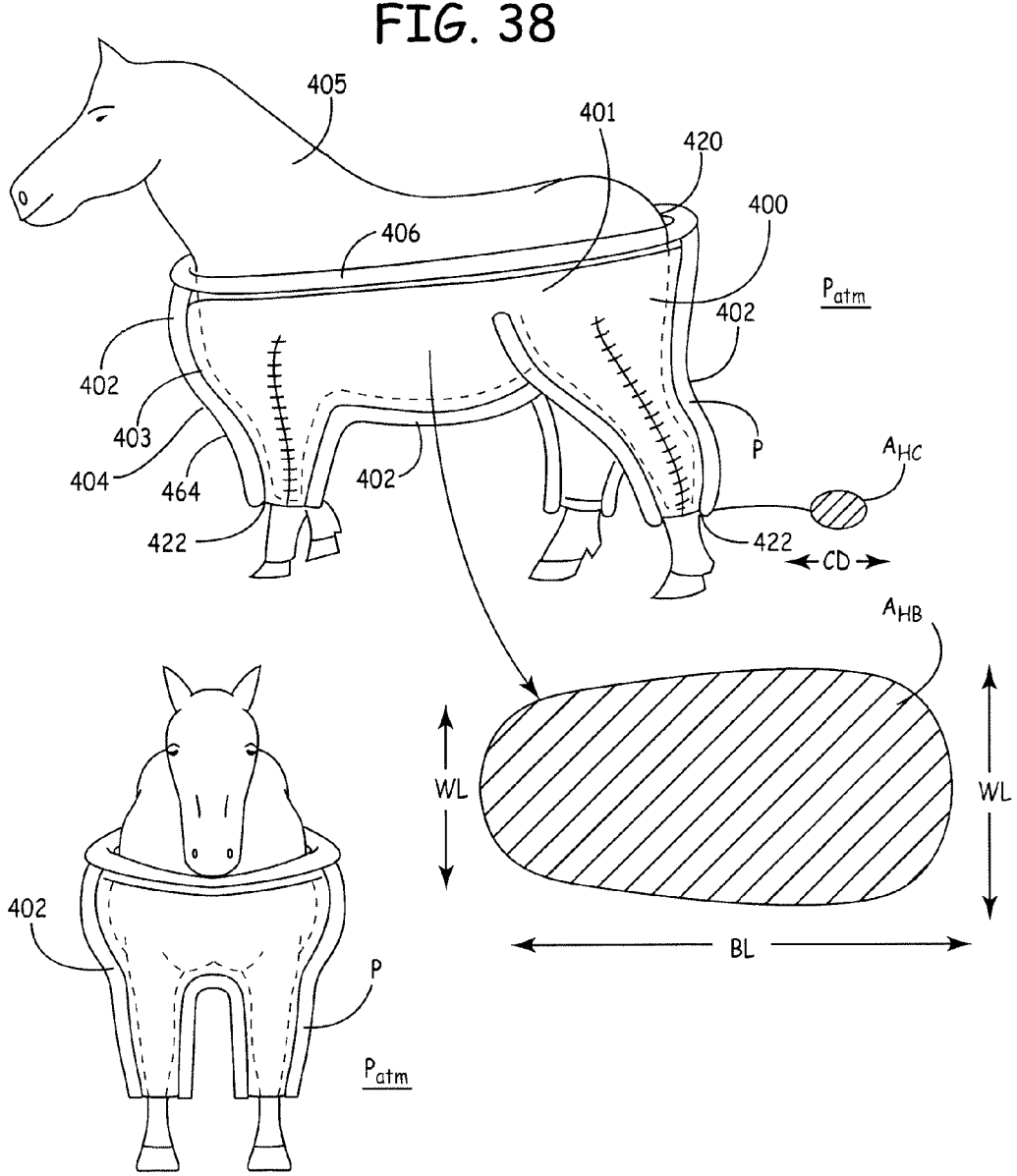

PORTABLE SYSTEM FOR ASSISTING BODY MOVEMENT

CROSS-REFERENCE TO RELATED APPLICATIONS

This application is a continuation of application Ser. No. 12/319,463 filed on Jan. 7, 2009, which claims priority to U.S. provisional application Ser. Nos. 61/010,034 filed on Jan. 7, 2008, and 61/131,919 filed on Jun. 13, 2008, all of which are incorporated herein by reference in their entirety.

FIELD OF THE INVENTION

This invention relates generally to the motion and physical health of the mammalian body, and more specifically to portable systems for assisting humans or other animals to medically rehabilitate or train specific body parts through the application to such body parts of differential pressure.

BACKGROUND OF THE INVENTION

Vertebrate animals feature a flexible, bony skeletal framework that provides the body shape, protects vital organs, and enables the body to move. The human skeleton comprises approximately 206 separate bones. These bones meet at joints, the majority of which are freely movable. The skeleton also contains cartilage for elasticity, and muscular ligaments consisting of strong strips of fibrous connective tissue for holding the bones together at their joints.

The femur, fibula, tibia, and metatarsal bones of the legs and feet support the body and therefore bear its weight. Muscles associated with the ilium, pubis, ischium, patella, tarsal, and phalanges bones provide the necessary bending of the hips, knees, ankles, and toes that are essential for humans to walk, run, climb, and engage in other locomotion activities.

Likewise, the humerus, ulna and radius bones and metacarpal and phalanges bones form the arms and hands, respectively. Muscles associated with the clavicle, scapula, and carpals enable the arm to bend or flex at the shoulder or elbow, and the hand to flex at the wrist and fingers, which is useful for lifting, carrying, and manipulating objects.

Over time, body bones or joints can become damaged. Bones fracture; ligaments tear; cartilage deteriorates. Such damage may result from the aging process, manifested by arthritis, osteoporosis, and slips and falls. But injuries are also caused by sports activities. For example, recreational and competitive running is enjoyed by some 37 million Americans with 25% of them suffering from running injuries annually. Meanwhile, 57 million Americans bicycle for recreational or transportation purposes. In addition to bodily injuries caused by falls, prolonged bicycling can result in groin discomfort or numbness. This medical injury is caused by the horn of the bicycle saddle creating pressure points that can that can occlude the arteries and veins that supply blood flow to the genitals. Within the 1999-2004 time period, 21 publications within multiple medical specialties (e.g., sexual medicine, urology, neurology, cardiology, biomedical engineering, sports medicine and emergency medicine) established a clear relationship between bicycle riding and erectile dysfunction ("ED").

A number of different approaches have been taken within the industry and the medical community for preventing or treating these injuries. Exoskeletons entail external support systems made from strong materials like metal or plastic composite fibers shaped for supporting proper posture of the human body. Honda Motor Co. has employed "walking assist devices" for its automotive factory workers to support bodyweight for reducing the load on assembly line workers' legs while they walk, move up and down stairs, and engage a semi-crouching position throughout a work shift. The U.S. military has experimented with exoskeletons for its soldiers to enable them to carry heavy equipment packs and weapons. However, the body must be connected to the exoskeleton at the limbs and other parts by means of straps and other mechanical attachment devices. The exoskeleton's motor must be regulated by various sensors and controls, and driven by hydraulics, pneumatics, springs, or other motorized mechanical systems. These can be cumbersome and expensive systems that do not necessarily reduce the stress on the body caused by gravity.

Athletes and older people suffering from joint injuries have rehabilitated in pools and water tanks. The buoyant property of the water provides an upwardly-directed force to the body that lightens the load otherwise directed to the joints. However, these types of systems are not portable, since the person is confined to the pool or water tank. Moreover, pools or water tanks may be unavailable or expensive to install.

Another approach is provided by a harness system exemplified by U.S. Pat. No. 6,302,828 issued to Martin et al. Consisting of an overhead frame to which is connected a raiseable body harness, such a system supports a portion of a person's body weight as he, e.g., walks or runs on a treadmill in order to diminish downward forces on the body joints. But the straps and attachment devices create localized pressure points and stresses on the body, and restrict the range of motion of the body and its limbs. Such a mechanical weight off-loading system may also lack portability.

The National Aeronautics and Space Administration ("NASA") has developed a system that utilizes differential air pressure to provide a uniform "lift" to the body to assist the exercise process. See U.S. Pat. No. 5,133,339 issued to Whalen et al. The differential pressure is applied to the lower half of the person's body that is sealed within a fixed chamber to create a force that partially counteracts the gravitational force on the body. A treadmill contained within the sealed chamber allows the person to exercise. However, this Whalen system requires a large, immobile pressure chamber containing a treadmill. Such a system is expensive and requires cumbersome entry and exit by the person. It will not enable the person any other means of exercise besides the treadmill.

Pressurized bodysuits have also been used within the industry for several different applications. For example, U.S. Published Application 2002/0116741 filed by Young discloses a bodysuit with integral supports and internal air bladders that are filled with pressurized air. This air pressure exerts force against the muscles of a person wearing the suit to tone them during daily activities. U.S. Pat. No. 6,460,195 issued to Wang illustrates exercise shorts with buckled belts, air bags, and a vibrator that directs pulses of pressurized air to the body to work off fat and lift the hips. U.S. Pat. No. 3,589,366 issued to Feather teaches exercise pants from which air is evacuated, so that the pants cling to the body of an exerciser to cause sweating, thereby leading to weight loss.

The U.S. military has also employed pressurized suits of various designs for protecting fighter pilots from debilitating external G-forces. Due to rapid changes in speed and direction, the fighter pilot's body undergoes very high accelerations. This normally forces the pilot's oxygen-laden blood away from the portion of the circulatory system between the heart, lungs and brain, pooling instead toward the blood vessels of the lower extremities. As a result, the pilot can lose situational awareness and spatial orientation. A pilot's bodysuit pressurized against the blood vessels of the legs can force the oxygen-laden blood back to the head and torso of the pilot. See U.S. Pat. No. 2,762,047 issued to Flagg et al.; U.S. Pat. No. 5,537,686 issued to Krutz, Jr. et al.; and U.S. Pat. No. 6,757,916 issued to Mah et al. U.S. Pat. No. 5,997,465 issued to Savage et al. discloses a pants bodysuit made from metal or polymer "memory material" that is heated by electrical current to form around the body, and then cooled to apply pressure for treating this G-forces phenomenon.

Pressurized bodysuits have been used previously for other purposes, such as splinting leg fractures, stopping bleeding from wounds, treating shock, and supporting the posture of partially paralyzed patients. See, e.g., U.S. Pat. No. 3,823,711 issued to Hatton; U.S. Pat. No. 3,823,712 issued to Morel; U.S. Pat. No. 4,039,039 issued to Gottfried; and U.S. Pat. No. 5,478,310 issue to Dyson-Cartwell et al. Bodysuits can also have air between the suit and the body evacuated by vacuum to draw the suit into close contact with the body. See U.S. Pat. No. 4,230,114 issued to Feather; U.S. Pat. No. 4,421,109 issued to Thornton; and U.S. Pat. No. 4,959,047 issued to Tripp, Jr. See also U.S. Published Application 2006/0135889 filed by Egli.

Such pressurized body suits have not previously been used to rehabilitate skeletal joint injuries or minimize conditions that cause erectile dysfunction. Moreover, they have typically been used only in stationary situations like a sitting pilot due to the problem of air pressure forcing the body suit off the lower torso. In some applications like weight-loss patients, suspender straps have been required to overcome this downwards migration of the bodysuit pants.

Thus, a pressurized bodysuit that can be used to apply localized differential pressure to a lower or upper body part for injury rehabilitation or minimization, coupled with an external support or pressure condition control system would be beneficial, particularly due to its portable nature. Such a pressurized body suit system could be worn by a patient, athlete, or other person within a variety of settings to perform a variety of different functions.

SUMMARY OF THE INVENTION

The present invention provides a differential pressure body suit with external support against body suit migration. In its preferred embodiment, such body suit may comprise a close-fitting, multi-layered suit sealed against a mammal's skin to contain the differential pressure, or a looser-fitting suit that bends at the mammal's joints with minimal force. External support means include either fixed or movable mechanical supports attached to the body suit, extraordinary air pressure levels for making the body suit rigid, or exoskeletons attached to the body suit. A cyclic control system can turn the differential pressure condition within the body suit on and off on a selective basis to accommodate the movement of the legs of the mammal. This differential pressure body suit provides a portable and convenient system for rehabilitating a skeletal joint injury or training the mammal for injury prevention or athletic performance. The pressurization reduces the weight of the body to greater or lesser extents, and offloads the weight to the ground through the external support means. The body suit is flexible and has joints that can flex with minimal force even under pressure.

The invention can also be used to assist the mobility for, e.g., the elderly or disabled people, who have common problems such as degenerative hips or knees by reducing the stress on their joints. Furthermore, the alternating pressure/depressurization cycle can provide medical benefits via the body suit similar to massage, or by enhancing venous return of blood to the heart for, e.g., people suffering from varicose veins or other vascular disorders. The system can also facilitate proper posture, and avoid bed sores caused by prolonged horizontal contact by the body with the bed. This is not a purely mechanical system for supporting bodily motion, such as an exoskeleton. This invention is useful not only for humans, but also for other animals like dogs, cats, and horses.

BRIEF DESCRIPTION OF THE DRAWINGS

In the accompanying drawings:

FIG. 38 is a perspective view of a body suit for a horse.

FIG. 39 is a front view of the body suit of FIG. 38.

DETAILED DESCRIPTION OF THE PREFERRED EMBODIMENT

Figure 1:
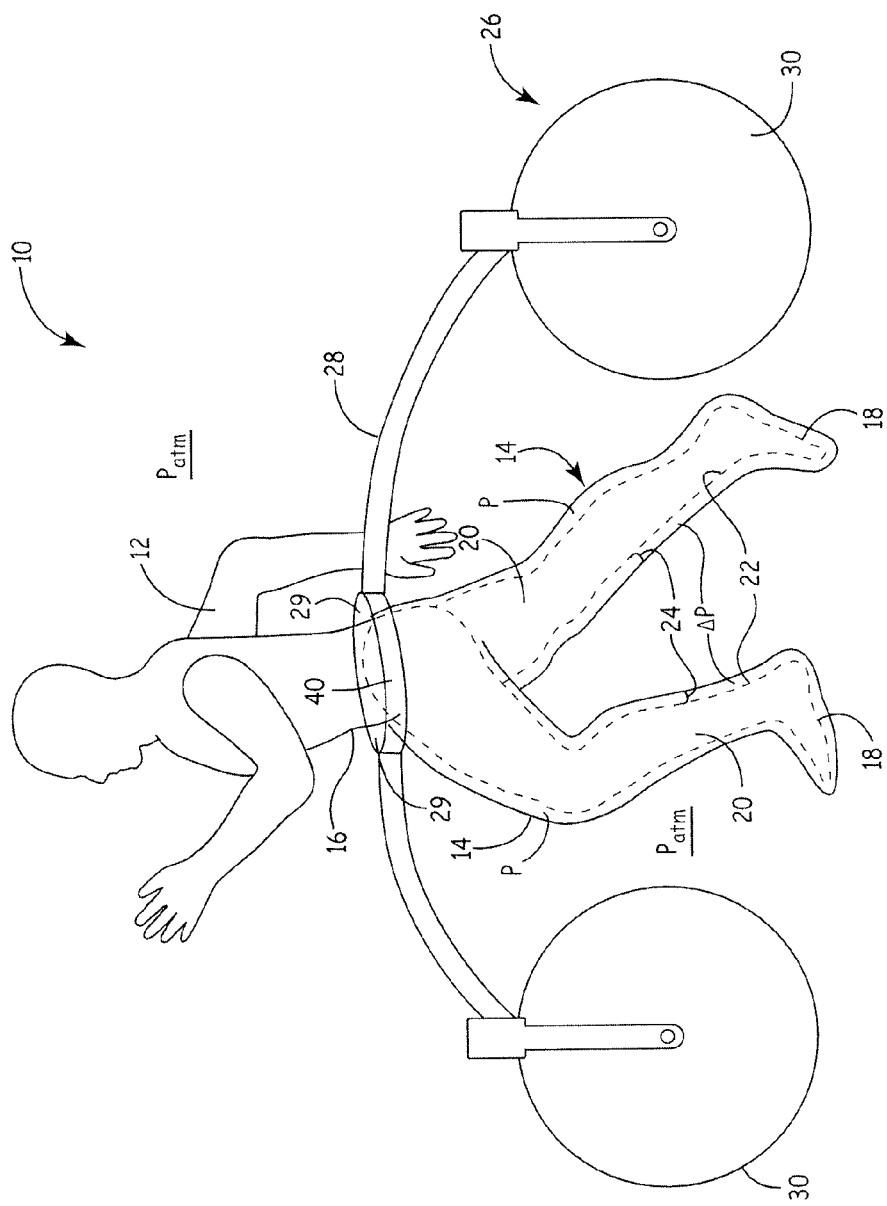
FIG. 1 is a perspective view of the assisted motion system of the present invention.

A differential pressure body suit with external support against body suit migration is provided by the invention. In its preferred embodiment, such body suit may comprise a close-fitting, multi-layered suit sealed against a mammal's skin to contain the differential pressure, or a looser-fitting space suit that bends at the mammal's joints with minimal force. External support means include either fixed or movable mechanical supports attached to the body suit, extraordinary air pressure levels for making the body suit rigid, or exoskeletons attached to the body suit. A cyclic control system can turn the differential pressure condition within the body suit on and off on a selective basis to accommodate the movement of the legs of the mammal. This differential pressure body suit provides a portable and convenient system for rehabilitating a skeletal joint injury or training the mammal for injury prevention or athletic performance. The pressurization reduces the weight of the body to greater or lesser extents, and offloads the weight to the ground through the external support means. The body suit is flexible and has joints that can flex with minimal force even under pressure. The invention can also be used to assist the mobility for, e.g., the elderly or disabled people, who have common problems such as degenerative hips or knees by reducing the stress on their joints. Furthermore, the alternating pressure/depressurization cycle can provide medical benefits via the body suit similar to massage, or by enhancing venous return of blood to the heart for, e.g., people suffering from varicose veins or other vascular disorders. This is not a purely mechanical system for supporting bodily motion, such as an exoskeleton.

For purposes of the present invention, "differential pressure" means the difference in pressure conditions across opposite sides of the body suit, such as a positive pressure or negative (vacuum) pressure condition contained inside the suit, and an atmospheric pressure condition on the outside of the suit. For example, if atmospheric pressure is equal to 14.7 lbs/in$^2$ ("psi"), and the internal pressurized condition of the body suit is 15.7 psi, then the differential pressure applied by the body suit to the mammal wearing the body suit is 1.0 psi. Such differential pressure can also be represented as $\Delta P$ within this application.

As used within this application, "positive pressure" means any pressure level in excess of atmospheric pressure.

For purposes of this application, "negative pressure" means any pressure level less than atmospheric pressure. A vacuum is an example of such a negative pressure. Partial vacuums are also covered by this invention.

In the context of the present invention, "body portion" means any part of the body to which the differential pressure condition is applied by the body suit. Examples include, without limitation, feet, legs, knees, hips, shoulders, arms, elbows, torso, and the back.

As used within this application, "body suit" means a single or multi-layered, close-fitting or loose-fitting suit capable of containing a positive or vacuum pressure condition that covers a predetermined body portion. Examples include, without limitation, trunks, shorts, full-length pants, such pants that cover the feet, shirts, and chest or arm segments. The suit is provided with a means for creating the positive or negative (vacuum) pressure condition within the suit. Such a means may be a port connected to an air pressure control system.

In the context of the present invention, "pressure-tight" means with respect to the body suit that the material forming such body suit is capable of containing a positive or negative pressure condition without substantial diminishment over a time period that is relevant to the usage of the body suit. Thus, pressure tightness does not require an absolute absence of any loss of pressure or vacuum, nor does it require maintenance of the positive pressure or vacuum condition within the suit for a time period greater than the time interval during which the suit is worn for an exercise or therapeutic treatment session, or beyond which such positive pressure or vacuum condition can reasonably be replenished within such exercise or therapeutic session.

For purposes of the present invention, "mammal" means any of a class of higher vertebrates comprising humans and all other animals that nourish their young with milk secreted by mammary glands, and have the skin usually more or less covered with hair. Such animals include, without limitation, horses, dogs, and cats.

A human runner will be used as an exemplary mammal for purposes of describing the assisted motion system of the present invention. It is important to appreciate, however, that any other type of mammal for any other kind of exercise, life activity, or rehabilitative activity is covered by this application, as well.

The assisted motion system 10 of the present invention is shown in FIG. 1. Unlike prior art static systems that require a runner to use a stationary treadmill, this system is portable, thereby enabling the runner 12 to enjoy exercising outdoors on the road or a trail. In this embodiment, the runner wears a differential pressurized pant suit 14 that extends downwardly from the runner's waist 16 and covers the feet 18. The runner's legs are depicted inside the differential pressurized suit 14 in broken lines 22.

The differential pressurized suit 14 is constructed of air-tight material, and affords easy movement by the body and limbs of runner 12 while running. The suit 14 is sealed against the body at the waist 16. When air pressure condition P above atmospheric pressure $P_{atm}$ is added to the volumetric region 24 defined between the runner's legs 20 and the suit 14, a differential pressure condition ΔP is created in which the runner's lower body portion contained within the suit 14 experiences a higher pressure condition than the runner's upper body 26, which only experiences $P_{atm}$. Due to this pressure differential ΔP, an upwards force is exerted on the runner 12 by the higher air pressure contained inside the suit 14, thereby acting to diminish the weight of the runner's body. Runner 12 thereby experiences a reduced weight on his feet, knees, legs, and lower body when he runs in this differential pressurized suit 14, compared with if he ran without the suit.

Figure 2B:
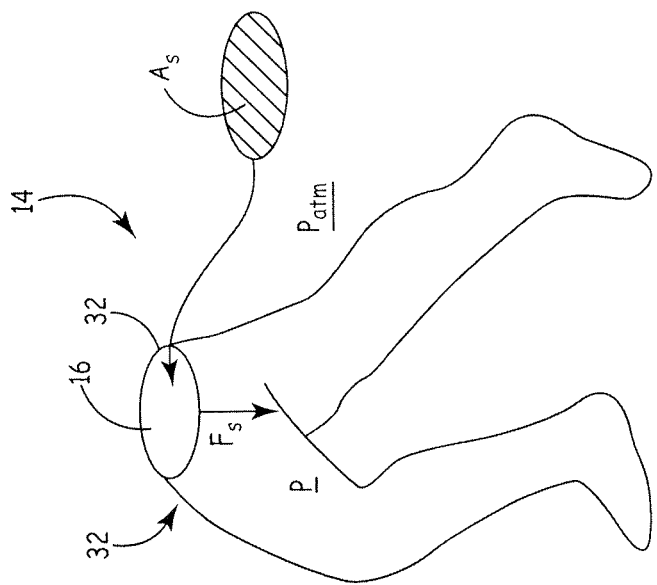
FIG. 2b is a schematic view of a body suit of the present invention and the forces applied thereto.
Figure 2A:
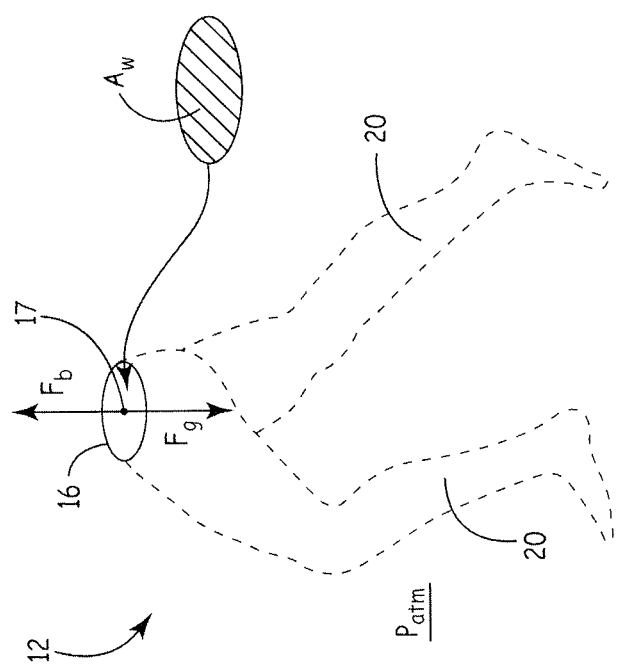
FIG. 2a is a schematic view of the legs and feet of a human and the forces applied thereto.

FIG. 2 illustrates the various vector forces on the runner's body. The runner 12 and the differential pressurized suit 14 are depicted separately in FIGS. 2a and 2b, respectively, for ease of understanding. The force from gravity exerted on the runner's body mass is shown as $F_g$. In use, the suit 14 is sealed to the runner's body at the waist 16, and pressurized to pressure P to create the differential pressure condition ΔP between the upper and lower bodies. The cross-sectional area of the body at waist 16 is depicted as area $A_w$. The positive pressure P is directed against the body and legs 20. The differential pressure condition ΔP results in an upwards-directed resultant force $F_b$ on the body located at the centroid 17 of cross-sectional area $A_w$. This total upwards force $F_b$ is:

$$F_b = \Delta P \times A_w$$

This constitutes the amount of weight that is effectively reduced from the lower body 20 of runner 12. For example, a runner experiencing a pressure differential ΔP on the lower body of 0.5 psi having a cross-sectional waist area of $A_w$ of 100 square inches would experience a 50 lb reduction in weight due to the differential pressurized suit 14.

FIG. 2b illustrates the various vector forces on the suit 14. The cross-sectional area of the suit at waist 16 is depicted as $A_s$. In the case of a closely-fitting body suit, $A_s$ should approximate $A_w$. The positive pressure differential ΔP also results in a downwards directed force $F_s$ on the suit 14. The amount of this downwards force $F_s$ is:

$$F_s = \Delta P \times A_s.$$

This constitutes the amount of force that pushes the suit down the body. For example, a suit pressurized to a pressure differential ΔP of 0.5 psi having a cross-sectional waist area As of 100 square inches is subject to a 50 lb downwards force. This force $F_s$ would ordinarily cause suit 14 to work its way downwardly along legs 20. Therefore, an important part of the invention is the inclusion of external support 26 to prevent the downward migration of the suit. In the case of the embodiment depicted in FIG. 1, external support 26 constitutes a frame 28 that is operatively connected to wheels 30. The suit is attached to the frame 28 at attachment points 29. When the differential pressurized suit 14 is connected to frame 28, the downward force $F_s$ exerted on the suit 14 is matched by the upwards reaction force exerted by the supporting structure at the attachment points 32.

In this manner, the supported differential pressurized suit 14 is able to diminish the weight of the runner's body without contacting the body. Through the application of differential pressure ΔP, an amount of weight ΔW of the body equal to:

$$\Delta W = W - (\Delta P \times A_w)$$

is transferred from the muscle-skeletal structure of the runner's lower body to the support structure 28 of the external support 26, and through the support structure 28 and wheels to the ground. Moreover, the support structure prevents force $F_s$ from pulling the differential pressurized suit 14 off runner 12. Furthermore, because the wheel-based support structure 26 and differential pressurized suit 14 are completely portable in nature, runner 12 can go anywhere with the motion-assisted system 10, instead of being confined to a stationary or pressure chambers as with prior art systems.

When the runner's body is in contact with the ground via feet 18, various amounts of weight can be effectively removed from the body, depending upon the level of positive pressure P introduced to the body suit. For example, for a 180 lb runner having a cross-sectional area $A_w$ of 100 square inches, a differential pressure ΔP of 1 psi would reduce his weight by 100 lbs. The runner's lower body would therefore only need to support a weight of 80 lbs. A 0.5 psi pressure differential ΔP would take off 50 lbs of weight. A 0.25 psi pressure differential would take off 25 lbs of weight.

Figure 3:
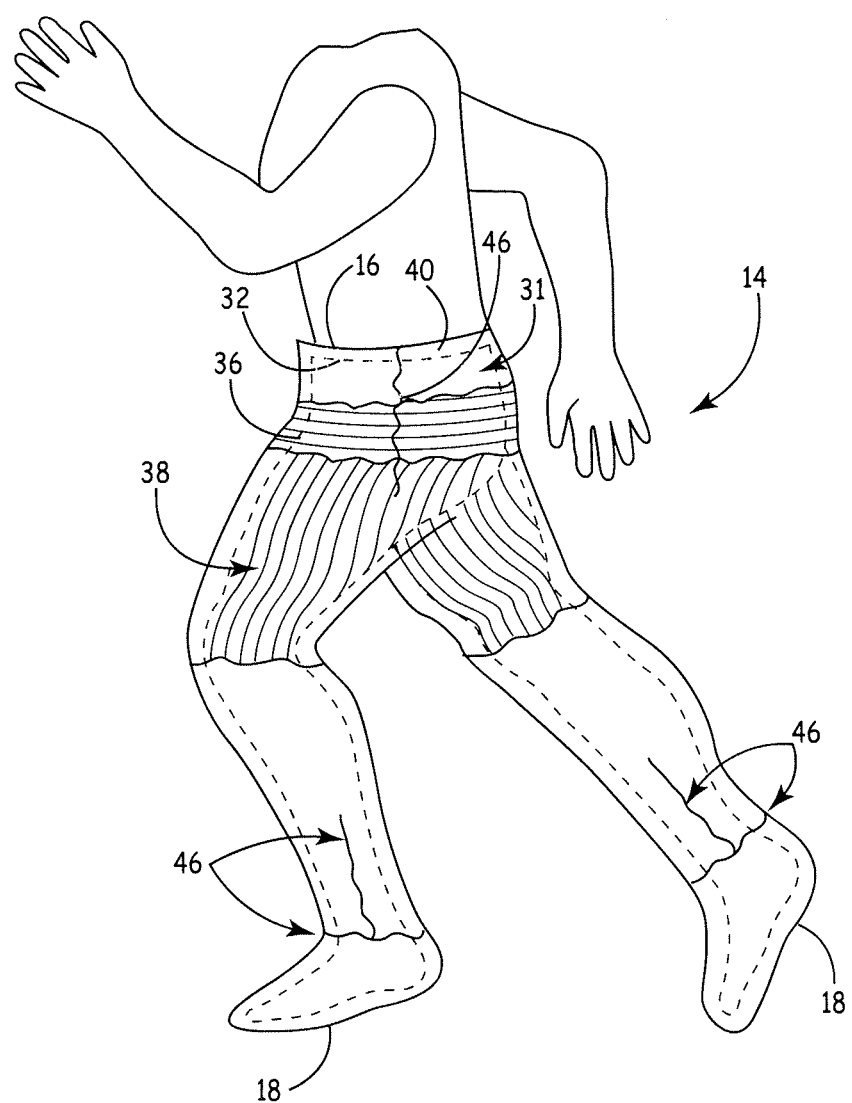
FIG. 3 is a cut-away view of the body suit.
Figure 4:
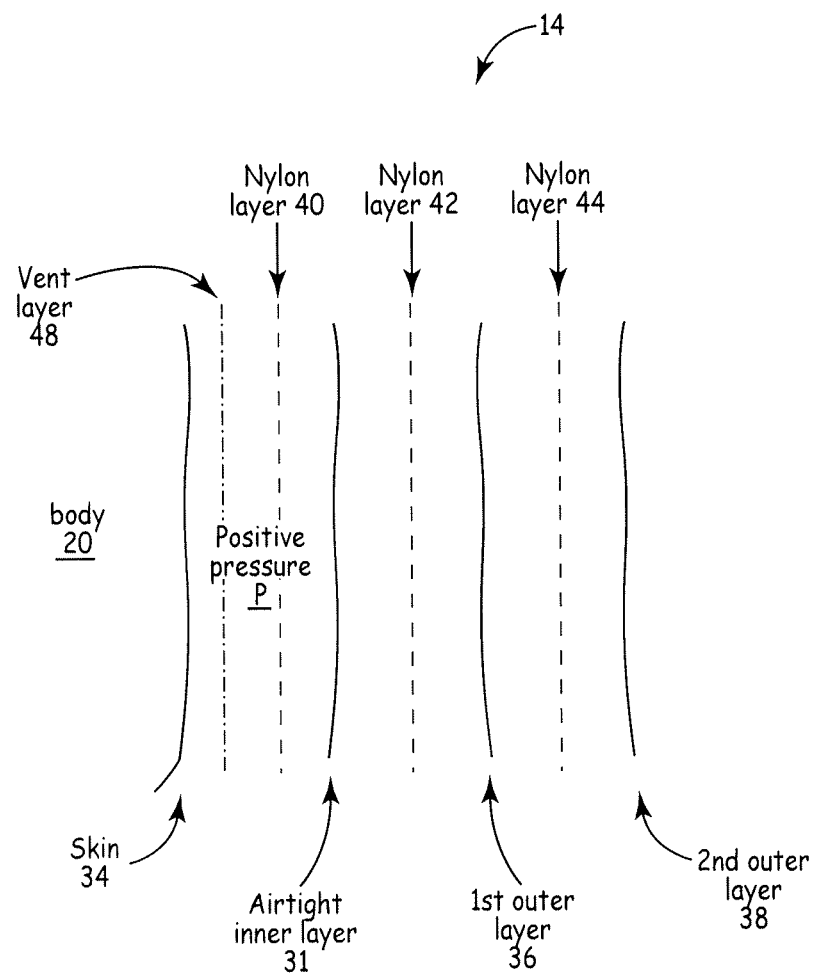
FIG. 4 is a schematic view of the construction of the body suit.

The preferred construction of differential pressurized suit 14 is shown in greater detail in FIGS. 3-4. Close fitting suits provide the advantage of greater mobility for runner 12. Suit 14 is constructed from at least three layers of material. FIG. 3 shows a cut-away view of the suit illustrating its different layers.

An air-tight inner layer 31 featuring an airtight seal 32 at the waist 16 of the runner's body maintains the positive pressure P condition inside the suit against the runner's body skin 34. The fabric for this air-tight layer which is closest to the body may be formed from any pressure-tight material that is also sufficiently flexible to afford mobility by the runner. Examples include, without limitation, latex rubber, neoprene, and air-tight elastic fabrics like latex-coated Lycra. This fabric should be sufficiently thin and elastic to provide comfort without restriction. Preferably, suit 14 is about 0.002-0.040 inch thick, more preferably about 0.005-0.015 inch thick, still more preferably about 0.010 inch thick. The elasticity of the material can be expressed by spring rate, which is the force necessary to double a one-inch-thick strip of fabric. Preferably, this spring rate should be about 0.2-2.0 lbs, more preferably about 0.5-1.5 lbs, still more preferably about 1.0 lb.

Two outer layers 36 and 38 of the differential pressurized suit 14 composition prevent the suit from expanding due to the force applied by positive pressure P, while maintaining the shape of the suit to fit closely to the body. This close fit provides for ease of mobility of the body and its limbs. It also prevents the legs of the suit from contacting each other during the running motion. Moreover, this close fit of the suit reduces the volume of pressurized air or other suitable gas in contact with the body joints in order to facilitate bending of the legs.

The fabric for these first and second outer layers 36 and 38 should be composed of mesh, netting, or other suitable fabric. Suitable mesh material is available from Apex Mills Corporation of Inwood, N.Y. This mesh or netting is constructed to mostly be non-extending along one axis, and elastic or extensible along a second axis perpendicular to the first axis. Exemplary mesh materials include, without limitation, nylon-Lycra that can be knit or braided, or a monofilament like nylon or Dacron.

The first outer layer 36 serves to prevent the suit 14 from expanding circumferentially. The circumferential direction of expansion is perpendicular to the longitudinal axis of the legs and body fabric. The fabric is oriented so that its non-extending axis follows this direction. The fabric can be more specifically oriented so that its non-extending axis follows lines on the body in which the skin does not stretch or extend during bending or other movement. These lines are known within the industry as "lines-of-non-extension." Lines of non-extension run both parallel and perpendicular to the longitudinal axis of the legs and body. This first layer of fabric preferably would follow the perpendicular lines of non-extension.

The second outer layer 38 serves to prevent the suit 14 from expanding longitudinally under pressure. This fabric layer is oriented, so that its axis of non-extension generally follows lines that are generally parallel to the longitudinal axis of the legs and body. Preferably, the fabric can be more specifically oriented in this direction to follow longitudinal lines on the body in which the skin does not stretch or extend during bending or other movement. Where appropriate in sections of the body which do not flex, such as the thigh area or lower calves, cloth, mesh, or net material that is non-extendible along both axes may be used. This second outer fabric layer 38 which is mostly non-extensible in the vertical direction of an upright body effectively carries the vertical downward load on the suit resulting from the positive pressure differential.

Differential pressurized suit 14 may also feature additional layers of nylon 40 between the body 20 and the air-tight inner layer 30, and 42 and 44 between the inner 30 and first outer layer 36, and two outer layers 36 and 38, respectively, in order to enable the suit and layers to slip relative to one another on the body to improve the runner's mobility. Air-tight zippers 46 positioned along the suit 14 near its waist 16 and feet 18 portions allow for easy entry and removal of the suit. Such air-tight zippers are available from YKK (U.S.A.) Inc. of Marietta, Ga. Moreover, the suit 14 may feature an inner vent layer 48 that provides airflow and moisture control. In other embodiments these layers can be separately combined into a single layer that provides the same basic functioning as for the separate layers described above.

Figure 5:
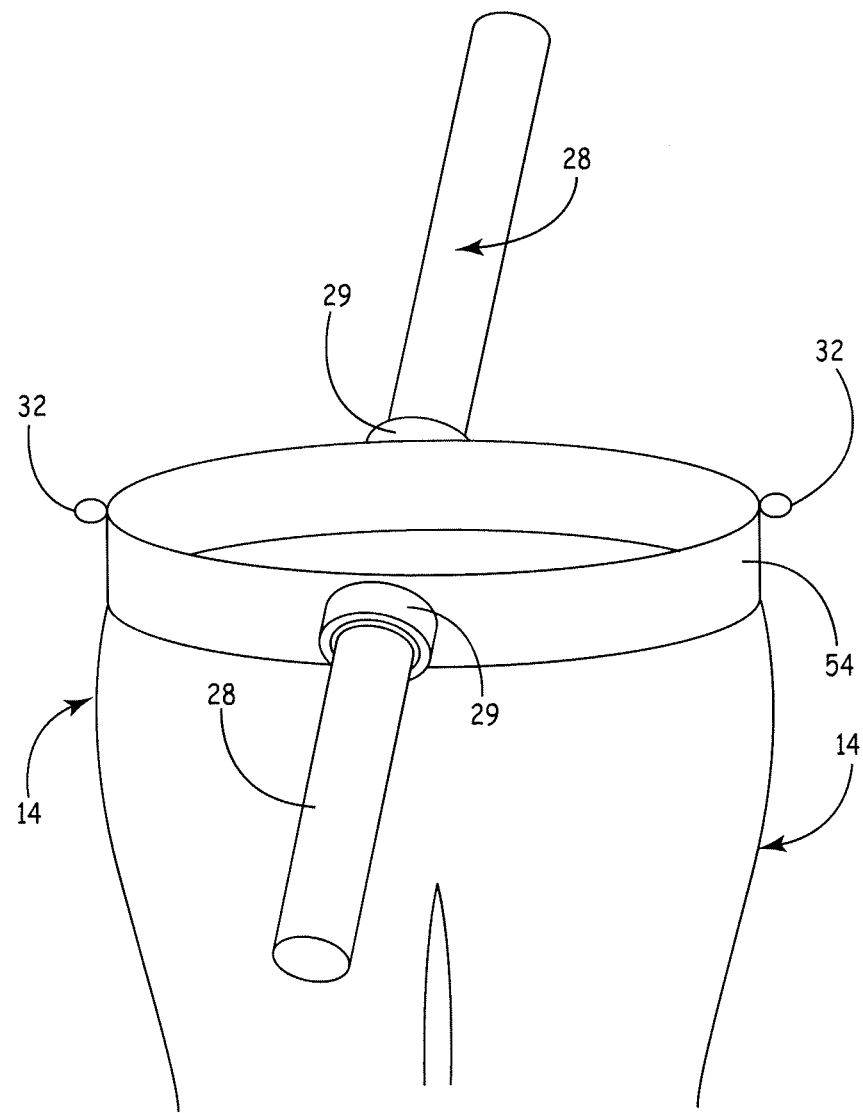
FIG. 5 is a partial view of the body suit connected to a portion of the external support frame.

As shown in FIG. 5, a band 54 serves to attach the suit 14 to the supporting structure 28. This band is attached to the supporting structure with a fitting 29, such as a threaded collar receiving threaded ends extending from support structure 28. The band should conform to the generally elliptical shape of waist cross-section $A_w$ that surrounds the suit 14 at the waist 16. This band serves an additional purpose of containing the outward pressure force in order to enhance the radial inward force as the suit is filled with pressure. This assures that the suit will conform closely to the body at the waist 16.

The band 54 may be made from any suitable material that is strong enough to contain this outwardly-directed force, including metal, plastic, or composites. It may be made moldable to the general shape of the runner's waist, using a thermoset plastic material. The band 54 may alternatively be formed from a strong, flexible fabric, such as nylon. The suit 14 may be attached and detached from the band 54, using a Velcro fastening system. Other mechanical fastening systems such as straps, snaps, or hooks engaging eyelets may also be utilized. Alternatively, the band can constitute an integral part of the suit. The band may be in two pieces hinged and fitted with a locking clasp to allow for easy entry.

In the embodiments of the differential pressurized suit 14 shown in FIGS. 1-3, the suit covers the entire lower legs and feet, so that the entire lower body below the waist is airtight. A seal 40 is connected to the waist of suit 14 with an airtight connection, so that air pressure cannot escape between the suit and the seal. While the seal 40 may be positioned at the waist area, it may also be located lower, below the hips, or somewhere in between.

Figure 6:
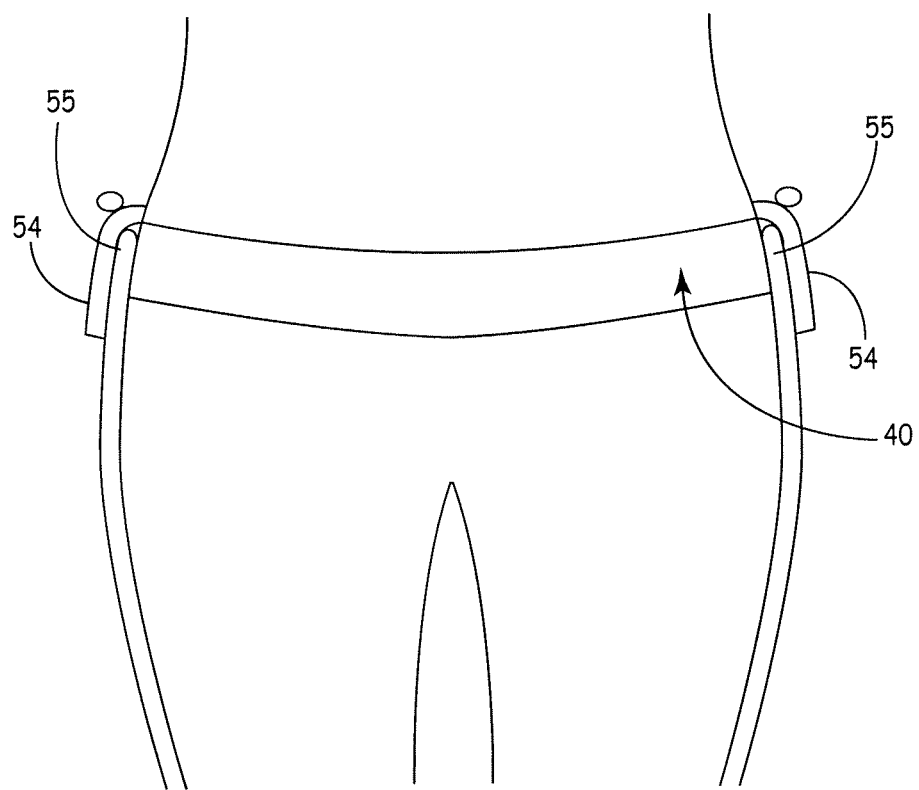
FIG. 6 is a partial front view of a waist seal attached to the interior of the body suit.

The seal 40 constitutes an airtight band of material that fits tightly over the body. As shown more clearly in FIG. 6, it is attached to the suit 14 at 55. This seal 40 is preferably constructed of elastic neoprene, or any other airtight material, such as rubber, latex, or a rubber-coated Lycra. Suitable latex rubber sheeting is available from Rubber Cal of Santa Ana, Calif. The seal should be sufficiently wide across the waist area of the suit to provide for a sufficient airtight closure. The circumference of the seal 40 should be less than the unstretched circumference of the body part that is circumscribed by the seal, so that when the seal 40 is secured around the body part (in this case, the waist area), a positive pressure is applied by the seal to the underlying skin. Combined with the air at pressure P that is introduced into the suit 14 within the volume between the suit's airtight inner layer 30 and the runner's body skin, the suit 14 and associated seal 40 maintain a relatively airtight seal in order to confine the volume of air pressure P inside the suit. The seal 40 is sufficiently airtight that it provides enough sealing force to maintain the air pressure inside the suit using the air control system.

Figure 7:
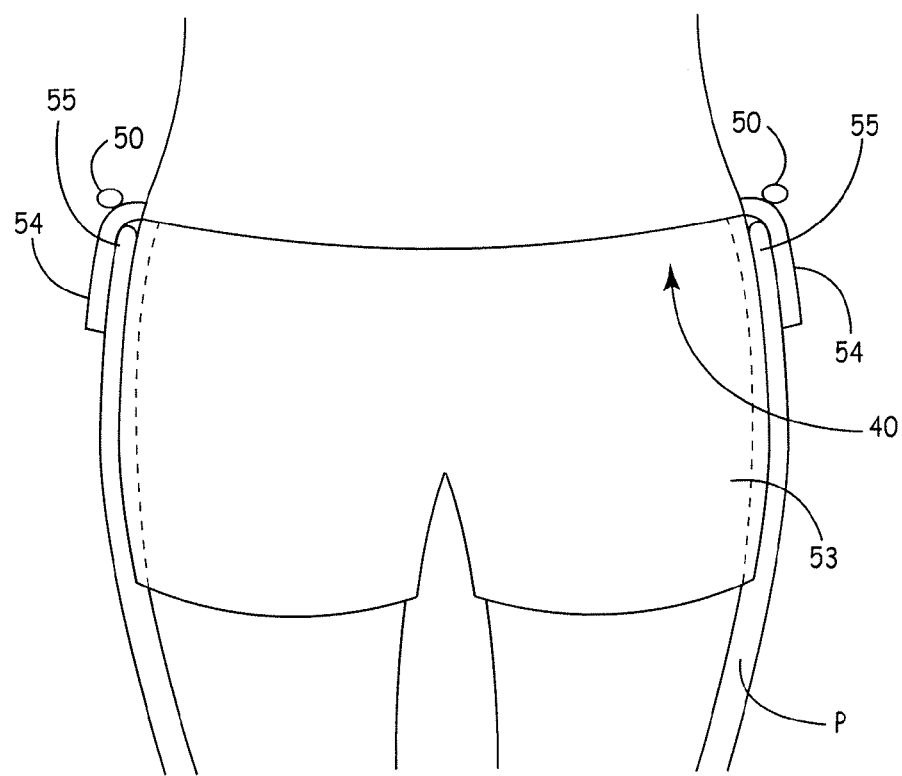
FIG. 7 is a cut-away front view of an alternative airtight shorts embodiment of a waist seal for the body suit.

FIG. 7 shows another embodiment of a waist seal for suit 14. In another embodiment of the differential pressurized suit 14 of the present invention, the waist seal can comprise an airtight pair of shorts 53 that are connected to the interior of the suit. Such shorts can be tight-fitting, airproof neoprene compression shorts that provide a tight fit against the body. These shorts can be connected to the suit at the waist by means of an airproof zipper. The shorts can also consist of a tight-fitting, breathable fabric that has a band of airproof latex or rubber coating at the top or bottom portion to provide the airproof seal against the body.

Figure 8:
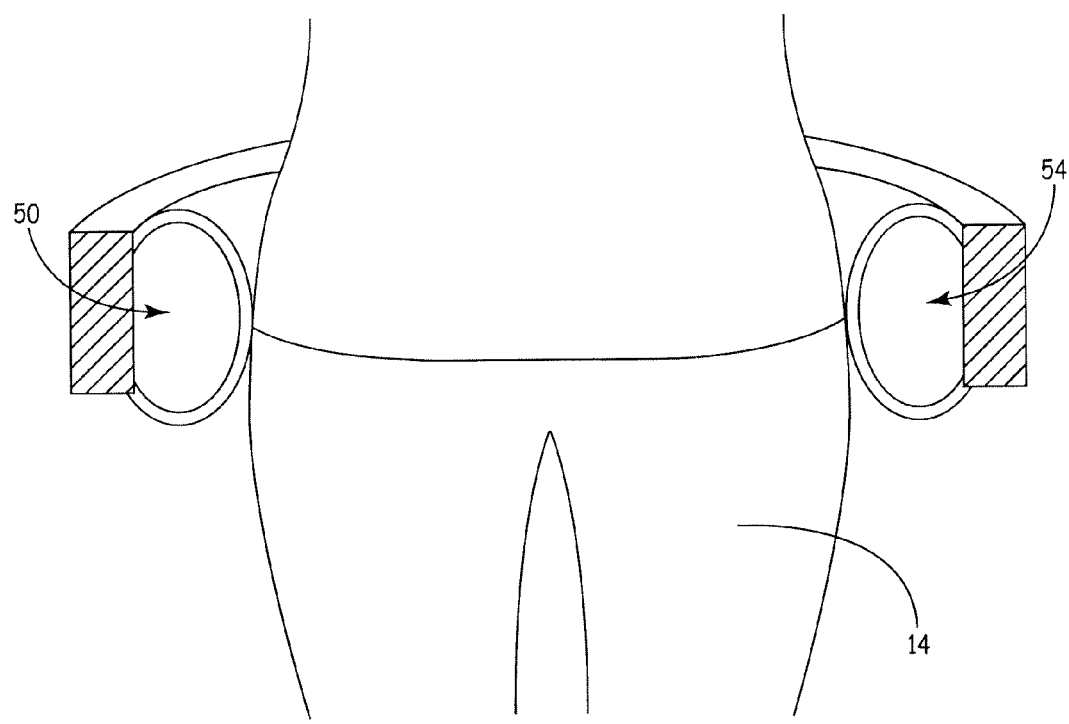
FIG. 8 is a cut-away front view of an inflatable air tube seal for the body suit.

In yet another alternative embodiment, the seal can consist of an inflatable air tube seal 50, as shown in FIG. 8. This inflatable tube seal circumscribes the waist, and is attached via an airtight connection to the exterior of the suit. When inflated with air, the tube seal 50 expands and applies an inwardly directed force to the waist to compress it against the skin to confine the air pressure P condition inside the suit.

Figure 9:
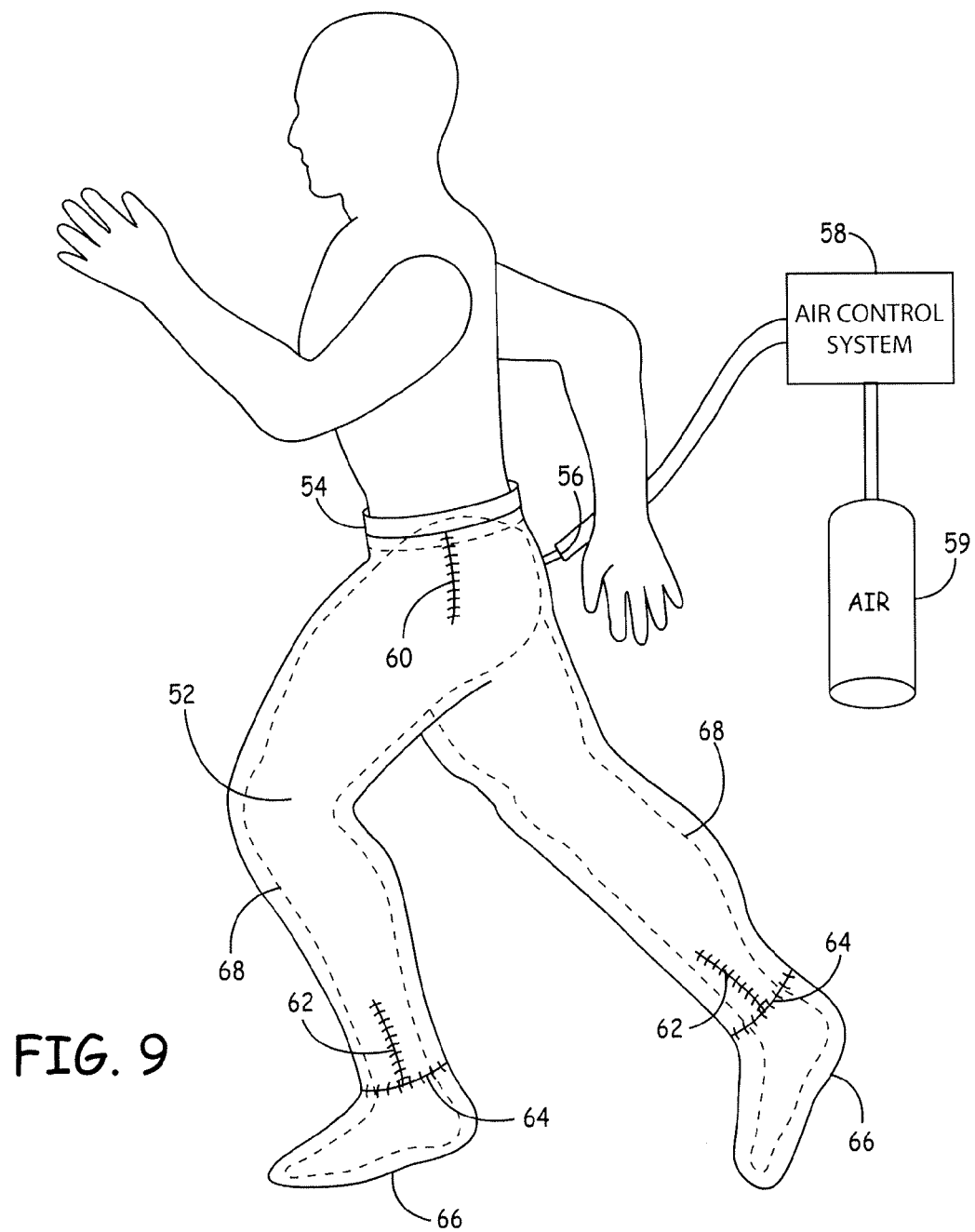
FIG. 9 is a perspective view of a human wearing a full-length pants body suit of the present invention.

As shown in FIG. 9, when suit 14 is pressurized, it maintains a shape close to the body, while affording mobility of the body and limbs. A port 56 is provided in the suit to allow for pressurizing and depressurizing the suit. An air control system 58 connected to an associated pressurized air source 59 maintains the positive pressure condition P inside the suit. The air control system 58 may also control the humidity and temperature levels existing inside the suit. The suit may be statically pressurized once, and then worn by the person without the control system 58. When operating in this manner, the seal 40 maintains the pressure condition for the duration of the time period that the suit is worn. The suit may be worn for time periods ranging between minutes for brief exercises to days for medical rehabilitation.

While this application discusses the use of pressurized air to fill the suit, other pressurized gases may be employed. Other examples of such pressurized gases include nitrogen, carbon dioxide, and argon. Such gases must be non-toxic and not harmful to body skin, or else an inner layer must be worn between the gas and the skin to protect the skin and body.

The differential pressurized suit 52 shown in FIG. 9 comprises a full-length pair of pants which also completely cover the feet. Airtight zippers 60 assist entry into the waist region of the pants. Airtight zippers 62 do the same for ankle regions. Finally, airtight zippers 64 allow the foot portion 66 of the suit 52 to be attached to the pants portion 68 after the feet are inserted through the pant legs.

Figure 10:
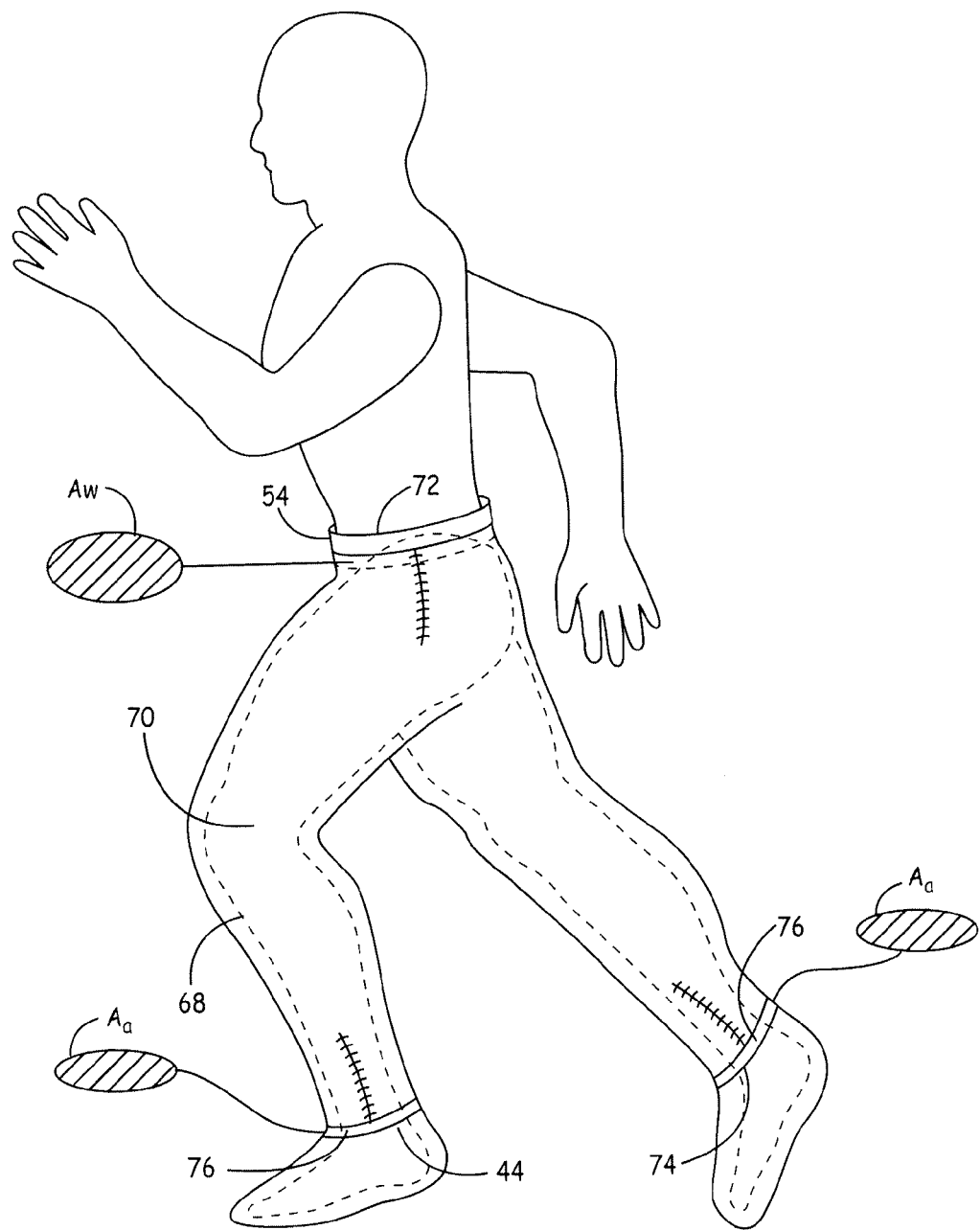
FIG. 10 is a perspective view of a human wearing a pants body suit only extending to the ankles.
Figure 11:
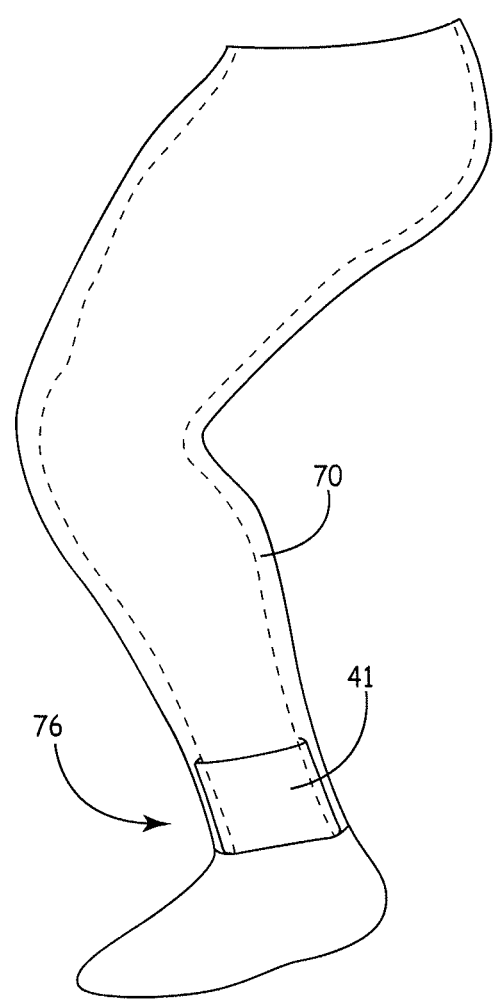
FIG. 11 is a cut-away view of a sleeve seal for the body suit of FIG. 10.

Still another embodiment of a differential pressurize suit 70 is depicted in FIG. 10. In this particular embodiment, the suit extends from the waist 72 to the ankles 74 without covering the feet, and is sealed at the ankle. The waist seal is as described above, and may include a rigid band 54 surrounding an air bladder. The ankle seals 76 are shown in greater detail in FIG. 11, and comprise a sleeve seal 41 connected inside the suit leg 70 that is constructed of elastic neoprene, or another airtight elastic material, such as rubber, latex, or a rubber-coated Lycra. The sleeve seal 41 can be a tight-fitting, airproof neoprene compression sleeve that provides a tight fit over the ankle and lower calf. The sleeve seal 41 should be long enough to provide for a sufficiently airtight closure between the seal and the body skin. The unstretched circumference of the ankle sleeve seal 41 should be less than the circumference of the ankle and lower calf, so that when the sleeve seal 41 is secured around the ankle, a positive pressure is applied by the seal to the underlying skin by the elastic tension of the seals. In this manner, when the suit is pressurized with air to pressure condition P, the pressurized air is substantially contained within the suit 70.

By having suit 70 end at the ankles, motion by the foot will not be impaired by the foot portion of the suit. The suit 70 may also be put on more easily. Moreover, the wearer may wear normal-sized shoes.

The net upward force provided by pressurized air contained within suit 70 may be calculated as:

$$F_b = \Delta P (A_w - 2A_A)$$

where $\Delta P$ is the difference in pressure level P inside the suit and atmospheric pressure $P_{atm}$ outside the suit. $A_w$ is the cross-sectional area of the waist. $A_2$ is the cross-sectional area of each ankle.

Figure 12:
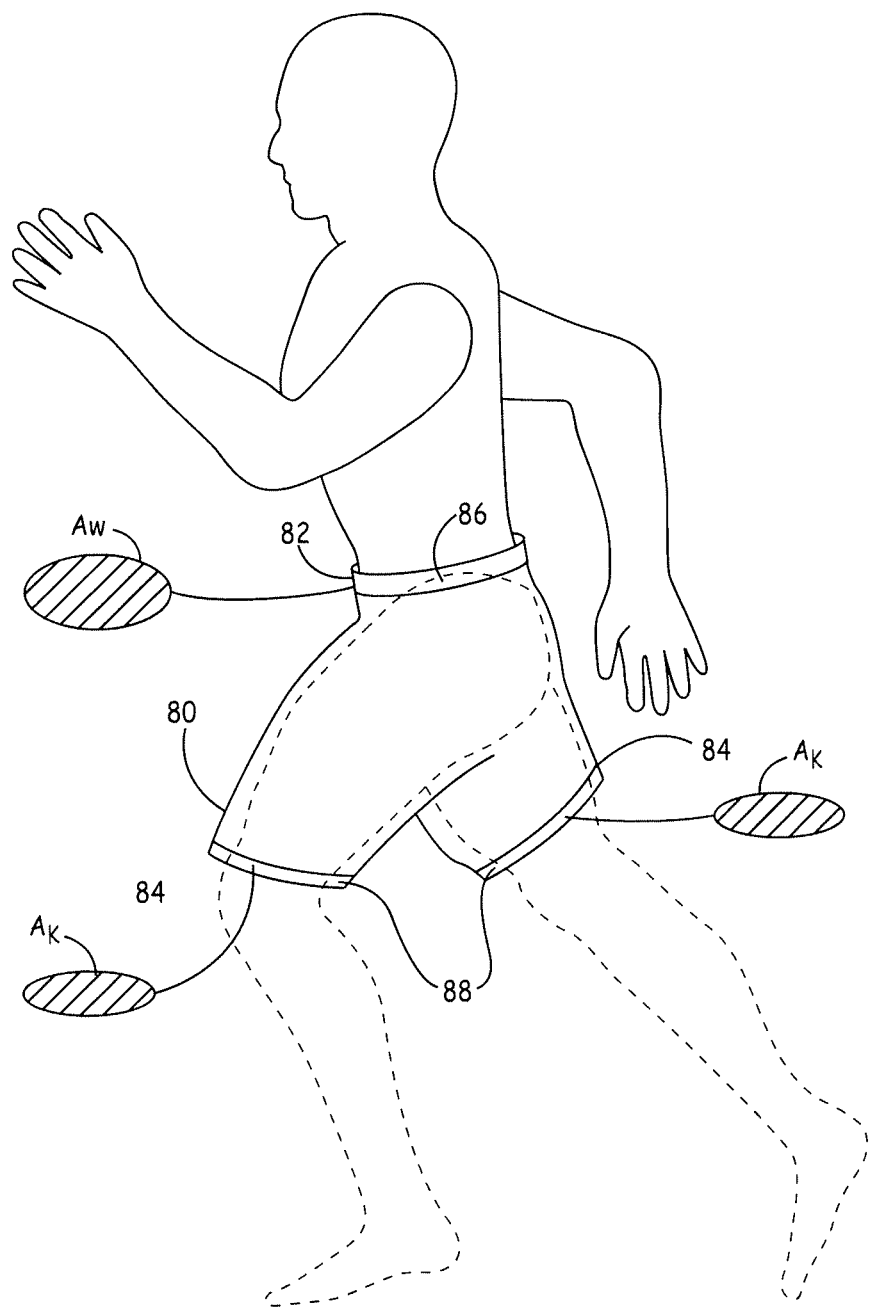
FIG. 12 is a perspective view of a human wearing a pants body suit only extending to just above the knees.
Figure 13:
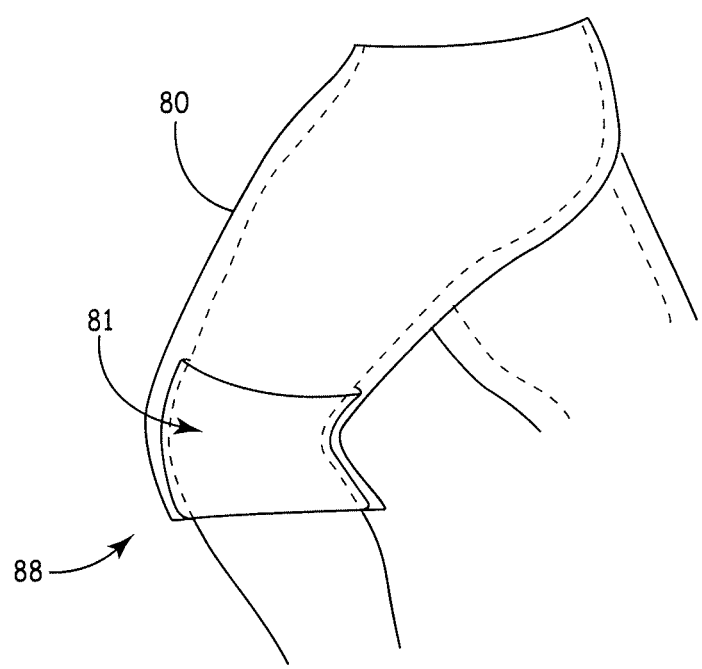
FIG. 13 is a cut-away view of a sleeve seal for the body suit of FIG. 12.

Another embodiment of differential pressurized suit 80 is shown in FIG. 12. In this embodiment, suit 80 extends to just above the knee. It is sealed at the waist 82 and at the knees 84. The waist seal 86 is as describe above. The knee seals 88 are shown in greater detail in FIG. 13. The sleeve seal 81 is an airtight sleeve connected to the interior of the suit 80 that fits tightly over the lower thigh. The sleeve seal should be long enough to provide for a sufficiently airtight closure. The circumference of the knee sleeve seal 81 should be less than the unstretched circumference of the lower thigh, so that when the seal 81 is secured around the knee, a positive pressure is applied by the seal to the underlying skin. This sleeve seal 81 is preferably constructed of elastic neoprene, or any other air-tight material, such as rubber, latex, or rubber-coated Lycra. An advantage provided by this suit 80 is that the runner's knee and lower leg are free to move without any restriction posed by suit 80. This suit 80 is also easier to put on and take off.

The net upwards force supplied to the runner's body when suit 80 is filled with pressurized air is:

$$F_b = \Delta P (A_w - 2A_k)$$

$\Delta P$ is the difference in pressure between pressure condition P contained inside the suit 80 and atmospheric pressure $P_{atm}$ existing outside the suit 80. $A_W$ is the cross-sectional area of the waist. $A_K$ is the cross-sectional area of the spot on each leg just above the knee where seals 88 engage the leg.

Figure 14:
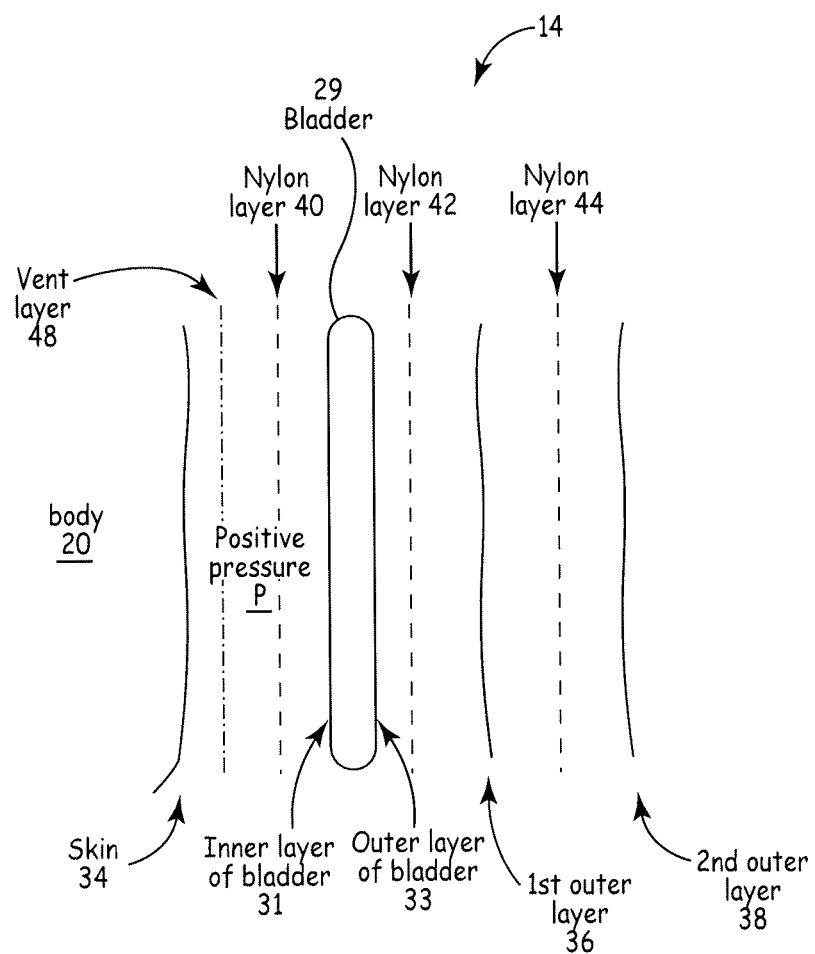
FIG. 14 is a schematic view of the body suit construction further comprising an airtight bladder sealing means.
Figure 15:
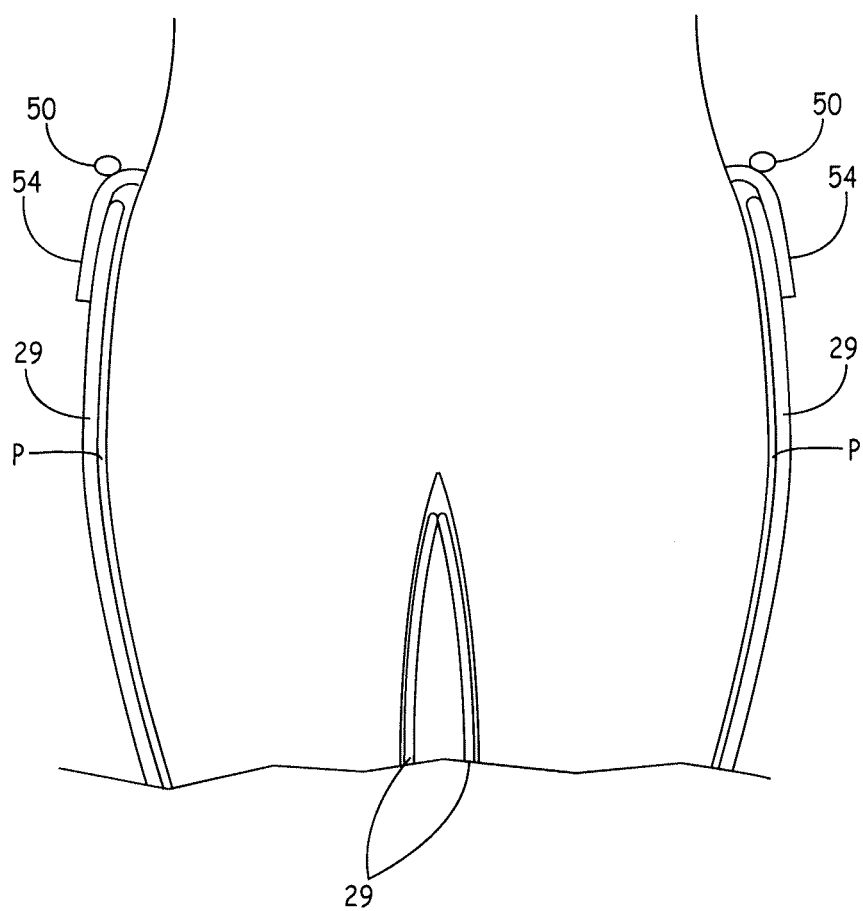
FIG. 15 is a front partial view of the air bladder construction of FIG. 14.
Figure 16:
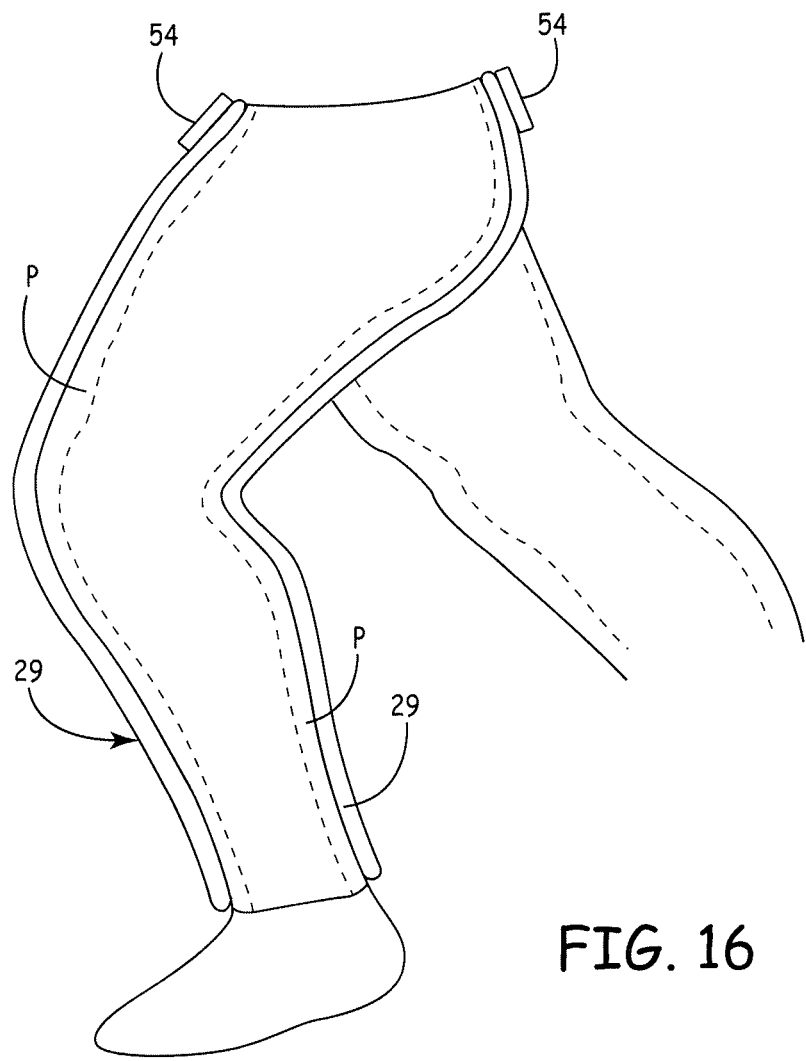
FIG. 16 is a side partial view of the air bladder construction of FIG. 14.

In another embodiment shown in FIG. 14, the pressurized air is contained within the body suit by means of an air-tight bladder 29 illustrated in an expanded view of the layers of the suit. The bladder consists of an airproof inner layer 31 and outer layer 33. The two layers are joined at the top and bottom of the suit to form an air-tight bladder. This bladder is essentially two identical air-proof layers, nested one inside the other, and sealed together at the top waist area and bottom of each leg of the suit. When pressurized, the inner layer presses against the skin and the outer layer presses against the outer constraining layers 36 and 38. A frontal view of the bladder 29 is shown in FIG. 15. A side view of the bladder is shown in FIG. 16. The bladder 29 contains air at pressure condition P. The bladder may be used for the various embodiments of the pressure suits described herein, including a bladder that extends from the waist to around the foot, a bladder that extends from the waist to the ankle, and a bladder that extends from the waist to above the knee.

Figure 17:
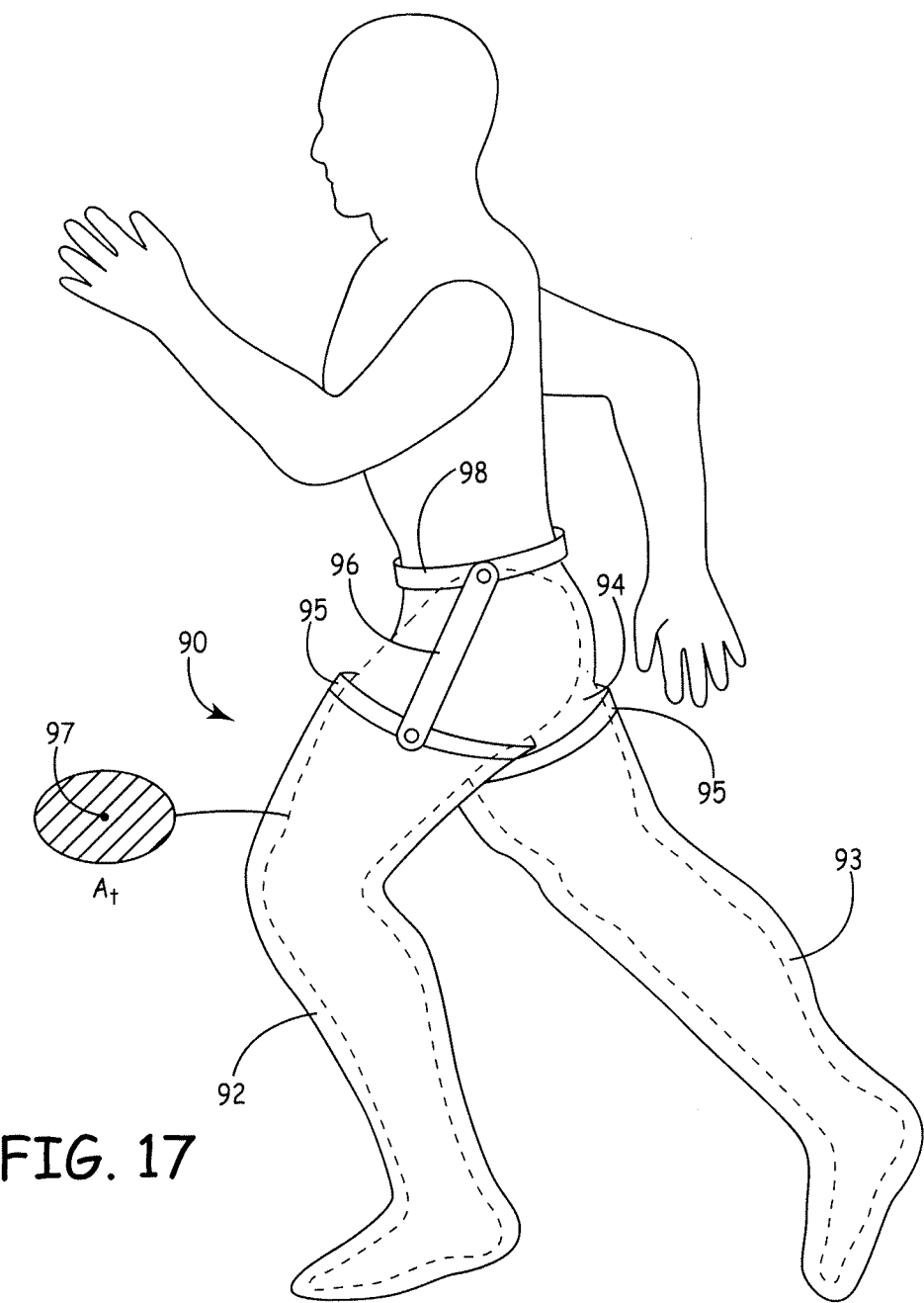
FIG. 17 is a perspective view of an alternative embodiment of the body suit comprising separate pressurized leg units.

Yet another embodiment is shown in FIG. 17 of differential pressurized suit 90. This embodiment consists of an independent suit 92 and 93 for each leg, having leg openings 94 near the upper thigh. The upper thigh seals 95 can extend diagonally from the upper thigh at the groin on the inner side of the leg to the hip on the outer side of the leg. $A_t$ is the cross-sectional area of the spot on each leg at the upper thigh where seals 95 engage the leg.

Each leg suit 92, 93 covers the entire lower leg and foot, so that the entire leg below the thigh seal 95 is airtight. The leg suits are attached by means of straps 96 to a rigid band 98 that is provided near the waist. This band may alternatively constitute a strong, flexible fabric. The band 98 is then attached to a supporting structure (not shown). Alternatively, the leg suits may be attached directly to the support frame by means of straps 96. The positive pressure differential $\Delta P$ contained in the leg suits 92, 93 results in an upwards-directed resultant force $F_b$ applied to the body located at the centroid 97 of the cross-sectional area $A_t$. The total amount of this upwards force $F_b$ on the body from both leg suits is:

$$F_b = 2\Delta P \times A_t$$

where $\Delta P$ is the difference in pressure between the positive pressure P condition inside the suit and atmospheric pressure $P_{atm}$ outside the suit. $A_w$ is the cross-sectional area of the waist region. $A_t$ is the cross-sectional area of each upper thigh region.

The various configurations of suits described above provide high to lower amounts of upwards force $F_b$ on the body, depending upon the location of the seals. The complete lower body coverage suit 14 of FIG. 1 provides the greatest upper lift to the body, because:

$$F_b = \Delta P \times A_w.$$

The waist-to-ankle suit 70 of FIG. 10 provides the next largest amount of lift, because:

$$F_b = \Delta P (A_w - 2A_a).$$

Next in decreasing progression is the waist-to-just-above-the-knee suit 80 of FIG. 12, because:

$$F_b = \Delta P (A_w - 2A_k).$$

For most humans, their body anatomy is such that $A_a < A_K$. The independent leg suits 92, 93 also provide for a higher to lower amount of upwards force on the body. The leg suit with a top seal at the upper thigh of FIG. 17 provides the highest amount:

$$F_b = 2\Delta P \times A_t$$

A leg suit with a top seal at the upper thigh and a bottom seal at the ankle (not shown) provides the next highest amount:

$$F_b = 2\Delta P \times (A_t - A_a)$$

A leg suit with a top seal at the upper thigh and a bottom seal at the spot above the knee (not shown) provides the lowest amount:

$$F_b = 2\Delta P \times (A_t - A_k)$$

Figure 18:
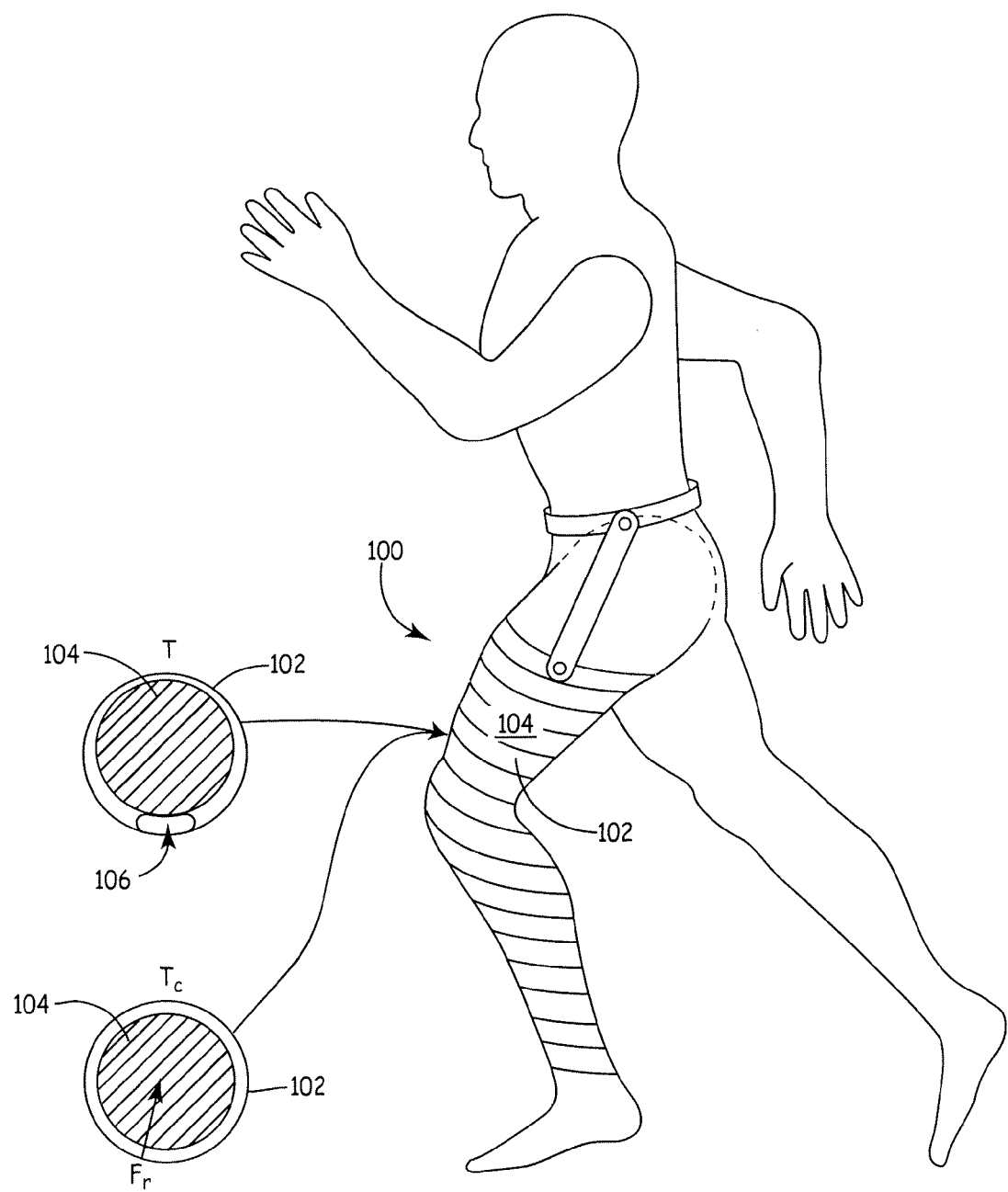
FIG. 18 is a partial perspective view of an alternative embodiment of the body suit comprising a circumferential tension system.

While pressurized gases like air have been discussed as the pressurizing medium for the differential pressurized suit 14 of this invention, positive pressure applied against a body and its limbs can be created by other means. For example a fabric or elastic material 102 circumferentially kept under tension around a leg 104 can be employed, as depicted in FIG. 18. The material 102 exerts a tension $T_c$ that creates an inwardly-directed radial force $F_r$ on the body that is normal to the surface of the leg. The effect of this force within this circumferential tension system 100 is similar to the effect of positive pressure developed by air pressure—i.e., a net upwards force is created on the body.

Various means can be utilized to develop this tension. For example, an elastic material can provide this circumferential tension. In such example, the "suit" is constructed by a multitude of windings of an elastic material that is perpendicular in direction to the axis of the leg 104, and non-extensional in the longitudinal direction of the leg. The suit is sized to be smaller than the body, so that a tension is developed when the suit is put on. Alternatively, the suit can be placed under tension through the use of zippers, or by cinching up the suit via lacing, tied in a knot after it is put on. Suits of this circumferential tension embodiment 100 may be similar in degree of coverage, as discussed above—e.g., waist-to-above-the-knee, waist-to-ankle, waist-to-around-foot; upper thigh/hip-to-above-knee; upper thigh/hip-to-above-ankle; upper thigh/hip-to-around-foot.

An air bladder 106 positioned under a portion of the wrap 102 against the leg 104 may be utilized to create further tension inside the suit 100. This air bladder should have a small width, and extend longitudinally along the body under the wrap 102. When the bladder 106 is inflated with a gas like pressurized air, the wrap 102 is placed under tension. Advantageously, only a small amount of air is required to create the positive pressure on the body, because the wrap 102, itself, also contributes positive pressure via the tension. At the same time, the wrap material can allow for breathe-ability and the transfer of moisture away from the body.

Shaped memory alloys like nickel titanium or shaped polymers may likewise be used to provide the tension in a circumferentially-tensioned pressure suit. An electric current can be applied to cause the material to change in shape to conform to the underlying body's shape, and create circumferential tension. Shaped memory alloys or polymers can be woven into fabric that the suit is constructed of.

Figure 19:
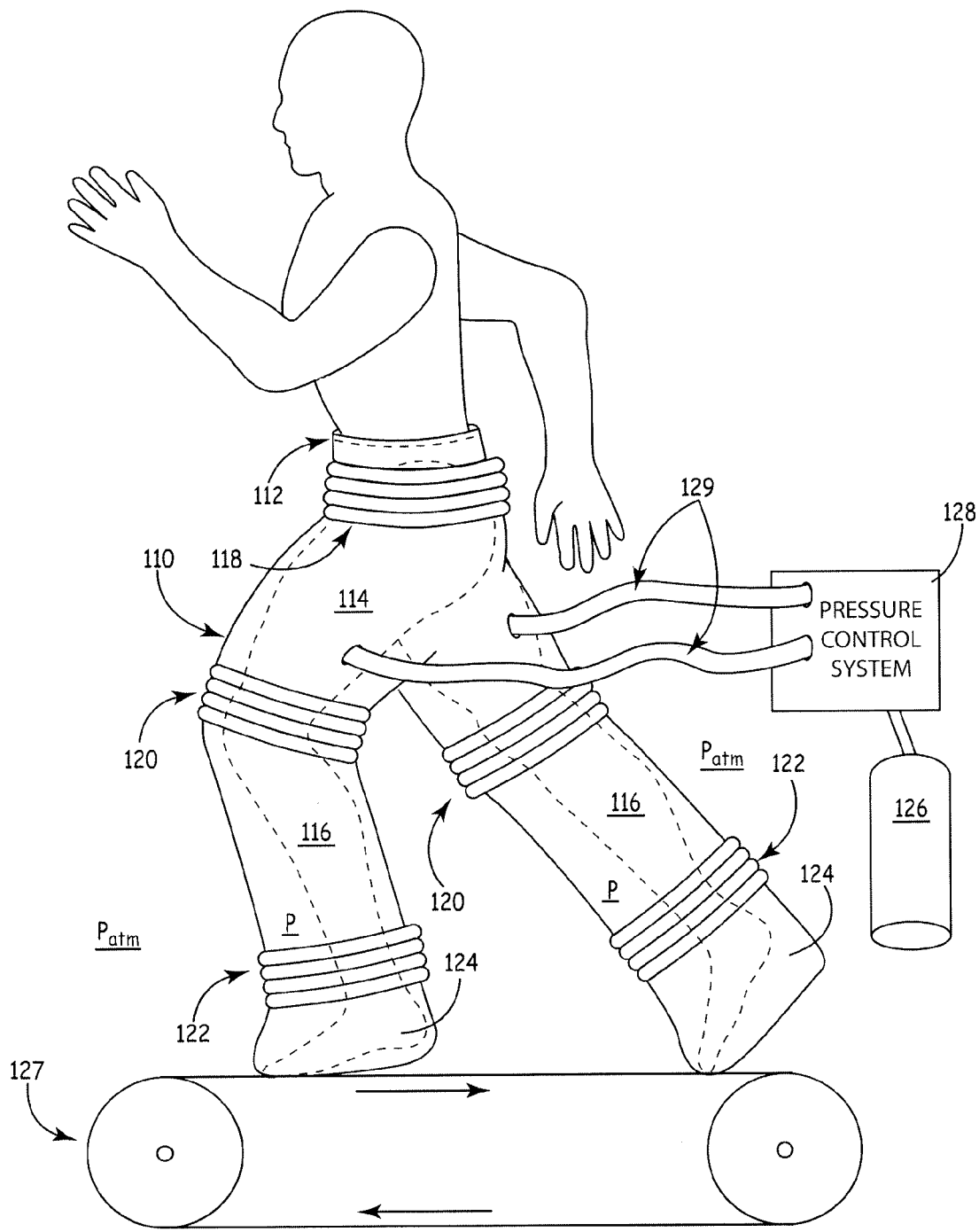
FIG. 19 is a perspective view of an alternative embodiment of the body suit comprising a loose-fitting body suit.

While close fitting differential pressure suits 14 and circumferentially-tensioned suits 100 have been described for use with the assisted motion system 10 of the present invention, a looser-fitting suit 110 may also be employed, as shown in FIG. 19. The legs of the suit 110 may extend downwardly to just above the knee, above the ankle, or cover the entire foot, as described above. Seals 112 can be provided around the waist and at the bottom edges of the suit if the suit does not extend around the feet. Exemplary locations include: upper seals 112 at the waist or upper-thigh-to-hip; lower seals at above the knee or above the ankle.

Mobility of the body 114 and lower legs 116 is provided by constant volume joints positioned at the waist 118, knee 120, and ankles 122, respectively, of the suit 110. The equation for work where volume is changed under a constant pressure is:

$$W = P \times \Delta V$$

where W is work, P is the constant pressure, and $\Delta V$ is the change in volume. Clearly, holding the volume constant in a joint, such that $\Delta V=0$ over the course of joint flexure is one way to nullify the need to expand work just to flex the suit joint.

A constant-volume joint allows the cross-sectional area of the joint of the suit to maintain a constant volume of pressurized air P during bending of the body, so that the work, and thus the force, required to bend the joint is minimized. In the preferred embodiment of loose-fitting differential pressure suit 110, the constant volume joints consist of baffles and tensioning straps along the sides of the joint to prevent the baffles from extending. Other types of constant-volume joints known in the prior art, such as "Space Suit Mobility Joints described in U.S. Pat. No. 4,151,612, and which is hereby incorporated by reference in its entirety, may also be utilized. The suit shown in FIG. 19 has constant volume joints positioned at the waist-through-the-hip section and at the knee. A constant volume joint at the knee 120 allows the leg to bend and move at the knee with the motion of walking or running without the need for undue force. An airproof boot 124 is worn and the constant volume joint 122 is utilized to allow for mobility.

Pressurized gas 126, such as air, is injected into the suit 110 by means of control system 128 and hoses 129. A person wearing the suit 110 may exercise on a treadmill 127, but portable pressurized gas systems are also possible.

A rubberized nylon can be utilized to construct a single-layer suit. This can be sewn into the appropriate shape using a standard sewing machine. Thigh seals can be made from a commercially-purchased neoprene compression sleeve. Compression sleeves are available from Advanced Brace of Irving, Tex. Neoprene compression shorts are available from the same supplier. The compression sleeve can be sewn interior to the pant around the thigh opening, and made airtight with seam sealer in the form of Seam Lock sold by REI, Inc. of Sumner, Wash. to make the seam airtight. A shorts-type waist seal can be constructed by sewing the waist area to the outer rubberized nylon suit, and sealing the seams to make it airtight. Alternatively, a compression sleeve may be connected to the rubberized nylon exterior suit, by placing each over an appropriate diameter steel band, and then clamping together the two layers of material with another outer ring. A standard air intake fitting can be installed in the pants to provide a port for pressurizing the suit.

Another important aspect of the assisted motion system 10 of FIG. 1 is the external support structure 26 that is necessary for preventing the downwardly directed force $F_s$ on the suit created by the positive pressure differential $\Delta P$, from forcing the suit down and off the runner's body. In the case of FIG. 1, the embodiment of external support structure 26 constitutes a frame 28 and wheels 30 for providing complete mobility to runner 12. Such support structures should be designed for the specific range of body motions that the person wearing the suit plans to carry out.

Figure 20:
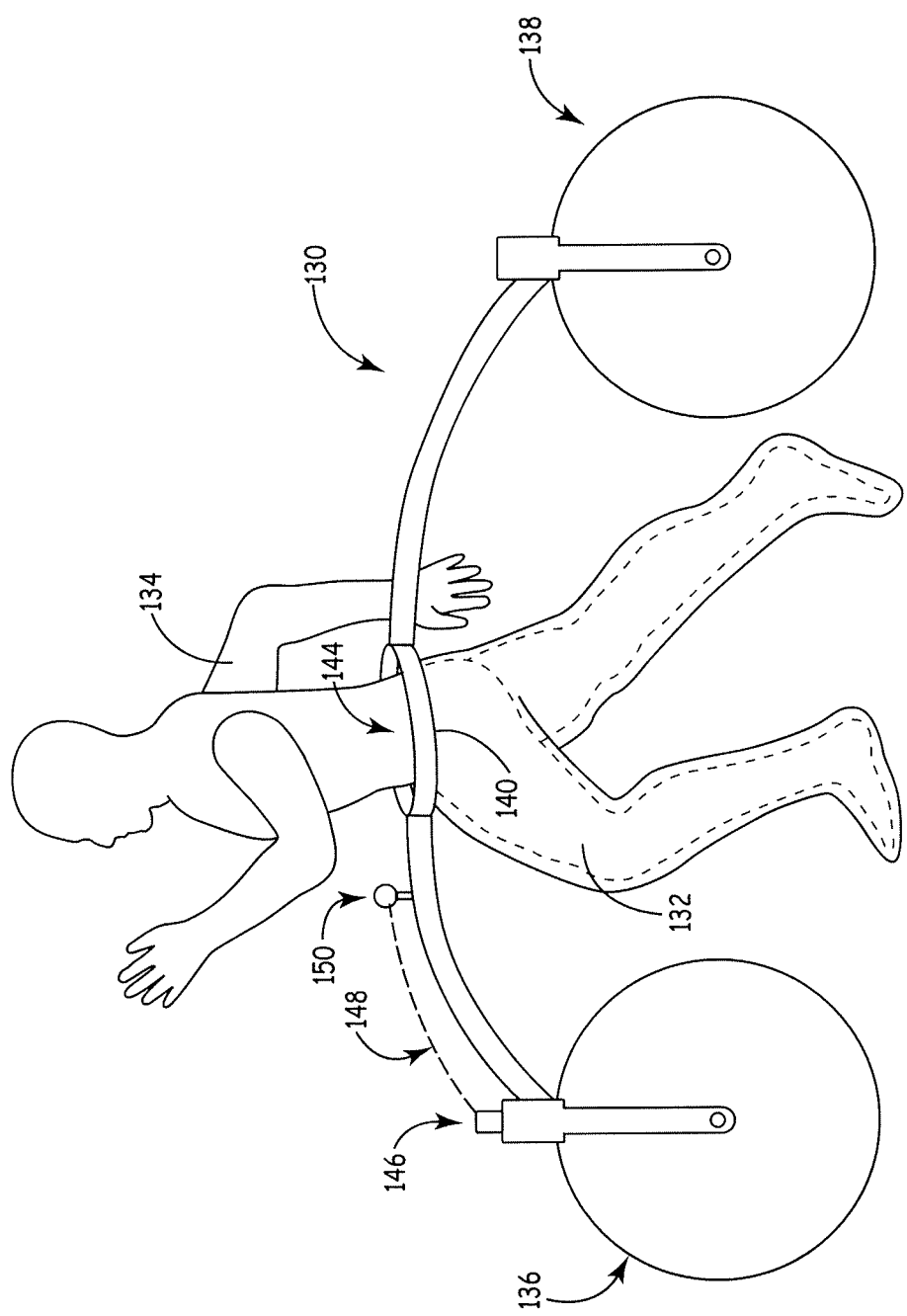
FIG. 20 is a perspective view of an external wheeled frame support structure for the body suit.

Shown in greater detail in FIG. 20 is a wheeled frame structure 130 for supporting a differential pressurized suit 132 worn by a runner 134 who is running. As the runner wears this suit 132 supported by the wheeled frame 130 during his running routine, he experiences less weight on his feet, knees, legs, and lower body, because a portion of his body weight has been offloaded by the upwards force $F_b$ on the body created by the positive pressure differential $\Delta P$ of the pressurized suit 132. The downward force $F_s$ on the suit also caused by the positive pressure differential $\Delta P$ is transmitted to the support structure 130, and from the support structure to the ground.

The wheeled frame structure 130 shown in FIG. 20 has a construction similar to a bicycle: a wheel in the front 136 and one in the back 138. The runner 134 is positioned midway between the wheels, and the space between the wheels is sufficient to avoid contact with the runner's legs. The rotational momentum of the wheels stabilizes the frame during motion, as with a bicycle. The wheeled frame structure 130 wraps around the runner 134 at the waist/hip level. Note the absence of a seat, pedals, sprocket and chain that are normal to a bicycle. The frame 130 is designed so that the runner 134 can swing his arms and hands when running.

The pressurized suit 132, as described in other embodiments of this invention, will create a force along the vertical axis of pushing the body up, with the reaction force being that of pushing the suit down. The latter is countered in this embodiment by offloading this downward reaction force to the 'bike' wheeled frame structure 130, thereby effectively delivering part of the runner's weight to the bike frame and thus to the ground through the wheels.

A mechanism 144 allows for both rotational and angular pivoting of the runner's torso during the motion of running. In this embodiment, the mechanism simply consists of a flexible pleated material 140 surrounding the region about the waist of the pressure suit, which may bend and twist with the movement of the runner's torso. Other mechanical mechanisms for this purpose may also be utilized.

The wheeled frame structure 130 has a mechanism 146 for steering the bike. In one embodiment of the steering mechanism, the movable front wheel 136 is steered in a similar fashion to a bicycle, except instead of long handlebars, cables 148 and a small steering wheel 150 are used employing well-known mechanical methods to implement steering. In a second embodiment of the steering mechanism, a handlebar is brought back in reach of one or both arms of the runner. The only difference in this embodiment and a standard bicycle steering mechanism is that a centering spring holds the bike true, or non-turning until the runner applies force to the steering handle bar. This allows periods of running without active steering. A third steering embodiment uses a stepper motor in the steering column powered by an embedded rechargeable battery. The steering is controlled by the motor via a wireless handheld glove actuator that provides motion commands to the motor using well-known wireless and motion control methods. This permits the runner to freely swing his arms in a natural running motion, and still retain full-time steering control. A fourth steering embodiment positions the hub of the wheel backwards or forwards of the vertical axis of steering to provide automatic steering.

The wheeled frame structure 130 may also have standard bicycle brakes which are operated by a hand lever using well-known means, or by the handheld remote control method that may actuate electric powered brakes.

An optional constant force extension mechanism may be used that provides a constant upwards force on the pressure suit allowing it to move vertically with the vertical motion of the runner's body. The constant force of the mechanism is adjustable so that the upwards force on the mechanism is equal to the downwards force of the suit under pressure. The suit can thus float vertically up and down with the motion of the runner's torso, while maintaining an essentially constant upward force on the suit. A range of motion of 0-7 inches is provided to accommodate various runners, with 3 to 4 inches being a typical vertical displacement in running motion.

Different frames sizes may be provided to fit different sized runners. The vertical position of the rotational and angular pivoting mechanisms and the constant force may be adjustable to accommodate different body heights.

Figure 21:
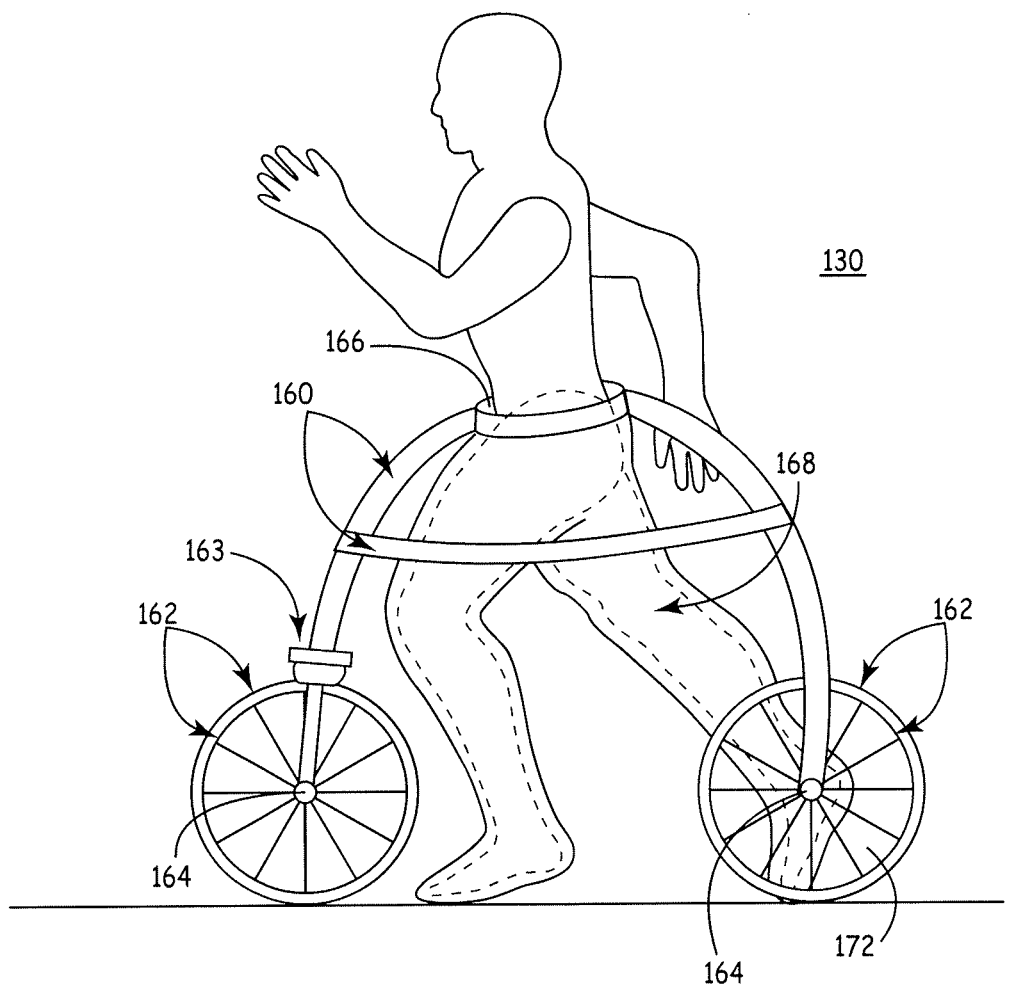
FIG. 21 is a perspective view of an external cart-like support structure for the body suit.

An alternative embodiment to the foregoing bicycle-like running support structure 130 is a cart-like structure with four wheels, arranged as pairs of wheels lateral to the left and right sides of the runner, as shown in FIG. 21. In this embodiment, the wheel frame structure 160 is connected to each wheel 162 lateral to the runner, leaving a clear path to the front and back of the runner. The front wheels operate independently and are implemented as turnable castors 163 to accommodate steering. The rear wheels also rotate independently, but are fixed on their vertical axis. The axle shafts 164 provide a rigid connection to the interface member 166 for the pressure suit 168. In a manner identical to the bicycle-like embodiment, a portion of the runner's weight is off-loaded via the pressure suit 168, and transmitted to the frame, axle shafts 164, and ultimately the ground 172. Steering is accomplished passively in that the cart simply follows direction changes engendered by the runner's change in direction, which translates twist through the frame to the front wheel castor mechanisms in a manner similar to steering a shopping cart.

Yet another embodiment may be that of a tricycle, where a pair of wheels front-left and front-right of the runner are connected to the frame as in the four-wheeled cart, and a third free wheel and a single free turning rear wheel confers stability to the system. Finally, it should be realized that any number of wheels may be used without departing from the scope of this invention.

Figure 22:
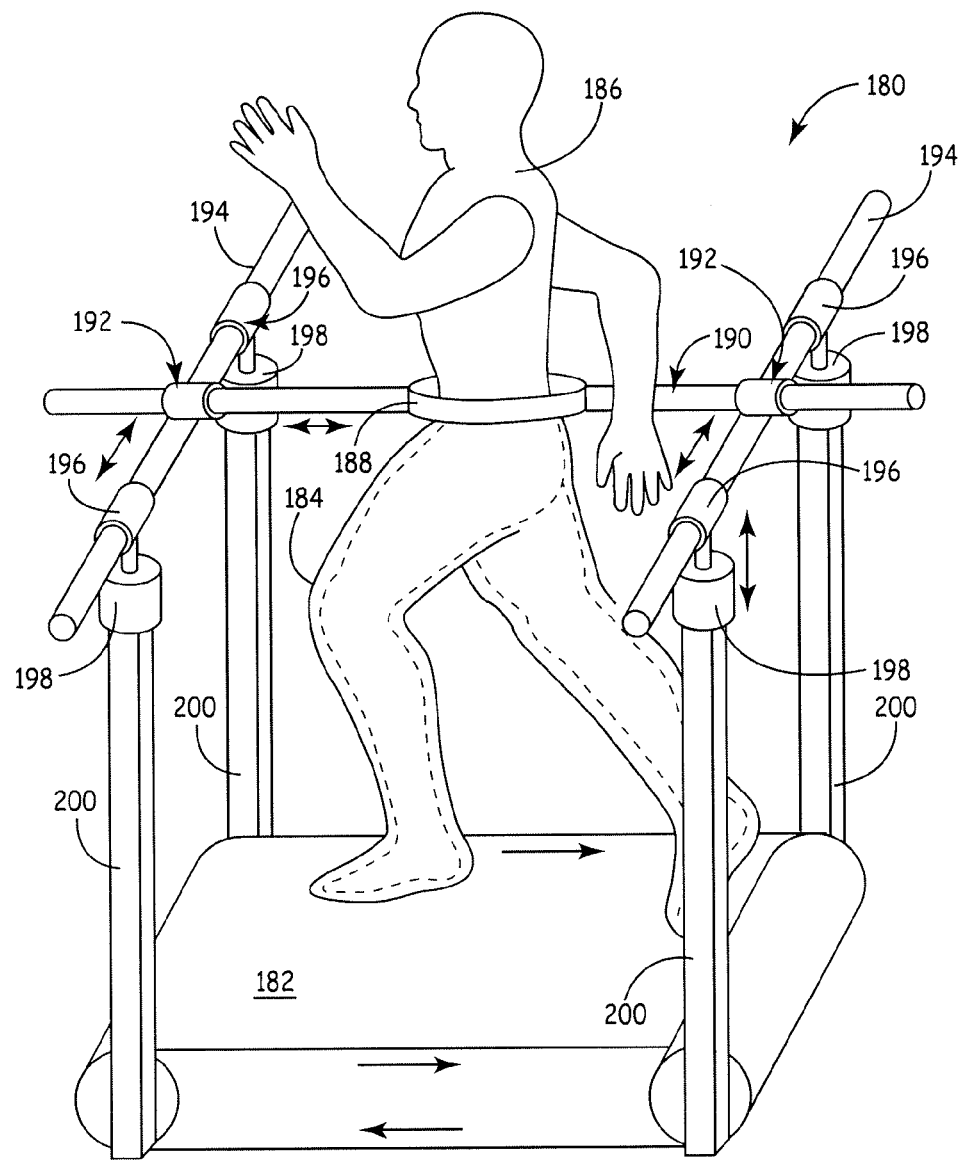
FIG. 22 is a perspective view of a stationary support frame structure for the body suit.

FIG. 22 shows another embodiment of the support structure consisting of a stationary supporting frame 180 positioned over a treadmill 182. The frame 180 provides support for the pressure suit 184 worn by the runner 186. Any of the aforementioned pressure suit embodiments may be utilized for this static support structure 180. For illustrative purposes, FIG. 22 depicts a pressure suit 184 that ends above the ankles. Conceptually, the only difference between this static support structure 180 and the aforementioned wheeled frame structures 130 and 160 is that the reaction force that is subtracted from the runner's weight is offloaded from the runner to a rigid fixed structure, the treadmill frame, instead of a mobile structure.

This is accomplished by providing a set of sliding rods which support the runner and are arranged to allow for longitudinal and lateral motion. A rigid waist loop supporting member 188 wraps around the runner's body and connects to the pressure suit 184 at the waist. A horizontal longitudinal sliding rod 190 connects to each end of the frame and slides through the fittings 192. The sliding longitudinal rod allows for longitudinal movement of the runner in the front to back direction on the treadmill 182. The fittings 192 are attached at the middle of each of two horizontally-disposed, sliding lateral rods 194. These sliding lateral rods allow for lateral movement of the runner on the track in the side-to-side direction. The lateral sliding rods 194 slide through fittings 196 that are fixed atop adjustment mechanisms 198. These adjustment mechanisms provide a counter-force to support the vertical downwards loads from the suit and sliding rods, while allowing for the vertical motions of the runner 186. Preferably, these adjustment mechanisms are air cylinders. They also preferably provide constant force. In other embodiments, adjustment mechanisms may be air springs or constant-force mechanical springs, as is known in the art. The adjustment mechanisms may also be mechanical springs or air cylinders or air springs that are not constant force. The springs are connected to vertical rigid members 200 that connect to the base of the treadmill.

In usage, the adjustment mechanisms are each set such that the total force equals the desired weight to be subtracted. Air cylinders are available from Bimba Manufacturing Company of Monee, Ill. Prior to pressurizing the suit 184, the runner steps up on a small support about one foot above the surface of the treadmill, and clips into the hooks on the air cylinder apparatus. Once this is done, the suit 184 may be pressurized. By standing on a scale, the pressure may be set to subtract the desired weight. Alternatively, since the pants characteristics should be known a priori, a specific calculated pressure P applied to the suit 184 will yield a specific weight subtraction. The desired weight subtraction set via the pressure P, and the counter force supplied by the adjustment mechanisms 198 can be approximately matched. A control system can control the adjustment mechanisms 198 to provide the correct counter-force. During running, a runner could move vertically from 1 to 7 inches, typically 3 or 4 inches, vertically relative to the running surface. The function of the adjustment mechanisms 198 is to maintain a constant offloading of the reaction force dynamically, in response to this vertical displacement during running.

Figure 23:
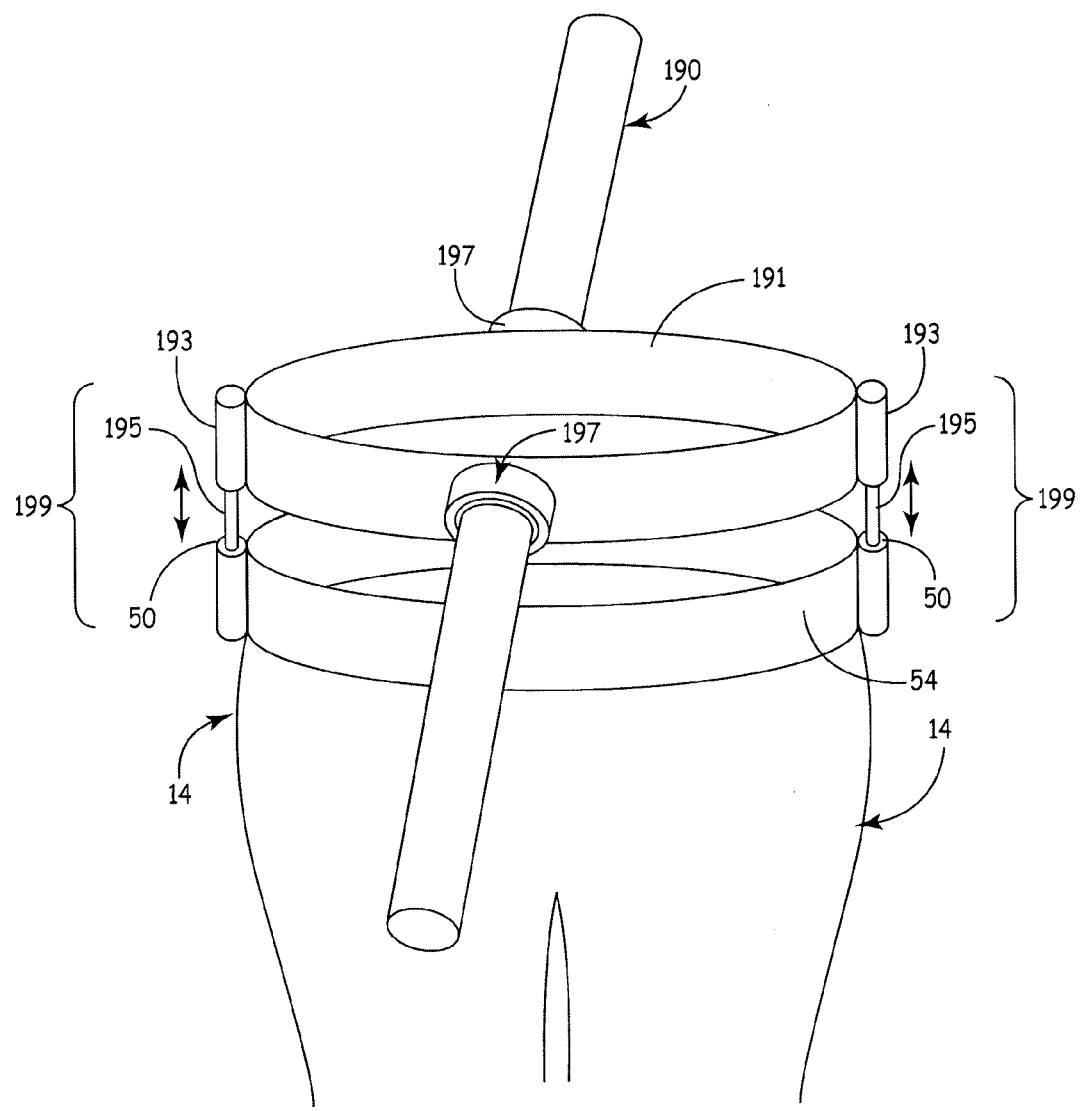
FIG. 23 is a partial perspective view of a constant-force adjustment mechanism for the stationary support frame structure of FIG. 22.

Another embodiment of a constant force adjustment mechanism is shown in FIG. 23. An upper supporting ring structure 191 is connected to the central supporting structure 190 via a connection fixture 197. An air cylinder actuator 199 is attached to each side of the supporting ring 191. Air cylinder actuators are available from Bimba Manufacturing Company of Monee, Ill. The air cylinder actuator 199 consists of a cylinder 193 and a piston rod 195. The piston rod of the air cylinder actuator is attached to the waist band 54 of the suit at the connecting eye 50. A control system can apply the correct calculated pressure to the air cylinder actuators. This adjustment system may also be employed on the various supporting frames described herein.

In contrast to large stationary pressure chambers known in prior art, a significant advantage in this static support structure 180 is that it allows both lateral and longitudinal movement of the runner relative to the treadmill track. Another advantage over large pressure chambers is that the runner's arms can swing freely.

The motion assistance system of the present invention can also be used to help bicycle riders minimize the effect of erectile dysfunction or numbness caused by the pressure of the bicycle seat horn on the groin region. Embodiment 210 of the invention shown in FIG. 24 reduces the contact pressure between a bicycle rider 212 and the seat 214. This embodiment utilizes air pressure contained within a pressurized suit 216 to apply an upward force on the bicycle rider to reduce or eliminate contact pressure between the rider and the seat. The air pressure applies an evenly distributed pressure on the pressurized suit 216 and lower body of the rider, which lifts the body to reduce the contact pressure between the rider and the seat.

The bicycle 218, itself, is utilized as the supporting structure to support the downwards force of the pressure suit. The bicycle seat 214 provides a support point for the pressure suit. The pressure suit 216 is modified to attach to the bicycle seat and prevent the suit from moving down the body due to downwardly directed force $F_s$ on the suit created by the positive pressure differential $\Delta P$. A reinforced rigid structure is incorporated into the pressure suit 216 to attach to the bicycle seat. The attachment allows for easy connection and disconnection as the rider mounts and dismounts the bicycle.

Figure 27:
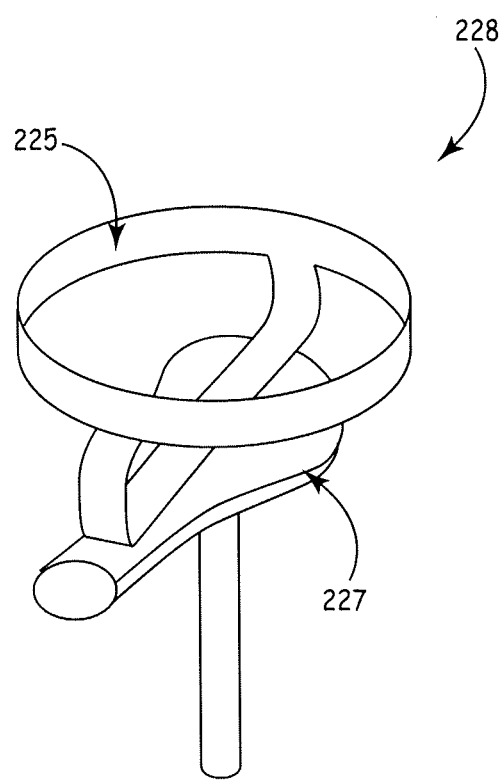
FIG. 27 is a perspective view of the support structure shown in FIGS. 24-26.

As shown more clearly in FIG. 27, the rigid structure 228 has a band 225 that extends around the rider's waist. Another rigid band 227 from the back of the rider and through the crotch to connect to the front section. The bottom crotch section 226 is shaped to conform to the rider's anatomy and the surface of the bicycle seat.

Figure 24:
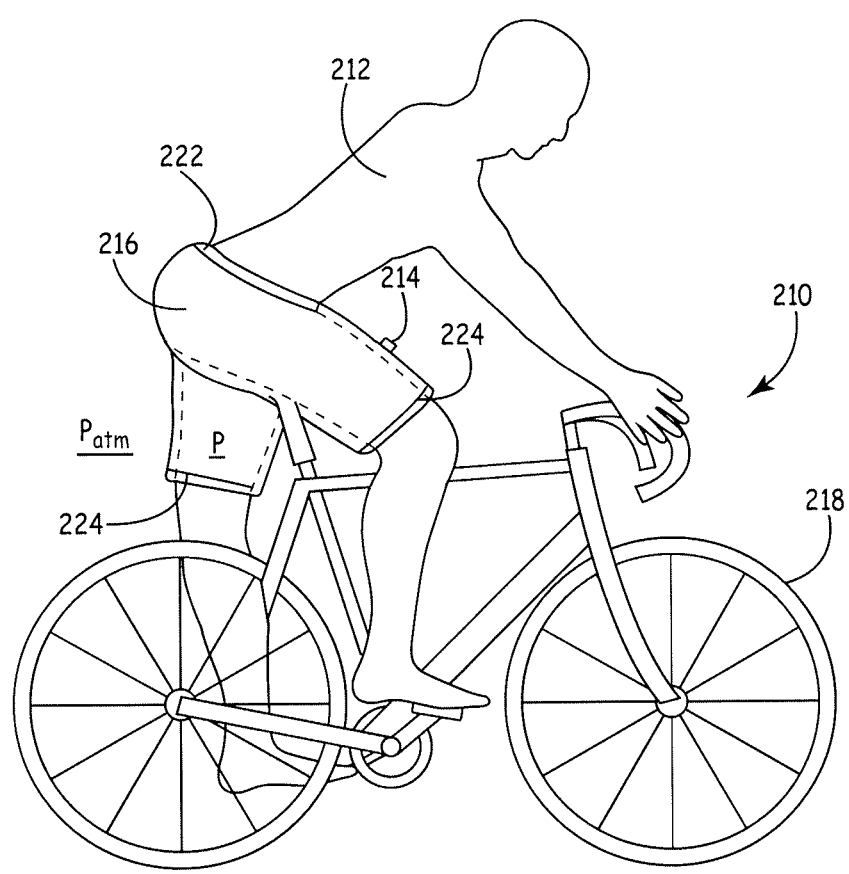
FIG. 24 is a perspective view of an assisted motion system of the present invention for bicycle riders.

FIG. 24 shows a side profile of a bicycle rider wearing the pressurized trunks. The pressurized suit 216 is utilized to subject the lower portion of the rider's body, below the waist and the upper legs to a pressure P greater than atmospheric pressure $P_{atm}$. The close-fitting pressure suit 216 is constructed of layers of materials which maintain the pressure and prevent the suit from expanding circumferentially or longitudinally. The pressure suit has an airtight seal 222 against the body at the waist. The suit extends to above the knees. Alternatively, the pressure suit may extend to the ankles or around the foot. The bottoms of the legs of the pressure suit have airtight seals 224 against the legs above the knees. In an alternative embodiment, the suit may have a pleated portion at the hip joints similar to the design of constant volume joints in the loose-fitting pressure suit. The pleated joint includes a tension strap on the rider's side from the waist to the lower part of the leg of the suit which prevents the pleats from fully expanding when the suit is pressurized.

The suit is pressurized to pressure P which is greater than atmospheric pressure, thereby creating a positive pressure differential $\Delta P$ in the suit. The positive pressure differential $\Delta P$ results in an upwards-directed resultant force $F_b$ on the body located at the centroid of the cross-sectional area $A_w$ of the waist. $A_k$ is the cross-sectional area of the spot on each leg just above the knee where seals 88 engage the leg. The force on the body $F_b$ is approximately the same as the force of the waist-to-just-above-the-knee suit 80 of FIG. 12. The amount of this upwards force $F_b$ is:

$$F_b = \Delta P \times (A_w - 2A_k).$$

Alternatively, the bicycle pressure suit embodiment may also incorporate an inner airbladder (as previously described) to contain the air pressure, as a seal. The air bladder is made from a flexible material such as neoprene and roughly the same shape as the bicycle pressure suit. Another form of an air bladder is made from two sets of similar shaped airtight pressure suits, one inside the other and sealed to each other at the waist and legs.

Figure 25:
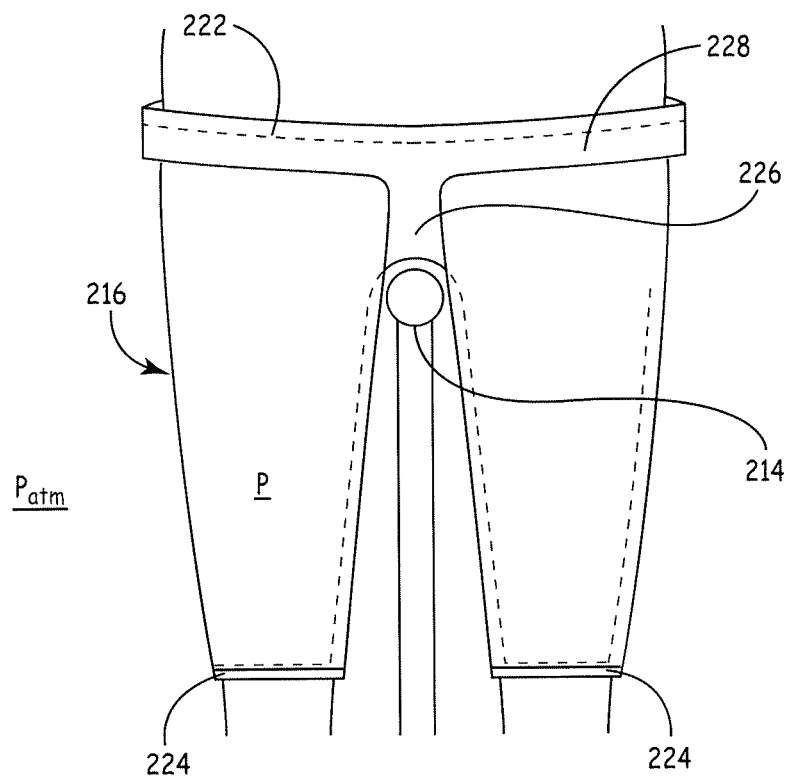
FIG. 25 is a front view of the support structure for the bicycle assisted motion system of FIG. 24.
Figure 26:
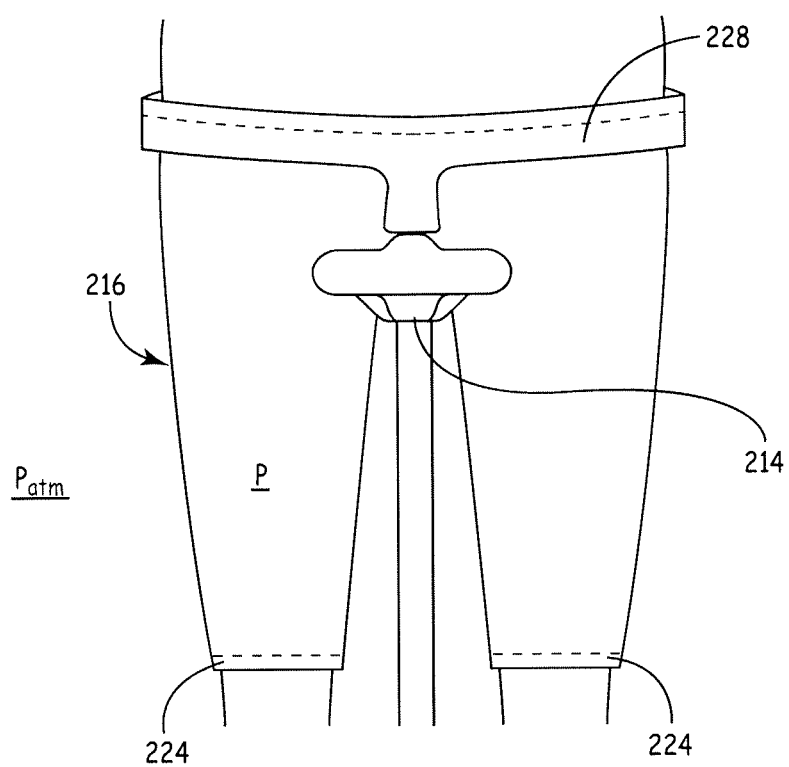
FIG. 26 is a back view of the support structure for the bicycle assisted motion system of FIG. 24.

FIG. 25 shows a front view of the bicycle pressure suit. FIG. 26 shows a rear view of the pressure suit. FIG. 27 shows a perspective view of the supporting structure of the bicycle pressure suit. The suit has a rigid structure 228 that fits snugly onto the bicycle seat 214. The structure may be an exoskeleton (i.e. a structure outside the suit), or an airtight rigid portion that is part of the airtight suit. The exoskeleton extends around the side of the body at the waist, and extends through the crotch and around the back side of the rider to join the frontal structure at the waist at the rider's side. The rigid structure is capable of supporting the downward load $F_s$ on the suit created by the differential pressure $\Delta P$. The structure is attached to the suit at the crotch and at the waist of the suit. The rigid structure contacts the bicycle seat when the rider is seated. The rigid structure is shaped to conform to the bicycle seat, and is also shaped to conform to the rider's body.

When the suit is pressurized to a pressure P, the positive pressure differential ΔP also results in a downwards directed resultant force $F_s$ on the suit 210. This downward force is transferred to the rigid structure of the suit at the attachment points between the rigid structure and the suit. The rigid structure supports this downward tensile load on the suit and transfers the load to the seat. The rigid structure effectively holds the suit up against the downward force $F_s$ created by the air pressure. It provides the counter force that prevents the suit from moving down the lower body when pressurized. When the suit is adequately pressurized, the body is effectively lifted off the seat. The lifting of the body reduces or eliminates the local pressure points between the rider and the bicycle seat. The rider literally floats above the seat supported by air pressure. There are no, or reduced, "pressure point" forces of the bicycle seat on the groin area of the rider. This provides for increased riding comfort and reduces or eliminates the risk of injury to the rider, Similar supporting structures and pressure suits to the ones shown in FIGS. 24-27 can be adapted for other exercising devices such as stair-masters, orbital trainers, and cross-country ski trainers.

In lieu of the wheeled or static support structure discussed above for this invention that is separate from the pressurized suit, the supporting structure component may be directly incorporated into the pressure suit so that both the supporting frame and the pressure suit and body have the same movements. In this manner the invention provides for a wide range of movements and exercises over a variety of terrains.

Figure 28:
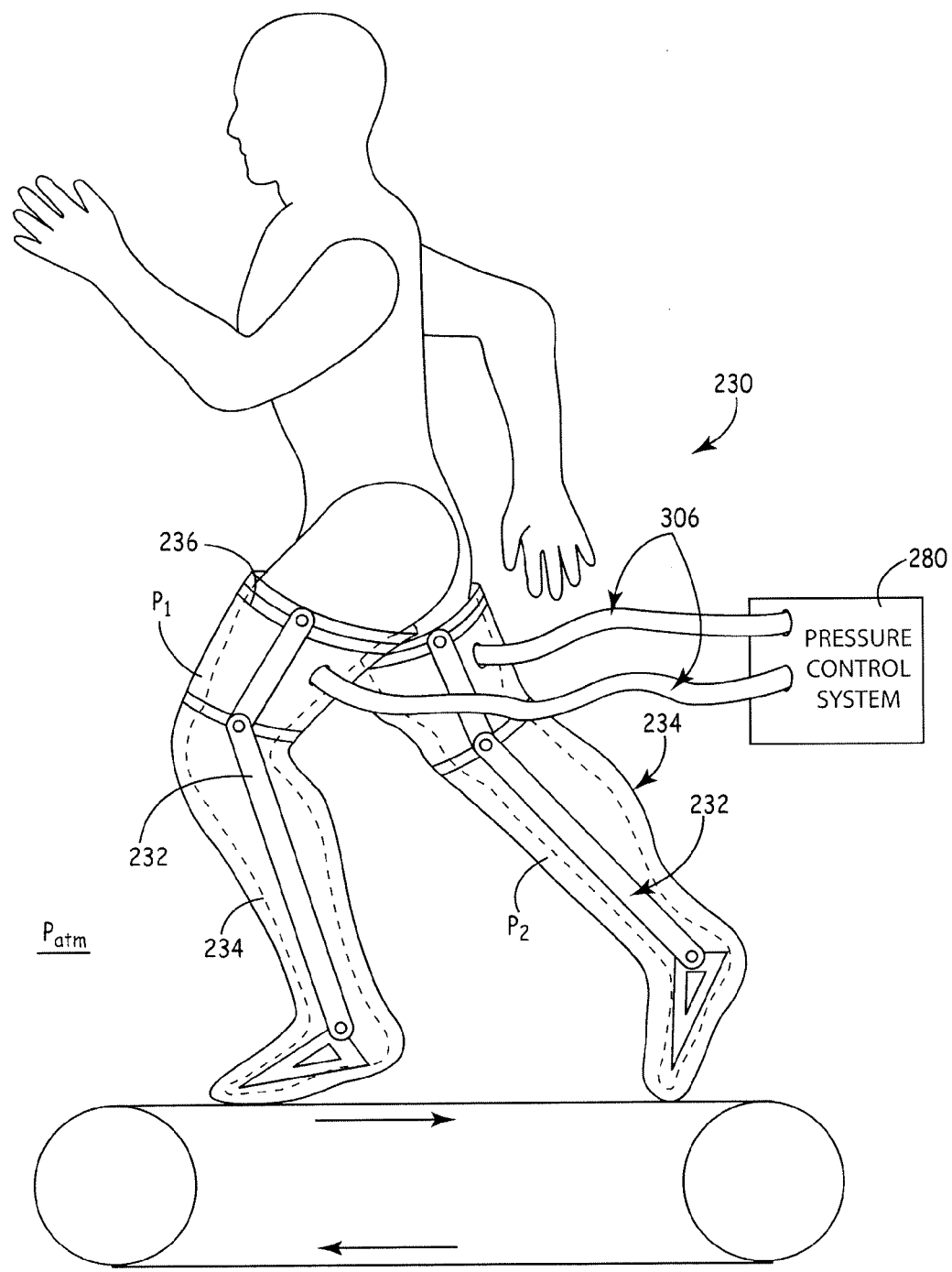
FIG. 28 is a perspective view of an external exoskeleton support structure for the body suit of the present invention.

As shown in the embodiment 230 of FIG. 28, the supporting frame is a rigid exoskeleton structure 232 made of lightweight rods and joints that is attached to the outside of the pressurized suit 234. The rigid frame and joints of the exoskeleton 232 provide the necessary support for the downward force of the pressurized suit 234. The downward force of the suit $F_d$ is equal to the upward force $F_u$ at the attachment point to the top of the exoskeleton. The exoskeleton has matching supports on the inside and the outside of the legs.

Figure 29:
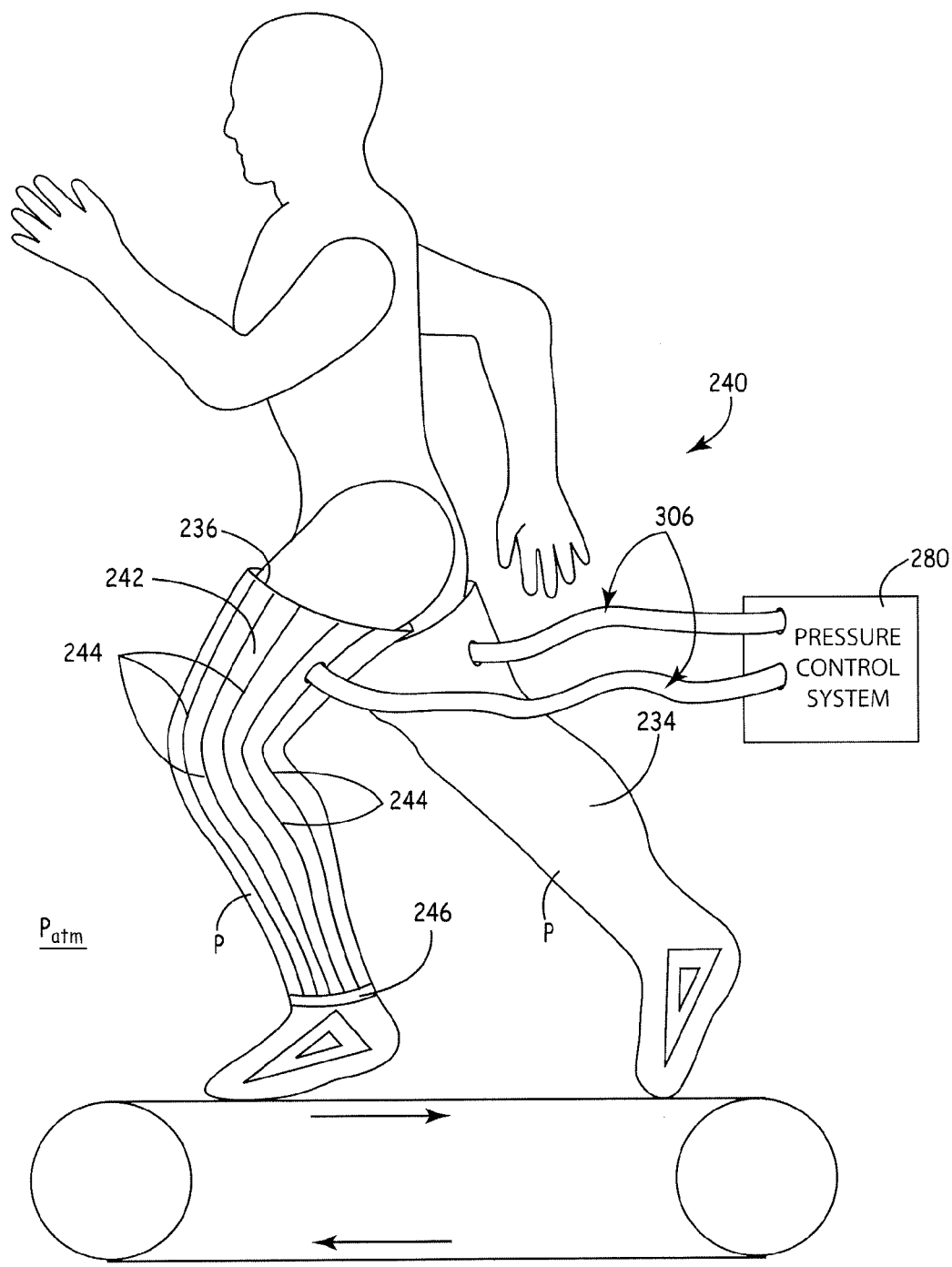
FIG. 29 is a perspective view of an internal exoskeleton support structure for the body suit of the present invention.

The embodiment 240 shown in FIG. 29 is the same as that shown in FIG. 28, with the exception that the rigid exoskeleton 242 is built into the fabric of the suit. The exoskeleton 242 comprises a number of relatively strong thin vertical rods 244 that have a flexible joint at the knee. The rods are integrated into the air-tight fabric that comprises the suit 234 as described earlier, and terminate uniformly at an ankle ring 246 that in turn conducts the force to the exterior of the boot structure and thus to the ground. Alternatively the rods 244 may be layered over the suit and suitably attached at a multitude of points. The rods generally follow the longitudinal lines of non-extension of the lower body and legs. The rods 244 are comprised of a suitable lightweight, but strong material such as aluminum or a composite material. The internal exoskeleton 242 supports the legs of the pressurized suit 234. It is depicted inside only one leg in FIG. 18 for ease of understanding.

Another type of supporting device for the assisted motion system 10 of the present invention utilizes the air pressure of the pressurized suit to support the runner. In this case, no supporting frame is required. The column of pressurized air contained in the leg units is capable of supporting a load equal to the differential pressure ΔP times the cross-sectional area of the leg unit $A_u$.

Figure 30:
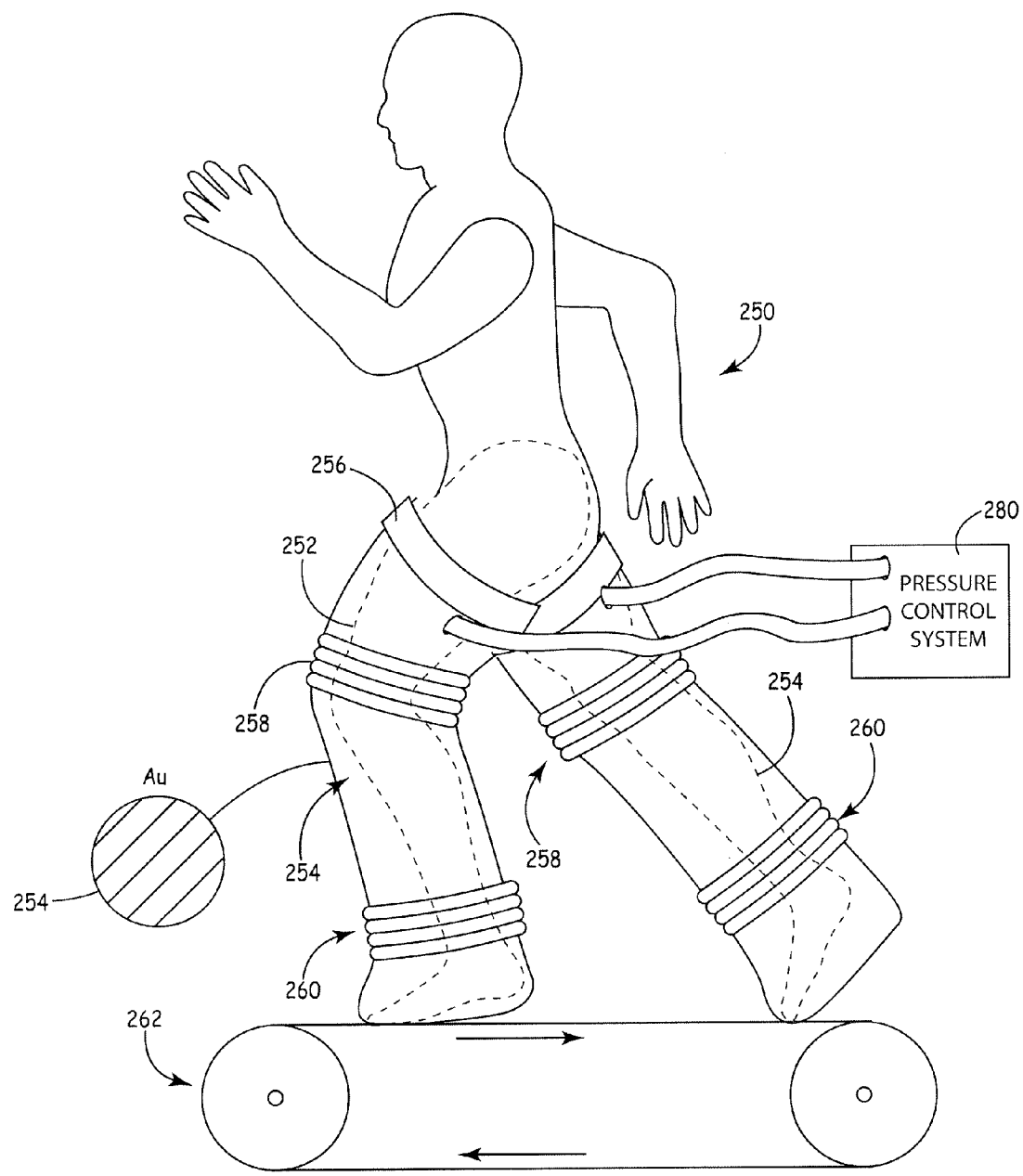
FIG. 30 is a perspective view of pressurized body suit units which provide the support structure for the body suit.

As shown in FIG. 30, in this embodiment 250 the body suit 252 consists of tubular units 254 around each leg. The leg units have an equivalent or slightly increasing cross-sectional area from the top to the bottom. This shape of the tubular units 254 results in no vertical downwards force being imparted on the exterior of the tube by the internal pressure of the unit. The units are sealed at the bottom around the foot. The units are sealed at the top against the thigh by seals 256, as described previously. The units are sized, so that the column of pressurized air can support the weight of the body that is supported by the internal differential pressure ΔP. The load supported by each unit is equal to the cross-sectional area of the unit $A_u$ times the differential pressure ΔP.

The positive pressure differential ΔP in the leg unit results in an upwards-directed resultant force $F_b$ on the body located at the centroid of the cross-sectional area $A_u$ of each leg unit. The total amount of this upwards force $F_b$ on the body from a leg unit is:

$$F_b = \Delta P \times A_u.$$

As discussed with respect to FIG. 30 for the loose-fitting suit embodiment of the pressurized suit, constant volume joints 258 at the knees and 260 at the ankles allow the pressurized leg units 254 to bend and move with the walking and running motion without the need for undue force. Loose fabric in these joints permit the volume to remain relatively constant during bending. A retaining means between the loops of fabric prevent the joint from expanding longitudinally when the tubular units 254 are pressurized. The person can conveniently exercise on a treadmill 262.

In another embodiment, the tubular units may be shaped into forms that enable the motion of the person wearing the suit 252, and provide for a more compact design. For example the tubular units may be elliptical with the longer axis aligned with the forwards-backwards axis of motion. The shape of the cross-sectional area can vary moving up and down the leg. The lower cross-sectional area can be shaped more like the lower leg and foot. The upper cross-sectional area can be shaped like the thigh. This provides for a streamlined form, which does not interfere with the running motion.

Alternatively, the tubular unit may have a separate outer pressurized chamber that provides the support. This chamber can have a higher pressure than required for providing support to the body to enable supporting a higher load with less of a cross-sectional area for the tubular unit.

The unit may also have separate smaller pressurized tubular units which support the load. Such an embodiment provides a more compact form closer fitting to the body.

The above described embodiments utilize an external mechanical support, exoskeleton, or the column of pressurized air to support the downwards force $F_s$ on the suit. The ground directly supports each foot of the exoskeleton or air pressure support. For various exercises and movements where the feet do not to leave the ground, the suit can be statically pressurized as has been previously described. However, for exercises and movements where one or both feet leave the ground, once a foot leaves the ground the downwards force of the pressure suit will tend to drive the suit leg down off the leg. Therefore, these types of movements require a cyclical pressurization and depressurization of the suit when the leg contacts and leaves the ground respectively may be done. This will provide effective off-loading of body weight when the leg is in ground contact, and prevent the suit from moving down the leg when it is not in contact with the ground.

Figure 31:
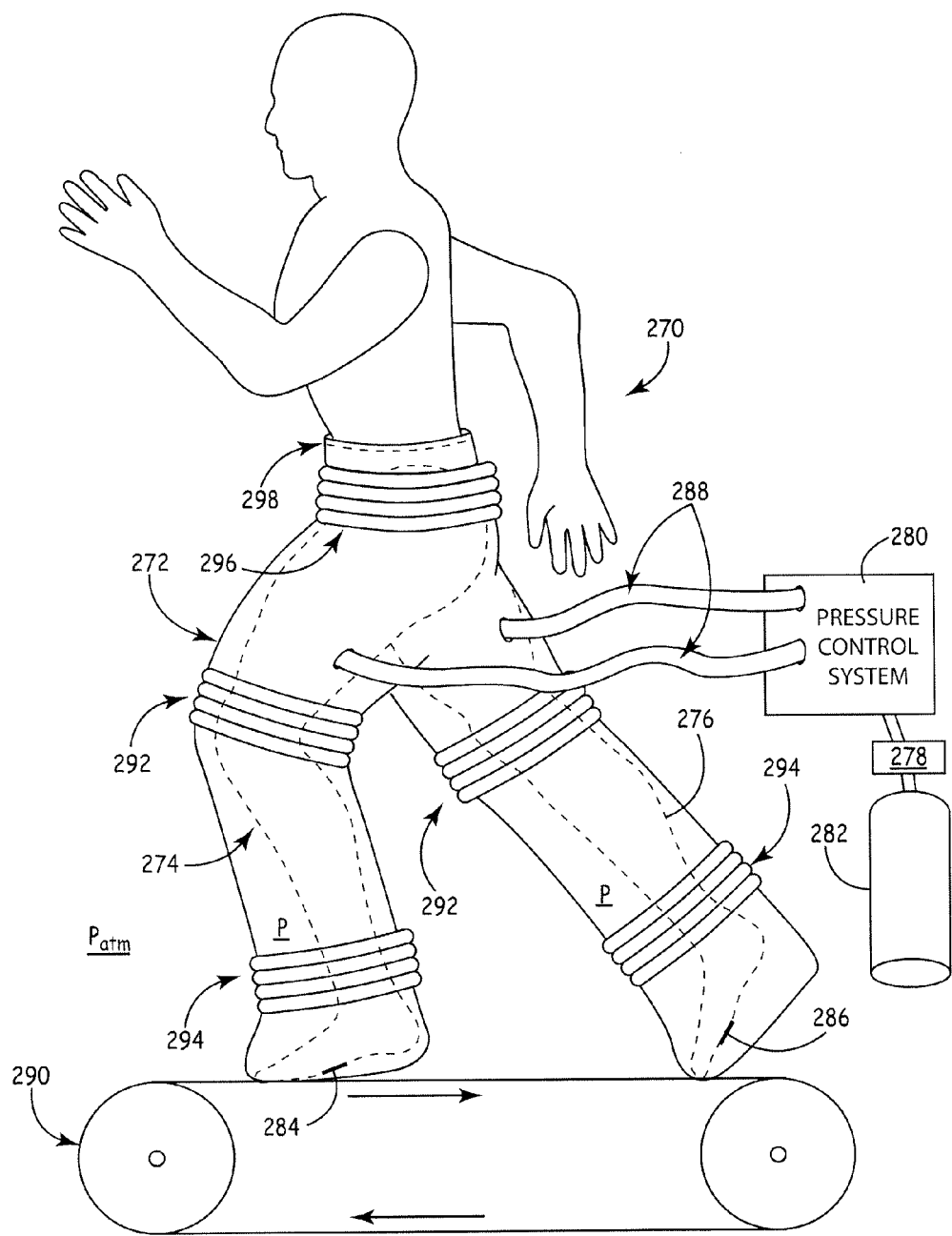
FIG. 31 is a perspective view of a loose-fitting body suit of the present invention featuring a cyclic gas pressurization/depressurization system for supporting the body suit.

FIG. 31 shows an embodiment of the invention in which the suit extends to the waist. The seal 298 positioned between the body and the outside air pressure is at the waist. This seal has an opening that is smaller than the waist, and fits tightly to provide an airtight seal under pressure. Alternatively, the seal can consist of tight-fitting, airproof compression shorts. A constant volume joint at the waist 296 allows the body to bend and move at the waist and hips with the motion of walking and running without undue force. The leg pressurization compartments extend to the waist unit, so that the waist is divided into two pressurization compartments, one corresponding to each leg. The advantage of this design is that by extending the compartment to the waist, a larger cross-sectional area is available to have a pressure differential across. This approach also has the advantage of reducing stress on the hip joint, pelvic area, and lower back.

As shown in FIG. 31, the pressure in each leg of the pressurized suit 272 is independently controlled such that the suit or a portion of the suit may be depressurized. In the phase of running depicted in FIG. 31, with the supporting leg 274 on the ground and the non-supporting leg 276 leaving the ground, positive pressure is applied to the supporting leg 274 while the non-supporting leg 276 is depressurized. Cyclic pressurization is accomplished with a control system 278 and pressurizing unit 280 to which is operatively connected a source of pressurizing gas 282. Sensors 284 and 286 under each foot sense either approaching foot strikes or incipient foot contact, and they signal the pressure unit 280 when to pressurize the appropriate leg member 274 or 276. Just prior to or upon lifting of the foot the leg member is depressurized, thereby allowing the leg to freely release from the ground for the return or "float" phase of the running cycle.

The pressurizing system 280 consists of an air pressurizing unit and pressure hoses 288 connected separately to each leg. The leg units can be pressurized to pressures $P_1$ and $P_2$ which is greater than atmospheric pressure $P_{atm}$. When depressurized the pressures $P_1$ and $P_2$ may be equal to or even less than $P_{atm}$ air. Each leg unit 274 and 276 is pressurized and depressurized separately. The cross-sectional area of the leg unit over its length is sufficient to support the weight that is supported by the air pressure. The cross-sectional area may be essentially constant, or may be increasing towards the floor.

A treadmill 290 provides for a moving surface to enable walking and running. The units may also be used with other exercising devices such as a stair-master, an orbital trainer or a stationary bicycle. Constant volume joints are provided at the knees 292, ankles 294, and waist 296 to facilitate bending of the suit 272 when it is pressurized as discussed above.

In operation during a walking/running motion, each leg unit is pressurized as the foot is placed on the ground, and depressurized when the foot is removed from the ground. A control system monitors the motion of the body and controls the pressurization and depressurization of the leg units. The control system consists of sensors 284 which detect when the leg-unit is about to contact the surface, and other sensors 286 which detect when the foot is leaving the ground on the return phase of the running cycle. The sensors may sense either pressure or the distance from the foot to the ground. The control system 278 pressurizes the leg unit which is on the ground (or just about to contact the ground) using a pressurizing unit 280 connected with sufficiently large pressure capable hoses 288. The pressurizing unit uses an electro-pneumatic regulator to change the pressure upon a signal from the control system. The pressurizing unit 280 and hoses 288 are sufficiently sized to pressurize and depressurize the units very quickly so that force on the leg is reduced immediately upon placement on the ground.

The operation of the invention is as follows: at the beginning of a walking or running step the foot being returned makes contact with the ground. Sensors on the foot determine when the foot is making or about to make contact with the ground. When the foot contacts the ground, a pressure sensor 284 detects an increased force on the outer foot of the leg unit. The sensor might also be a distance sensor such as an infrared sensor which detects the distance between the outside foot of the unit and the ground. Air pressure is applied through the control device such that when the foot makes contact with the ground (or is about to make contact with the ground) the unit is pressurized. The pressurization reduces the muscle-skeletal stresses from contact on the leg and lower body. The pressure is maintained throughout the step. Further enhancements to the control system can be made so that pressure is increased or reduced to enhance movement.

At the end of a walking or running motion, the foot is lifted off of the ground for the return. When the foot is lifted off of the ground, a pressure sensor 286 detects a reduced force on the inner foot of the user. The sensor might also be a distance sensor which detects increased space between the foot and the bottom of the leg unit. The control system depressurizes the leg unit as the leg is lifted off of the ground. Instantly depressurizing the unit removes the force of the pressurized leg unit on the ground. This allows the unit to be raised off of the ground during the return without a force either ejecting the unit from the leg or interfering with the return or float phase of the running cycle. Depressurizing the unit for the return also reduces the bending force required on the constant volume joints during the leg return.

Figure 32:
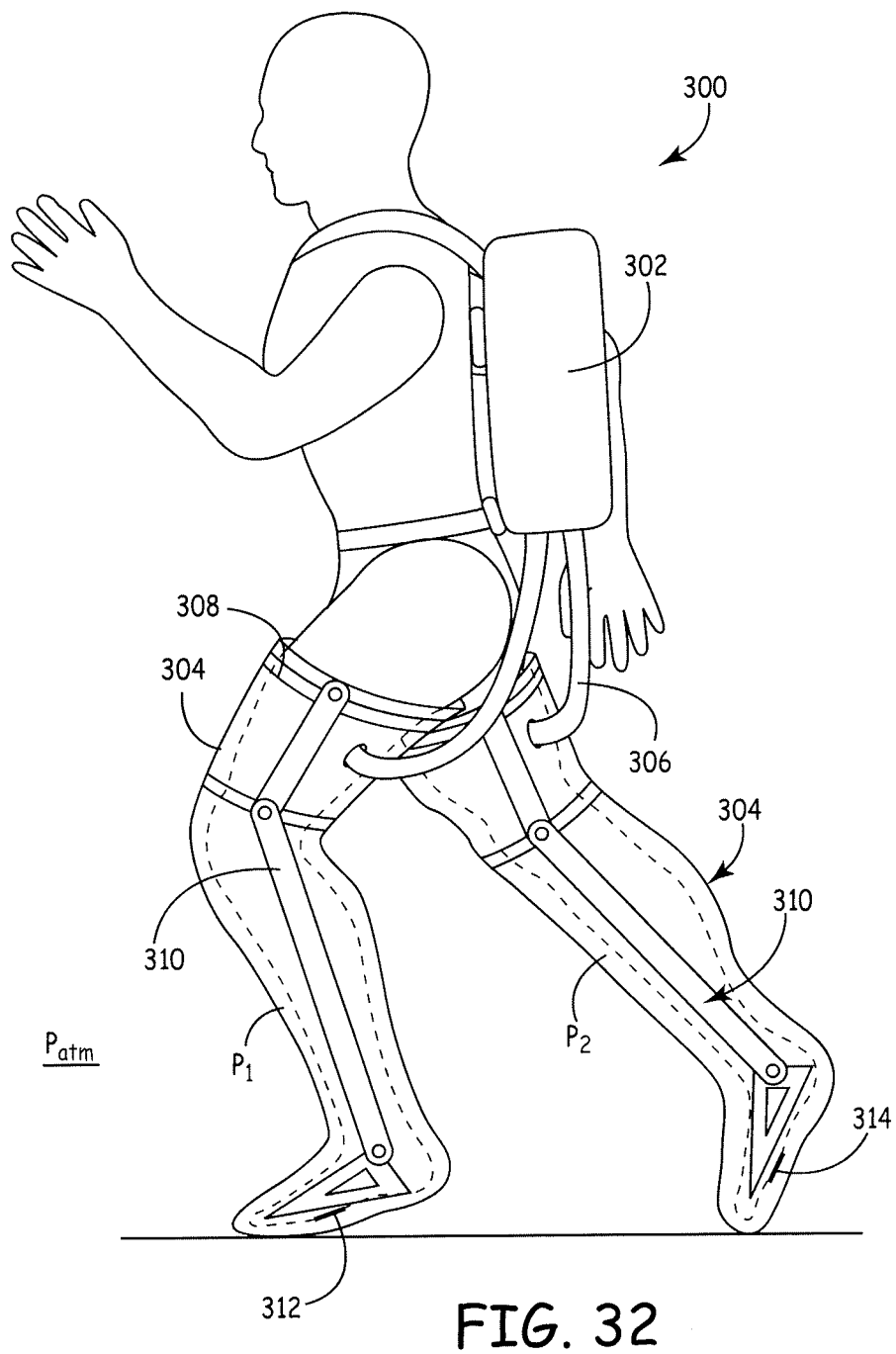
FIG. 32 is a perspective view of a portable cyclic gas pressurization/depressurization system for supporting the body suit also supported by an external exoskeleton system.

In another embodiment 300 of the invention shown in FIG. 32, the pressurizing unit and control system are portable. The pressuring unit 302 is attached to the back of the user and delivers air pressure to pressure suit 304 via hoses 306. The unit is powered to generate air pressure. Power to the unit is supplied through a battery-driven motor or gas-driven engine. Similar power units have been developed for mechanically operating pressure systems.

In this case, the pressure suit 304 covers the feet and reaches the upper thighs. A seal 308 around the top of the suit contains the positive air pressure contained inside the suit. Exoskeleton 310 attached to the exterior of the suit provides the necessary support to the pressurized suit. Sensors 312 and 314 positioned on the bottom of the feet of the suit allow the control system to cyclically pressurize and depressurize the legs of pressure suit 304 to facilitate the walking or running motion as described above.

Portability allows for walking, running, or exercising anywhere. Runners and walkers for example can exercise outside. The system 300 may be designed to enable backpackers and soldiers for example to move faster or carry heavier loads.

Portable pressurizing systems can also apply to other types of pressure suits that utilize a pressurizing mean other than pressurized air. For example, pressure suits that use such as shape-memory materials as the pressurizing device could utilize an electric current applied to the material which would create the pressure.

Figure 33:
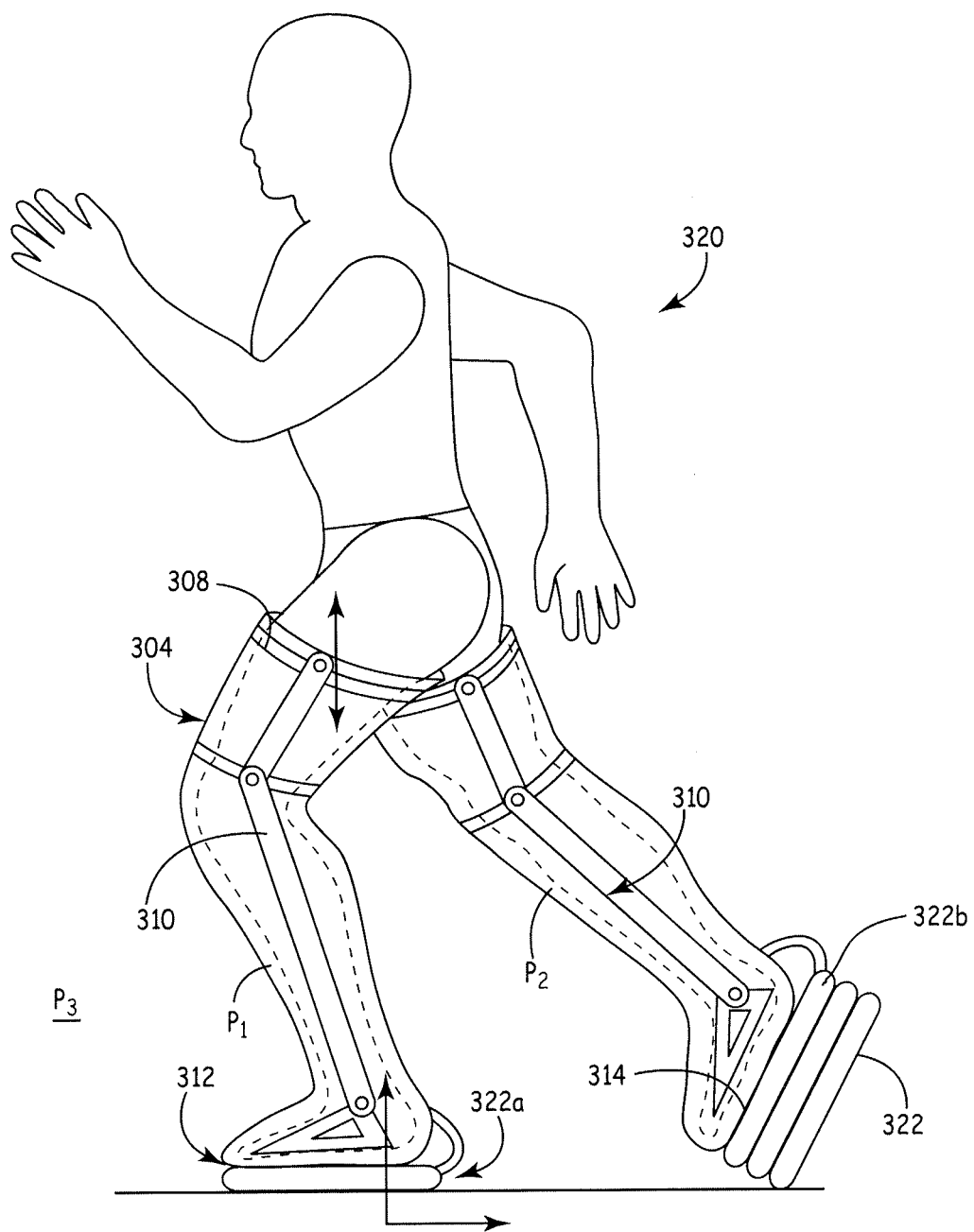
FIG. 33 is a perspective view of the portable cyclic gas pressurization/depressurization system for supporting separate pressurized body units also supported by an external exoskeleton system.

In another embodiment 320, the cycle pressurization mechanism is incorporated directly into the foot section of the suit, as shown in FIG. 33. The suit is composed of a close-fitting suit attached to an exoskeleton as described above. A foot driven air pump 322 is provided on the bottom of the foot. Pump 322a is shown on the left foot contacting the ground, while pump 322b is shown on the right foot leaving the ground. The pump is compressible with baffles and a spring return. The bottom end of the exoskeleton 310 is connected to the bottom of the air pump. When the foot is placed on the ground during a walking or running, the pump 322a is compressed, thereby delivering pressure to the suit. When the foot leaves the ground during the end of the stride, the pump 322b expands, and air flows back from the suit into the pump automatically depressurizing that leg of the suit. The foot pump is sized to provide the correct amount of pressurization. This system is automatic and does not require any outside pump or control devices.

For the suits described which provide exoskeletons as the supporting structure, the movement of various body movements can be further enhanced by using a powered exoskeleton, as is known in the art. A powered exoskeleton consists primarily of a skeleton-like framework worn by a person and a power supply that supplies at least part of the activation-energy for limb movement. Typically, a powered exoskeleton is attached at specific localized points of the body through mechanical means. These local mechanical pressure contact points on the body are deleterious. The use of differential pressure to support the body allows for the coupling of the exoskeleton to the body to be distributed over a large body surface.

The concept of supported differential pressure can be utilized to un-weight other areas of the body. For example, by creating a pressure differential between the narrower waist or lower pelvis of a seated person using a supported differential upper body pressure suit, the person's upper body weight can be unweighted. This could be used to reduce pressure on the lower back and spine for people with lower back pain, degenerative or ruptured disks, etc.

Figure 34:
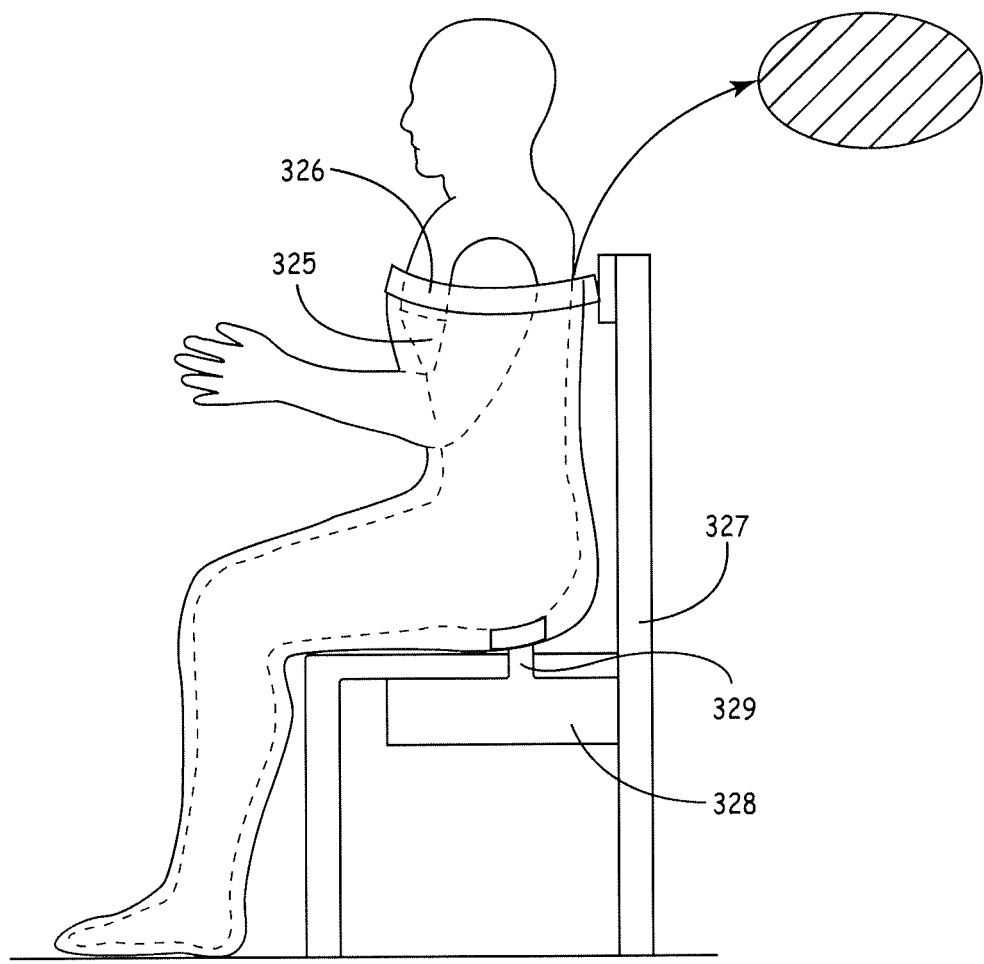
FIG. 34 is a perspective view of a body suit for the upper body to maintain its vertical posture.

An example of this suit is shown in FIG. 34. The differential pressurized suit 325 shown in FIG. 34 comprises a full-length suit which extend to the chest area just below the arms. This embodiment of the suit completely covers the feet, legs, and lower body. Alternatively, the suit may extend to the ankles, knees, or upper thigh. The suit is sealed at the chest. The seal may constitute any of the sealing methods previously discussed, including a neoprene band, an inflatable tube, or an inflatable bladder. The suit is connected to a rigid band 326. The band serves to attach the suit 14 to the supporting structure 327 which in this embodiment is a chair. The connection is such that the person may easily engage or disengage from the chair. The band 326 conforms to the generally elliptical shape of the chest cross-section. The band and connection to the supporting structure are sufficient to support the downward force of the pressurized suit. Air-tight zippers (not shown) assist entry into the full length pressure suit. The suit can connect and disconnect to connection valve 329 on the chair when the person sits down or gets up from the chair. The connection valve 329 is connected to a pressure control system 328 that can pressurize and depressurize the suit, as needed.

Figure 35:
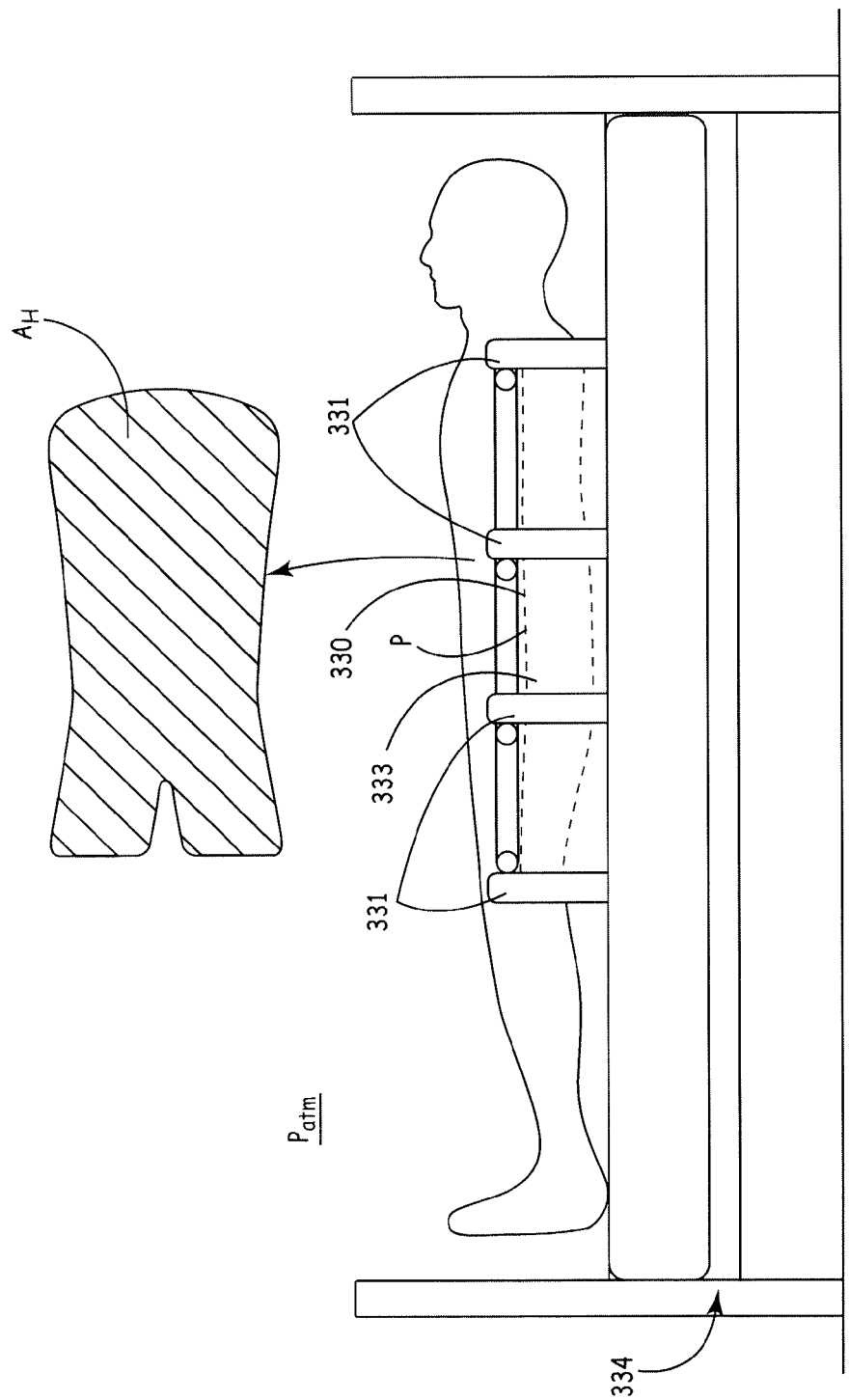
FIG. 35 is a perspective view of a body suit for the upper body to maintain its horizontal posture.

Supported differential pressure suits can also be utilized to support the body when it is in a horizontal position. The utility of this application is that patients in bed can be supported solely by differential pressure. This allows air circulation for the purpose of healing and the prevention of bedsores, for example. It removes pressure points caused by the body being supported by a mattress or other solid surface. For a person in a horizontal position, the pressure differential is created across a plane which splits the upper and lower halves of a horizontal body. This creates a large cross-sectional area $A_h$. An example of this embodiment is as shown in FIG. 35. The suit 333 extends from the shoulder area to the upper thigh, and extends vertically half way or more above the back of the person. In this case, the seal 330 separates the horizontal body between the upper and lower body halves. An air bladder, as previously utilized, is employed to contain the pressurized air between the upper and lower halves. Alternatively, in another embodiment, air-tight seals are constructed to separate the upper and lower body halves.

Rigid support structures 331 attached to or positioned on a bed 334 support the suit against the downwards force on the suit created by the differential pressure. The utility of this application is that patients in bed can be supported solely by differential pressure. This allows air circulation for the purpose of healing and the prevention of bedsores for example. It removes pressure points caused by the body being supported by a mattress or other solid surface.

The pressure suit may be connected to the supporting frame in a number of different ways: Straps on the pressure suit may be attached directly to the frame. For instance, waist straps on a waist-high pressure suit may wrap around the waist ring of a supporting frame. Another method is to have a fastener such as Velcro on the pressure suit which attaches to a mating fastener on the supporting frame. Mechanical snaps or similar fasteners may also be utilized as the attaching device. A lacing system may also be utilized where the suit is laced to the supporting frame. Elastic systems may be utilized in the connection between the supporting frame and the suit. For example, elastic straps may be used. This provides flexibility between the suit and the supporting frame to enhance body movement.

Where the supporting frame is positioned significantly above the suit, for example for a pressure suit on a large mammal, the suit can be attached to an overhead supporting frame with a system of ropes.

The supporting suit can also be attached to the frame using a zipper system. One side of the zipper is on the suit. The other side is on fabric attached to the supporting frame. The person then wears the suit attached to the supporting frame by zippering in.

Another method is to permanently fix the pressure suit to the frame. The person then simply enters the suit at the opening. For instance, a supporting suit with an opening at the waist can be fixed permanently to a ring of the supporting frame. The person simply enters the suit through this opening.

Another method is to incorporate a rigid band or other rigid structure into the supporting suit. This rigid band is then attached to the supporting suit by various mechanical fasteners. For example the rigid band can have snaps, which then snap onto the supporting frame. The supporting band can have custom fittings which nest into mating fittings on the supporting frame. A rigid structure can also simply rest on a part of the supporting frame. For example, the rigid structure in a bicycle pressure suit can simply sit on the seat of the bicycle.

The suit may also be attached to the supporting frame with air pressure. An air pressure tube can be utilized which, when inflated, presses against the supporting frame sufficient to support the suit.

Exoskeletons may be mechanically attached along the length of the suit using mechanical fasteners such as snaps or Velcro. The suit can also be permanently fixed to the exoskeleton. The exoskeleton can also be fit into sleeves in the fabric of the supporting suit. The exoskeleton can also be incorporated into the fabric of suit.

Various positive differential pressure embodiments have heretofore been described in this application for the motion assistance system 10. Negative differential pressure utilizes the same essential principle as has been described for the positive differential embodiments. However the use of negative differential pressure presents some unique opportunities for various anatomic positions of partial body suits.

Figure 36:
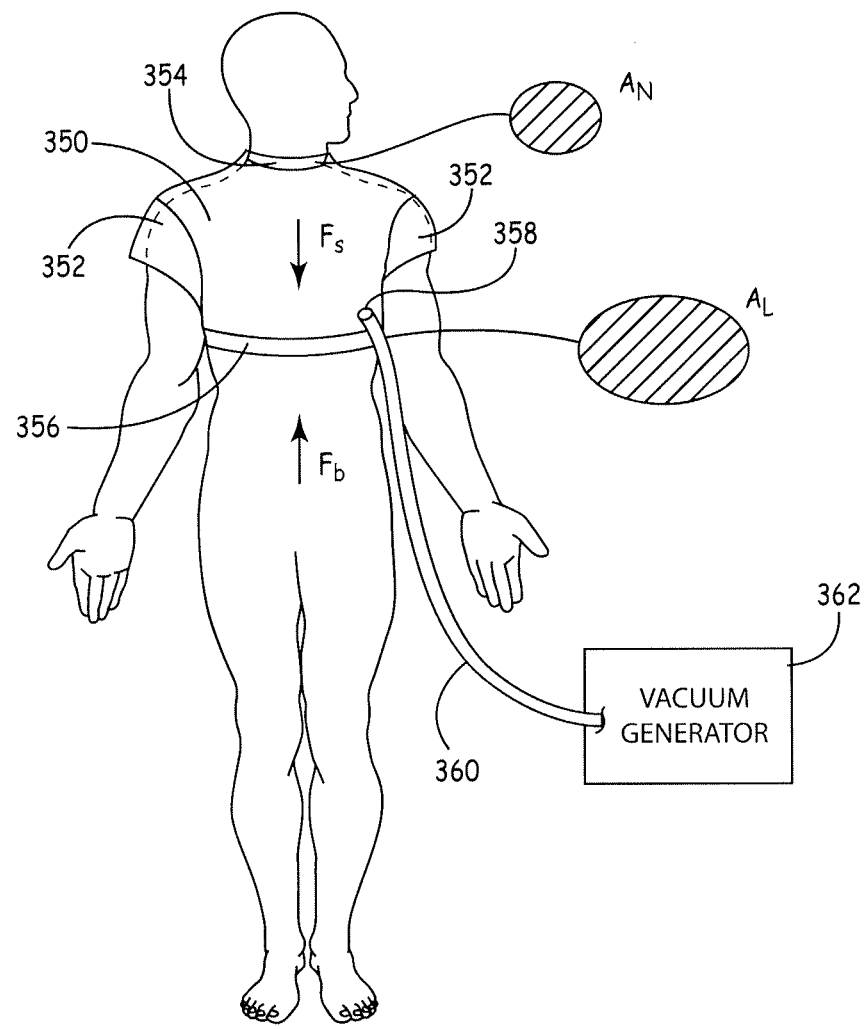
FIG. 36 is a perspective view of body suit vest for applying a negative (vacuum) pressure to the upper body.

A useful embodiment using negative differential pressure is described as follows. In FIG. 36, a person is shown wearing a vest apparatus 350, wherein the vest is a hard shell material, with the strength to support an interior partial vacuum relative to atmosphere of up to −2.0 psi. To achieve air tightness, four seals are required: two arm seals 352, a neck seal 354, and a chest seal 356. The cross-sectional area of the neck seal is denoted $A_n$, and for the chest seal $A_c$. The seals are comprised of airtight stretchable neoprene or latex sleeves connected to the interior of the hard shell vest 350. The sleeves extend far enough away from the hard shell (along the neck, arms, or chest, respectively) to ensure a reliable seal. The entire vest apparatus 350 is thus topologically like a T-shirt; the primary differences are that the neck and sleeves are tight fitting to form seals, the main body is rigid, and the bottom also forms a seal around the chest.

The hard shell vest 350 has a port 358 that connects to a vacuum hose 360 which connects ultimately to a vacuum generator 362. In use, the interior of the vest is depressurized to a partial vacuum pressure P relative to atmospheric pressure $P_{atm}$. This produces no net forces on the body in the front-back direction, nor in the lateral (left-right) direction, due to symmetry. Following the identical convention that has been previously described, the net upward vertical force is calculated with the following equation:

$$F_b = \Delta P \times (A_n - A_c)$$

Note that since $A_c$ is significantly larger than $A_n$, the quantity in parenthesis will be negative. However $$\Delta P = P - P_{atm}$$

This implies that $\Delta P$ will also be negative if P is less than $P_{atm}$ which is the case where P is a partial vacuum relative to $P_{atm}$. The multiplication of these two negatives yields a positive $F_b$, which in this coordinate system is an upward, vertical force on the body. As in prior examples, the reaction force on the suit $F_s$ will be equal in magnitude and opposite in direction to $F_b$, or downward. Counteracting or offloading $F_s$ to suitable support mechanisms such as a treadmill frame or wheeled devices are identical in principle and very similar in practice to the previously described positive pressure embodiments. The use of the two wheeled running device in conjunction with the vacuum vest 350 will be described as an exemplary, but not limiting embodiment.

The reason the vest in this embodiment only extends down to the chest (no lower than the sternum), and not to the waist, is so as not to disrupt the normal diaphragmatic distention in the abdomen, which is necessary for unencumbered ventilation. Placing the abdomen in a static vacuum would otherwise dispose the lungs toward inspiration, and would make expiration more difficult, so it is avoided in this invention.

Figure 37:
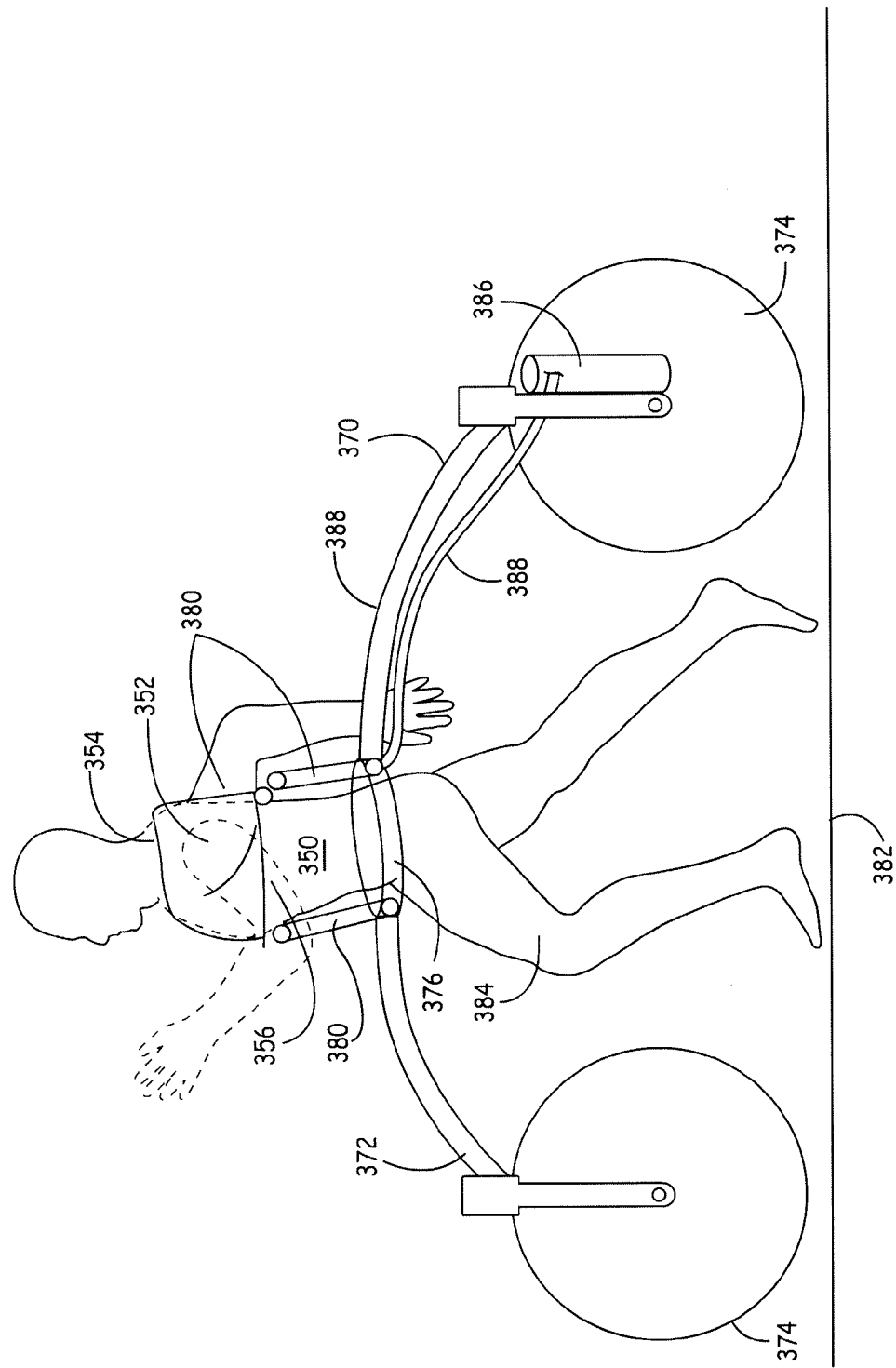
FIG. 37 is perspective view of the body suit vest of FIG. 36 with an external wheeled support frame.

FIG. 37 shows the vacuum vest 350 in conjunction with the exemplary two-wheeled offloading apparatus 370. The wheeled apparatus is shown in simplified form with frame 372 and wheels 374. Brake and steering mechanisms are omitted for the sake of clarity. The vacuum vest 350 is shown positioned on the upper torso. Note that no lower body apparatus is used in this embodiment. The runner's waist is loosely confined to a loop 376 in the frame 370.

As previously described, a neck seal 354, arm seals 352 (only one of which is visible) and chest seal 356 are shown. Rigid members 380 connect to snap fittings in the front and back of the hard shell vest 350 down to the frame 370. This carries the downward reaction force of the vest $F_s$ when under vacuum to the frame and ultimately to the ground 382 through the wheels 374. Concomitantly, the runner 384 will experience reduced weight due to upward force $F_b$. As previously described, partial vacuum P is maintained in the suit by a small mobile vacuum generator 386 attached to the rear wheel. A vacuum hose 388 run internal to the frame connects the vest 350 to the vacuum generator 386. The vacuum generator 386 is powered by a sprocket drive in tandem with the rear wheel axle, using well-known gearing means. The vacuum generator may be preset to maintain a pre-determined pressure level in the vest 350 so as to provide the desired amount of weight reduction for the runner.

The motion-assistance system 10 of the present invention can also be used for non-human mammals. This has application in veterinary medicine, for example, for supporting injured horses or dogs that need weight taken off of their lower legs. An embodiment with a moveable frame will allow the animal to exercise with a reduced load on its muscle skeletal structure.

An embodiment of a differential pressurize suit 400 for a horse 405 is depicted in FIG. 38. In this particular embodiment, the suit extends from the midsection 420 of the horse to the ankles 422 without covering the hooves, and is sealed at the cannon (metacarpas) of each of the four legs. The suit 400 is a close-fitting multi-layer suit, as described earlier. In this embodiment, the pressurized air is contained by means of an airtight bladder 402, as previously described. The bladder consists of an airproof inner layer 403 and outer layer 404. The two layers are joined at the top and bottom of the suit to form an airtight bladder. When pressurized, the inner layer presses against the hide of the horse, and the outer layer presses against the outer constraining layer of the suit. A frontal view of the bladder 402 is shown in FIG. 39. The bladder 402 contains air at pressure P. The bladder may be used for the various embodiments of the pressure suits described herein, including a bladder that extends from the waist to around the foot, a bladder that extends from the waist to the ankle, and a bladder that extends from the waist to above the knee.

The midsection seal portion of the suit may include a rigid band 406. Zippers on the suit allow the suit to be easily put on and removed from the horse 405. In this manner, when the suit is pressurized with air to pressure condition P, the pressurized air is substantially contained within the suit 400.

The net upward force provided by pressurized air contained within suit 400 may be calculated as:

$$F_b = \Delta P (A_m - 4A_C)$$

where $\Delta P$ is the difference in pressure level P inside the suit and atmospheric pressure $P_{atm}$ outside the suit. $A_m$ is the cross-sectional area of the midsection. $A_C$ is the cross-sectional cannon area of each leg.

Four-legged animals have a cross-sectional area at the midsection of the body that is large relative to the weight of the animal. A small amount of positive pressure P can easily support the weight of a large horse as shown in the following example. Measurement and weight data is available on Fumiro KashiWamura, Avarzed Avgaanorj and Keiko Furumura, "Banei Draft Racehorses: Relationships among Body Size, Conformation, and Racing Performance in Banei Draft Racehorses," *J. Equine Sci*, vol. 12, no. 1, pp. 1-7 (2001.).

Average Measurements for two-year-old horses are: body length BL=74.2 inches; chest width WC=32.4 inches; hip width WH=26.5 inches; cannon diameter CD=3.4 inches, weight=1983.2 lbs From this the cross-sectional area of the midsection $A_m$ is calculated to be 2185.2 square inches. The cross-sectional area of the cannon of the lower leg $A_m$ is calculated to be 10.6 square inches. For a suit 400 pressurized to a modest 0.5 psi positive differential pressure, the upward force on the horses body $F_b$ is 1071.4 lbs. For a positive pressure differential of 0.5 psi, over 50% of the horse's body weight can be taken off its muscle-skeletal structure. A 1.0 psi positive pressure differential could effectively take off all of the horse's body weight.

Figure 40:
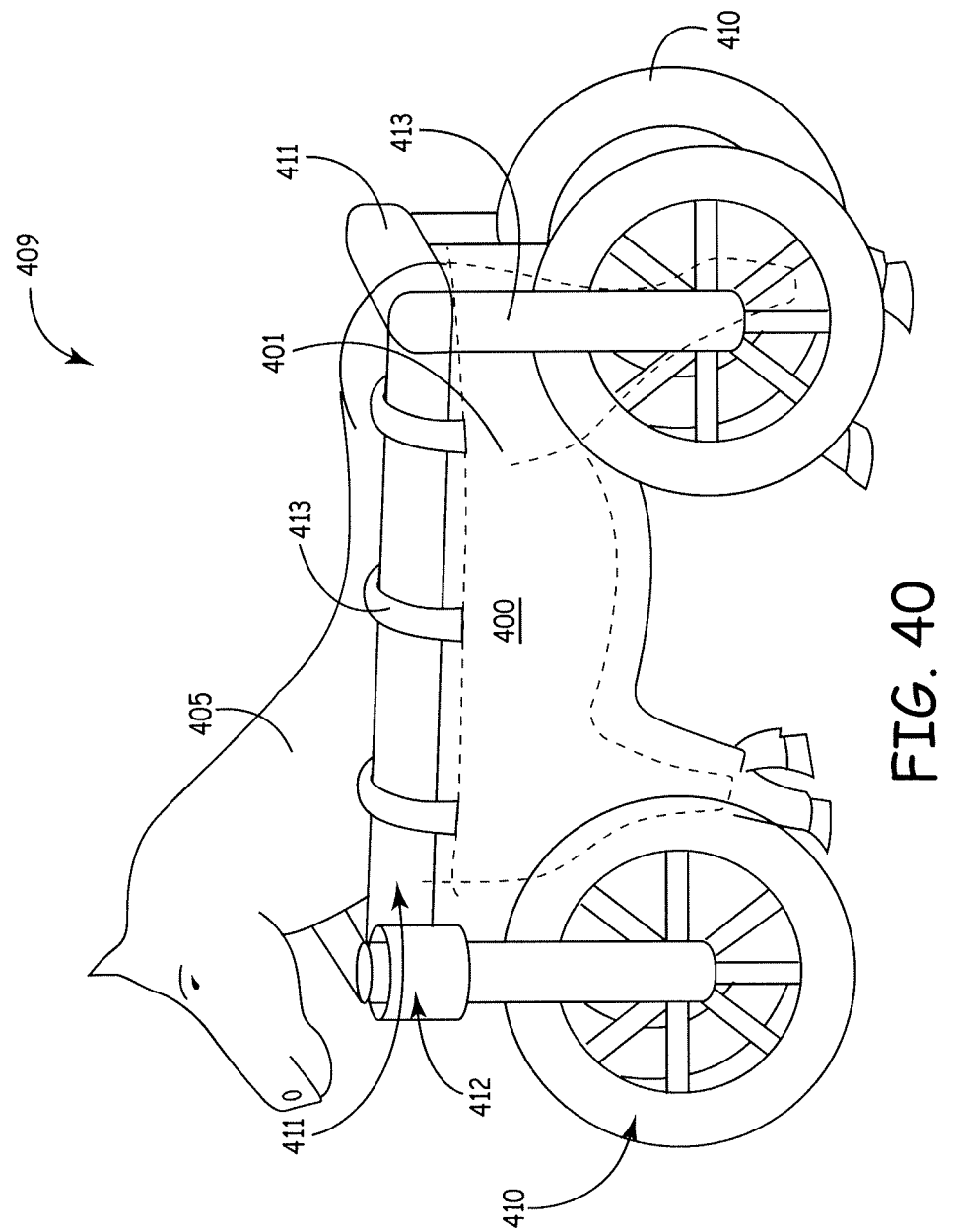
FIG. 40 is a perspective view of the horse body suit of FIGS. 38-39 with an external wheeled cart support frame.

An embodiment of a moveable structure 409 for exercising a horse 405 is shown in FIG. 40. It comprises a cart-like structure with four wheels, arranged as pairs of wheels lateral to the left and right sides of the horse. In this embodiment, the frame 411 is connected to each wheel 410 lateral to the horse 405, leaving a clear path to the front and back of the horse by the horse. The front wheels operate independently and are implemented as turnable castors 412 to accommodate steering. The rear wheels also rotate independently, but are fixed on their vertical axis. The pressure suit 400 is attached to the frame 411 by means of straps 413. When the suit is pressurized, a portion of the horse's weight is off-loaded via the pressure suit 400, and transmitted to the frame, axle shafts, and ultimately the ground. Steering is accomplished passively in that the cart simply follows direction changes engendered by the horse's change in direction, which applies twist through the frame to the front wheel castor mechanisms in a manner similar to a steering a shopping cart.

EXAMPLES

Example 1

A working model of pressure shorts (waist to above the knees) to reduce the effective body weight of an individual was constructed and tested as follows. Shorts were sewn using airproof, rubberized nylon material (Harris Canvas, Minneapolis, Minn.), following a standard shorts pattern with legs extended to reach just above the knees. Seals were created above each knee by obtaining commercially available compression leggings. The leggings were made airtight by applying a complete coat of seam sealer (Seam Lock sold by REI, Inc. of Sumner, Wash.). The leggings were worn by the test individual from mid-thigh, and they terminated just above the knee joint. Each legging was interfaced to a leg of the nylon exterior shorts by placing each over a 7" diameter steel ring, and then clamping together with a worm gear of said diameter. This was done for expediency. In a commercial application, this union would simply be sewn together, and seam sealed. The waist seal was constructed using a pair of airtight, skintight, neoprene interior shorts. The waist of these inner shorts and the waist of the outer rubberized nylon shorts were sewn together and seam sealed to form an airtight seal. This oval waist-sized seal was sandwiched between a pair of boards, each 16"×28" with a 11.5"×15" oval cut-out to allow a person to 'climb in'.

An air intake fitting was installed in one leg of the outer nylon shorts. Once an individual placed himself in the apparatus, air pressure was applied to the air fitting, and air pressure was monitored via a second pressure port in the pants, using a high fidelity electronic pressure transducer. The oval board affixed to the shorts was clamped to vertical stands that rested on the ground. Thus, consistent with earlier descriptions of this invention, air pressure, when applied, will tend to push the individual up, with the reaction force on the pressure shorts tending to push the shorts down. The reaction force was countered in this case with the vertical stands that fix to the oval board and thus to the pressure shorts. Thus, the reaction force was effectively communicated to the ground. A weighing scale was placed beneath the individual to record his weight as a function of the applied air pressure to the pressure shorts.

Figure 41:
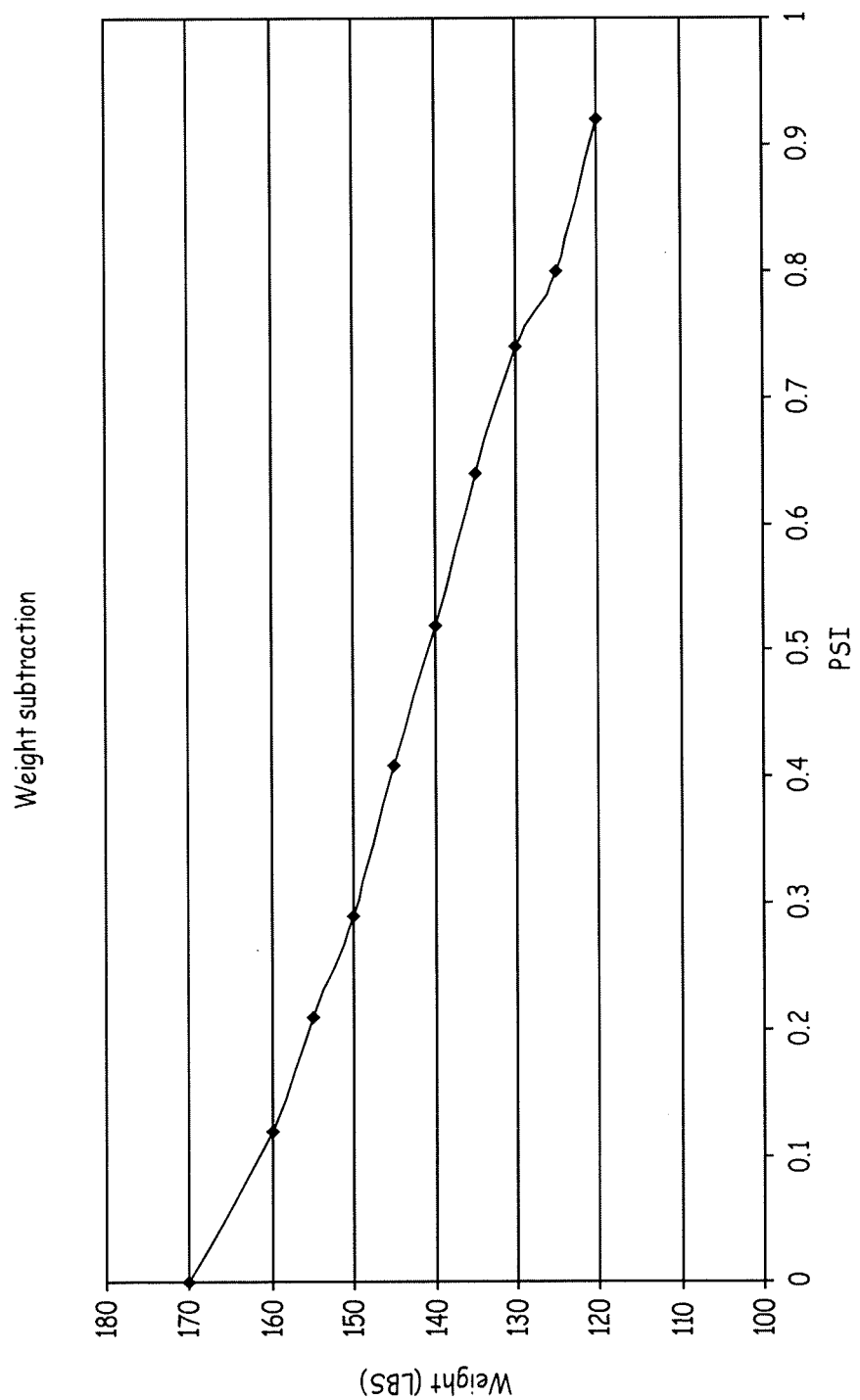
FIG. 41 is a graphical representation of the experimental weight results of an individual wearing the pressurized body suit of Example 1.

The expected weight reduction was calculated as follows: the cross section of each leg just above the subject's knee was estimated, based upon circumferential measurements, to be 15 square inches, for a total of 30 square inches. The area of the waist ellipse was measured as 78 square inches. Thus the vertical area differential was 48 (i.e., 78-30) square inches. This implies that 1 PSI would provide a lift, or weight reduction of 48 pounds. As shown in FIG. 41, the slope of the linear regression of the experimentally obtained and plotted data was 51.5 pounds/pounds-per-square-inch, or 51.5 square inches. This is excellent experimental agreement, within 10% of the expected 48 square inches obtained from the cross sectional area estimations.

Example 2

Prototype Pressurizing Suit

A prototype pressurizing suit extending from the waist to around the feet having an air bladder-type seals was constructed. The suit was constructed of two neoprene waders sized large and extra-large. The neoprene waders were both waterproof and airproof. The smaller waders were placed inside the larger-sized waders. The waders were fastened together at the waist using an epoxy adhesive to form an airtight seal. This formed an airproof compartment between the outer wader and the inner wader, which could be pressurized. When pressurized, the inner wader formed a seal against the body; the outer wader formed the pressurized body suit. An automobile air valve was attached to the outer wader to allow the unit to be pressurized.

The body suit was pressurized using a standard air compressor. A hose from the air compressor was attached to the valve in the suit. When pressurized, the user could feel pressure on his legs and reduced force on his legs. Movement was possible without lifting the legs from the floor.

The suit was fitted upon a larger user, and the pressure was increased. The pressure was increased sufficiently such that the user's weight was being totally supported by air pressure. The user's feet were off of the floor. Movement was possible without lifting the feet from the floor.

Example 3

Pressurized Leg Unit

A pressurized leg unit extending from the thigh to around the foot was constructed. The unit was constructed as follows: A waterproof hip wader was fitted tightly over a section of plastic PVC pipe. The pipe had an inner diameter slightly larger than the user's thigh. An airtight seal was formed between the leg and the neoprene. On the top of the unit, an inner seal was formed by applying neoprene to the inner diameter of the PVC tube to a sufficient thickness, so that a tight airtight seal was formed between the neoprene and the user's thigh. A pressure hose fitting was attached to the PVC pipe to allow the unit to be pressurized. The unit was pressurized to less than 3 psi. The pressure was sufficient that the user noticed a reduction in weight and pressure on his foot.

Example 4

Cyclically Pressurized Suit

A proof of concept of a hip-length, dynamically-pressurized pant was constructed.

A rubberized nylon pant was sewn, including an integrated foot section large enough to accommodate the runner's bare foot inside. To create a thigh seal, a compression pant sleeve was sewn interior to the pant around the thigh opening, and made airtight with seam sealer in the form of Seam Lock sold by REI, Inc. of Sumner, Wash. Compression sleeves were sourced from Advanced Brace of Irving, Tex. Thus an airtight compartment was made when the test subject's thigh was put into the pant. A standard air intake fitting was installed in the pants, as was a high-fidelity pressure transducer (ACSX05DN sold by Honeywell, Inc.). An air supply system with a solenoid controlled intake valve and exhaust valves (SCM Inc.) were connected to the air intake port. The solenoids were independently controlled from a computer controlled digital I/O system (Phidgets Inc.), and in addition the computer had the pressure transducer signal input into an analog-to-digital converter (Phidgets). An "electric eye" was implemented, using a photo electric driver-receiver pair (C18P-AN-1A sold by Automation Direct). The eye was aimed such that the optical beam would break and trigger a logic signal going into the digital I/O signal when the subject's foot was just above the treadmill surface. A software program in the computer was written to actuate the intake and exhaust valves and thus dynamically pressurize the pant as follows. During forward (float) motion of the leg with the pant, the exhaust valve was maintained open and the intake valve was closed. When the subject's foot was just above the treadmill surface (about 100 ms before contact), the photoelectric signal would trigger a logic one, and the computer program would actuate the states of the two valves to reverse, such that fairly high air flow (20 psi nozzle pressure) was allowed to fill the pant until the pressure transducer registered 1 psi. This created the un-weighing portion of the cycle for this leg, which was maintained until the subject had moved forward to where his leg was behind him and about to come up off the treadmill surface, when the exhaust valve was opened. During the subsequent return phase of the leg with the pant, since it was now depressurized, flexure at the knee was easy. It was verified that with 1 PSI of pressure, over 80 pounds of net upward lift was created, and with somewhat more air pressure, a 135 pound individual was completely levitated.

The above specifications and drawings provide a complete description of the structure and operation of the assisted motion system 10 under the present invention. However, the invention is capable of use in various other combinations, modifications, embodiments, and environments without departing from the spirit and scope of the invention. Therefore, the description is not intended to limit the invention to the particular form disclosed, and the invention resides in the claim and hereinafter appended.

We claim:

1. A method for assisting the motion of or supporting a body of a mammalian user having a body weight during the course of a treatment procedure, such method comprising:
   (a) providing to the user a pressure-tight suit made from flexible fabric adapted to being worn over all or a portion of one or more of the user's body parts consisting of a torso, leg, or arm, the pressure-tight suit having at least one opening around the user's torso, leg, arm or a neck for accommodation by the pressure-tight suit of the body parts;
   (b) providing a pressure-tight seal connected adjacent to each opening of the pressure-tight suit for operative engagement of a body part surface of the user;
   (c) providing inlet means in the suit for introduction of at least one source of a positive pressure to an interior of the suit between the user's body parts and the suit to create a differential pressure condition therein between the positive pressure condition inside the suit, and a pressure condition existing outside the suit;
   (d) providing mobile support means separate from the suit connected to the suit for counteracting a downwards force applied to the suit when it is placed under the differential pressure condition;
   (e) whereby the differential pressure condition contained inside the suit exerts an upwards force upon the user's body to offload a portion of the weight of the body to the support means to facilitate the treatment procedure undergone by the user.

2. The method of claim 1, wherein the treatment procedure comprises rehabilitation of a skeletal joint injury or to assist mobility.

3. The method of claim 1, wherein the treatment procedure comprises training the user to prevent injury.

4. The method of claim 1, wherein the treatment procedure comprises training the user to enhance athletic performance.

5. The method of claim 1, wherein the treatment procedure comprises assisting the mobility of an elderly or disabled user.

6. The method of claim 1, wherein the treatment procedure comprises reducing weight on a muscle skeletal structure of the user.

7. The method of claim 1, wherein the pressure-tight suit closely fits the user's body parts.

8. The method of claim 7, wherein the closely-fit pressure-tight suit comprises multiple layers of material.

9. The method of claim 8, wherein at least one layer comprises an inner vent layer, air pressure resistant layer, or a layer for restraining a force applied by the positive pressure source to the closely-fit pressure-tight suit.

10. The method of claim 9, wherein the restraining layer constrains an application of downwards force, circumferential force, or longitudinal force to the closely-fit pressure-tight suit.

11. The method of claim 1, wherein at least one layer of material within the closely-fit pressure-tight suit is extensible along a first axis, and non-extensible along a second axis perpendicular to the first axis.

12. The method of claim 1, wherein the pressure-tight suit loosely fits the user's body parts.

13. The method of claim 12, wherein the loosely-fit pressure-tight suit comprises at least one joint for encompassing a joint within a muscle skeletal structure of the user.

14. The method of claim 13, wherein the pressure-tight suit joint is a constant-volume joint.

15. The method of claim 12, wherein the pressure-tight suit comprises two tubular leg units having independent pressure conditions covering at least two legs of the user, and the source of positive pressure comprises a first positive pressure condition that is introduced to a tubular leg unit of the pressure-tight suit corresponding to a foot that is in contact with a hard surface, and a second positive pressure condition less than the first positive pressure condition that is introduced to a tubular leg unit of the pressure-tight suit corresponding to another foot that is removed from the hard surface, further comprising a controller for regulating the cycling between the first and second positive pressure conditions introduced to tubular leg units.

16. The method of claim 15, wherein the pressure-tight suit further comprises at least one sensor positioned below the foot of the user for detecting when the foot comes into contact with the hard surface, or a relative distance of the foot with respect to the hard surface, such sensor providing a signal to the controller to regulate the cycling between first and second positive pressure conditions delivered to the pressure-tight suit.

17. The method of claim 15, wherein the treatment procedure comprises providing the medical benefits of massage or enhanced venous return of blood to the heart of the user.

18. The method of claim 1, wherein the pressure-tight seal comprises an airproof elastic sleeve, airproof band, an airproof pair of shorts attached to the interior of the pressure-tight suit adjacent to a sealing location, inflatable air tube seal, or air bladder.

19. The method of claim 1, wherein the at least one source of positive pressure is provided by a mobile source of pressurized gas.

20. The method of claim 19, wherein the pressurized gas comprises air, nitrogen, carbon dioxide, or argon.

21. The method of claim 1, wherein the at least one source of positive pressure is produced by energy expended by the user.

22. The method of claim 1, wherein the at least one source of positive pressure is produced by a foot-driven air pump operatively connected to a foot of the user.

23. The method of claim 1 for the user having an upper body and lower body and feet, wherein the pressure-tight suit is sealed around a dividing circumference between the upper body and lower body of the user, and extends down the lower body to cover the feet of the user.

24. The method of claim 1 for the user having a waist and lower body and ankles, wherein the pressure-tight suit is sealed around the waist of the user, and extends down the lower body to seal around the ankles of the user.

25. The method of claim 1 for the user having a waist and lower body and knees, wherein the pressure-tight suit is sealed around the waist of the user, and extends down the lower body to seal around the knees of the user.

26. The method of claim 1, wherein the pressure-tight suit comprises separate leg units, each leg unit being sealed around a thigh of the user, and extending down a lower body to seal around an ankle or knee of the user.

27. The method of claim 1 for the user having a chest and lower body and feet, wherein the pressure-tight suit is sealed around the chest of the user, and extends down the lower body to cover the feet of the user.

28. The method of claim 1 for the user having an upper body, wherein the pressure-tight suit covers the upper body of the user.

29. The method of claim 1 for the user having an upper body and waist and neck and arms, wherein the pressure-tight suit covering the upper body of the user is sealed above the waist and adjacent to the neck and arms of the user.

30. The method of claim 1 for the user having a waist, wherein the pressure-tight suit is operatively connected to a rigid band on the support means for encircling the waist of the user wearing the suit.

31. The method of claim 1, wherein the support means separate from the suit comprises at least two wheels.

32. The method of claim 1, wherein support means separate from the suit comprises a wheel substantially ahead of the mammal, and a wheel substantially behind the mammal.

33. The method of claim 1, wherein support means separate from the suit comprises a cart or walker device.

34. The method of claim 33 further comprising means for steering or braking the support means.

35. The method of claim 1, wherein the support means separate from the suit comprises an exoskeleton attached to an exterior surface of the pressure-tight suit, or embedded within the pressure-tight suit.

36. The method of claim 1, wherein support means separate from the suit comprises a stationary frame, chair, bed, or other stationary surface for supporting a body part of the user.

37. The method of claim 36, wherein the stationary frame support means separate from the suit enables a user wearing the pressurized suit to use a treadmill, stair-master, orbital trainer, cross-country ski trainer, or other exercise apparatus.

38. The method of claim 36, wherein the stationary frame support means separate from the suit accommodates lateral, longitudinal, or vertical movement of the user wearing the pressurized suit.

39. The method of claim 38, wherein the stationary frame support means separate from the suit comprises means for providing a constant force to support the vertical downwards loads force applied by the pressurized suit connected to the support means, while accommodating the vertical movement of the user's body.

40. The method of claim 1, wherein the mammal to which the pressure-tight suit is adapted is a human or four-legged animal.

41. A method for assisting the motion of or supporting a body of a mammalian user having a body weight during the course of a treatment procedure, such method comprising:
    (a) providing to the user a pressure-tight suit made from flexible fabric adapted to being worn over all or a portion of one or more of the user's body parts consisting of a torso, leg, or arm, the pressure-tight suit having at least one opening around the user's torso, leg arm, or a neck for accommodation by the pressure-tight suit of the covered body parts;
    (b) providing a pressure-tight seal connected adjacent to each of the openings of the suit for operative engagement of a body part surface of the user;
    (c) providing inlet means in the suit for introduction of at least one source of a positive pressure to an interior of the suit between the user's body parts and the suit to create a differential pressure condition therein between the positive pressure condition inside the suit, and a pressure condition existing outside the suit;
    (d) providing a stationary support means separate from the suit connected to the suit for counteracting a downwards force applied to the suit when it is placed under the differential pressure condition;
    (e) whereby the differential pressure condition contained inside the suit exerts an upwards force upon the user's body part to offload a portion of the weight of the body to the support means to facilitate the treatment procedure undergone by the user.

42. The method of claim 41, wherein the treatment procedure comprises maintaining proper posture of a muscle skeletal structure of the user.

43. The method of claim 41, wherein the treatment procedure comprises reducing or preventing bed sores in a bed-rest patient user.

44. The method of claim 41, wherein the pressure-tight suit closely fits the user's body parts.

45. The method of claim 44, wherein the closely-fit pressure-tight suit comprises multiple layers of material.

46. The method of claim 45, wherein at least one layer comprises an inner vent layer, air pressure resistant layer, or a layer for restraining a force applied by the positive pressure to the closely-fit pressure-tight suit.

47. The method of claim 46, wherein the restraining layer constrains an application of downwards force, circumferential force, or longitudinal force to the closely-fit pressure-tight suit.

48. The method of claim 41, wherein at least one layer of material within the closely-fit pressure-tight suit is extensible along a first axis, and non-extensible along a second axis perpendicular to the first axis.

49. The method of claim 41, wherein the pressure-tight suit loosely fits the user's body parts.

50. The method of claim 49, wherein the loosely-fit pressure-tight suit comprises at least one joint for encompassing a joint within a muscle skeletal structure of the user.

51. The method of claim 50, wherein the pressure-tight suit joint is a constant-volume joint.

52. The method of claim 49, wherein the pressure-tight suit comprises two tubular leg units having independent pressure conditions covering all or a portion of two legs of the user, and the source of positive pressure comprises a first positive pressure condition that is introduced to a tubular leg unit of the pressure-tight suit corresponding to a foot that is in contact with a hard surface, and a second positive pressure condition less than the first positive pressure condition that is introduced to a tubular leg unit of the pressure-tight suit corresponding to another foot that is removed from the hard surface, further comprising a controller for regulating the cycling between the first and second positive pressure conditions introduced to the tubular leg units.

53. The method of claim 49, wherein the pressure-tight suit further comprises at least one sensor positioned below the foot of the user for detecting when the foot comes into contact with the hard surface, or a relative distance of the foot with respect to the hard surface, such sensor providing a signal to the controller to regulate the cycling between first and second positive pressure conditions delivered to the pressure-tight suit.

54. The method of claim 41, wherein the pressure-tight seal comprises an airproof elastic sleeve, airproof band, an airproof pair of shorts attached to the interior of the pressure-tight suit adjacent to a sealing location, inflatable air tube seal, or air bladder.

55. The method of claim 41 for the user having an upper body and lower body and feet, wherein the pressure-tight suit is sealed around a dividing point between the upper body and lower body of the user, and extends down the lower body to cover the feet of the user.

56. The method of claim 41 for the user having a waist and lower body and ankles, wherein the pressure-tight suit is sealed around the waist of the user, and extends down the lower body to seal around the ankles of the user.

57. The method of claim 41 for the user having a waist and lower body and knees, wherein the pressure-tight suit is sealed around the waist of the user, and extends down the lower body to seal around the knees of the user.

58. The method of claim 41, wherein the pressure-tight suit comprises separate leg units, each leg unit being sealed around a thigh of the user, and extending down a lower body to seal around an ankle or knee of the user.

59. The method of claim 41, wherein the at least one source of positive pressure is provided by a stationary source of pressurized gas.

60. The method of claim 41, wherein the mammal to which the pressure-tight suit is adapted is a human or four-legged animal.

61. A method for assisting the motion of or supporting a body of a mammalian user having a body weight during the course of a treatment procedure, such method comprising:
(a) providing to the user a pressure-tight suit made from flexible fabric adapted to being worn over all or a portion of one or more of the user's body parts consisting of a torso, leg, or arm, the pressure-tight suit having at least one opening around the user's torso, leg, arm, or a neck for accommodation by the pressure-tight suit of the body parts;
(b) providing a pressure-tight seal connected adjacent to each opening of the pressure-tight suit for operative engagement of a body part surface of the user;
(c) providing inlet means in the suit for introduction of at least one source of vacuum to an interior of the suit between the user's body parts and the suit to create a differential pressure condition therein between the vacuum condition inside the suit, and a pressure condition existing outside the suit;
(d) providing mobile or stationary support means separate from the suit connected to the suit for counteracting a downwards force applied to the suit when it is placed under the differential pressure condition;
(e) whereby the differential pressure condition contained inside the suit exerts an upwards force upon the user's body to offload a portion of the weight of the body to the support means to facilitate the treatment procedure undergone by the user.

62. The method of claim 61, wherein the at least one source of vacuum is provided by a portable vacuum pump.

63. A method for assisting the motion of or supporting a body of a mammalian user having a body weight during the course of a treatment procedure, such method comprising:
(a) providing to the user a pressure-tight suit made from flexible fabric adapted to being worn over all or a portion of one or more of the user's body parts consisting of a torso, leg, or arm, the pressure-tight suit having at least one opening around the user's torso, leg, arm, or a neck for accommodation by the pressure-tight suit of the body parts;
(b) providing a pressure-tight seal connected adjacent to each opening of the pressure-tight suit for operative engagement of a body part surface of the user;
(c) providing inlet means in the suit for introduction of at least one source of positive pressure to an interior of the suit between the user's body parts and the suit to create a differential pressure condition therein between the positive pressure condition inside the suit, and a pressure condition existing outside the suit;
(d) providing rigid support means incorporated into the suit for accommodating the movements of the user's body, while counteracting a downwards force applied to the suit when it is placed under the differential pressure condition;
(e) whereby the differential pressure condition contained inside the suit exerts an upwards force upon the user's body to offload a portion of the weight of the body to the support means to facilitate the treatment procedure undergone by the user.

* * * * *